US012576268B2

(12) United States Patent     (10) Patent No.:   US 12,576,268 B2

Horn et al.               (45) Date of Patent:     Mar. 17, 2026

(54) CONFORMABLE NEURAL INTERFACE DEVICE WITH HYDROGEL ADHESION AND METHODS OF USING THE SAME

(71) Applicants:University of Pittsburgh-Of the Commonwealth System of Higher Education, Pittsburgh, PA (US); Carnegie Mellon University, Pittsburgh, PA (US)

(72) Inventors: Charles C. Horn, Pittsburgh, PA (US); Gutian Xiao, Pittsburgh, PA (US); Christopher J. Bettinger, Pittsburgh, PA (US); Gary Keith Fedder, Pittsburgh, PA (US); Xiao Chuan Ong, Pittsburgh, PA (US); Wei-Chen Huang, Pittsburgh, PA (US); Lee Erik Bartholomew Fisher, Pittsburgh, PA (US); Robert A. Gaunt, Pittsburgh, PA (US)

(73) Assignees: University of Pittsburgh—Of the Commonwealth System of Higher Education, Pittsburgh, PA (US); Carnegie Mellon University, Pittsburgh, PA (US)

( * ) Notice: Subject to any disclaimer, the term of this patent is extended or adjusted under 35 U.S.C. 154(b) by 1265 days.

(21) Appl. No.: 17/260,203

(22) PCT Filed: Jul. 20, 2018

(86) PCT No.: PCT/US2018/043161

§ 371 (c)(1),
(2) Date: Jan. 13, 2021

(87) PCT Pub. No.: WO2020/018120

PCT Pub. Date: Jan. 23, 2020

(65) Prior Publication Data

US 2021/0268268 A1      Sep. 2, 2021

(51) Int. Cl.
| | |
|---|---|
| *A61N 1/05* | (2006.01) |
| *A61N 1/36* | (2006.01) |
| *A61N 1/375* | (2006.01) |

(52) U.S. Cl.
CPC ........... *A61N 1/059* (2013.01); *A61N 1/0539* (2013.01); *A61N 1/0568* (2013.01); *A61N 1/36135* (2013.01); *A61N 1/37518* (2017.08)

(58) Field of Classification Search
CPC .. A61N 1/059; A61N 1/37518; A61N 1/0539; A61N 1/0568; A61N 1/36135;

(Continued)

(56) References Cited

U.S. PATENT DOCUMENTS

| | | | | |
|---|---|---|---|---|
| 2008/0021525 A1* | 1/2008 | Solzbacher | .............. | A61N 2/02 |
| | | | | 427/2.24 |
| 2010/0331935 A1* | 12/2010 | Tabada | ..................... | A61N 1/05 |
| | | | | 600/377 |

(Continued)

FOREIGN PATENT DOCUMENTS

| | | | | | |
|---|---|---|---|---|---|
| CN | | 105646902 A | * | 6/2016 | ............. A61K 33/26 |
| WO | WO-2008122044 A2 | * | 10/2008 | | ............. A61N 1/326 |

OTHER PUBLICATIONS

Tanaka, Toshimi, "Determination of Fracture Energy of High Strength Double Network Hydrogels", Apr. 9, 2005, Creative Research Initiative "Sousei" (CRIS) (Year: 2005).*

(Continued)

*Primary Examiner* — Adam Z Minchella
(74) *Attorney, Agent, or Firm* — Foley & Lardner LLP

(57)          ABSTRACT

Disclosed are highly compliant bioelectronic neural interface devices with hydrogel adhesion. Example devices include adhesion-promoting functional groups that facilitate enhanced electrical contact with the nerve without the need for continuous application of pressure. A transfer process (Continued)

may be used to fabricate the device using a sacrificial material (e.g., polyacrylic acid (PAA)) that has tunable solubility in aqueous media, helping avoid the need for harsher release chemicals that may affect the properties of the hydrogel. The transfer process also helps achieve electrode contacts that are flush with a surface of the device and facilitate more intimate contact with the nerve. A gradual change in Young's modulus from a stiff contact pad region to a more compliant electrode contact region may be achieved via a varied amount of an epoxy-based material (such as SU-8) and with silicone-based material (such as polydimethylsiloxame (PDMS)) to encapsulate the device cable.

27 Claims, 26 Drawing Sheets

(58) Field of Classification Search
CPC .. A61B 17/1128; A61B 17/11; A61B 17/1132
See application file for complete search history.

(56) References Cited

U.S. PATENT DOCUMENTS

| | | | | |
|---|---|---|---|---|
| 2011/0087315 | A1* | 4/2011 | Richardson-Burns | ...................... A61N 1/0536 205/198 |
| 2017/0156621 | A1* | 6/2017 | Bettinger | ............. A61N 1/0496 |
| 2017/0209389 | A1* | 7/2017 | Toth | ..................... A61B 5/4848 |
| 2018/0000983 | A1* | 1/2018 | Schneider | ........... A61L 24/0031 |
| 2018/0064931 | A1* | 3/2018 | Clements | ............... A61B 5/388 |

OTHER PUBLICATIONS

Huang W, Translation of CN-105646902-A, Jun. 8, 2016 (Year: 2016).*
Pan, Jian-Ming, Translation of CN 105646902, 2016 (Year: 2016).*
Medgadget, Soft and Highly Flexible Neural Interfaces Prevent Injury to Brain, May 24, 2018, 3 pages.
Huang, et al., "Ultrasound-Mediated Self-Healing Hydrogels Based on Tunable Metal-Organic Bonding," *American Chemical Society*, vol. 18, pp. 1162-1171 (2017).
Huang, et al., "Ultracompliant Hydrogel-Based Neural Interfaces Fabricated by Aqueous-Phase Microtransfer Printing," *Advanced Functional Materials*, 12 pages, May 24, 2018.
International Search Report issued in International Patent Application No. PCT/US2018/043161, filed Jul. 20, 2018.
Ding et al., "Mussel-inspired Polydopamine for bio-surface Functionalization," *Biosurf. Biotribol.*, vol. 2, No. 4, pp. 121-136 (Dec. 2016).
Forooshani, et al., "Recent Approaches in Designing Bioadhesive Materials Inspired by Mussel Adhesive Protein," *Journ. of Polymer Chemistry*, vol. 55, No. 1, pp. 9-33 (Jan. 2017).
Han, et al., "Tough, Self-Healable and Tissue-Adhesive Hydrogel with Tunable Multifunctionality," *NPG Asia Materials*, vol. 9, pp. 1-12 (2017).
Horn, et al., "Thoracic cross-over pathways of the rat vagal trunks," *Brain Res.*, vol. 1060(1-2), pp. 153-161 (Oct. 2005).
Ong, et al., "Ultra-Compliant Peripheral Nerve Cuff Electrode with Hydrogel Adhesion," Carnegie Mellon University, pp. 376-379 (Jan. 2018).
International Preliminary Report on Patentability issued in International Patent Application No. PCT/US2018/043161, dated Feb. 4, 2021.

* cited by examiner

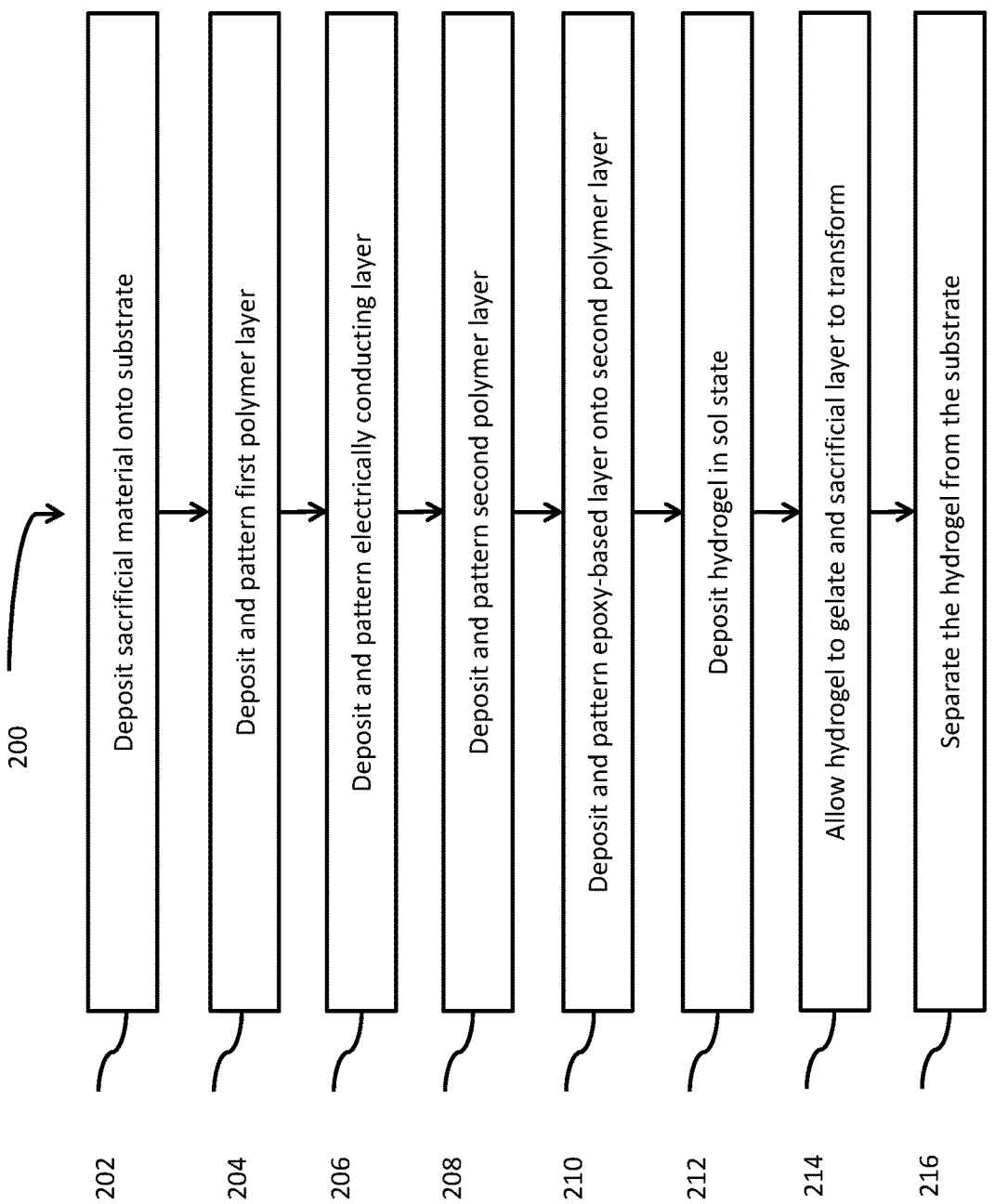

200

202   Deposit sacrificial material onto substrate

204   Deposit and pattern first polymer layer

206   Deposit and pattern electrically conducting layer

208   Deposit and pattern second polymer layer

210   Deposit and pattern epoxy-based layer onto second polymer layer

212   Deposit hydrogel in sol state

214   Allow hydrogel to gelate and sacrificial layer to transform

216   Separate the hydrogel from the substrate

400
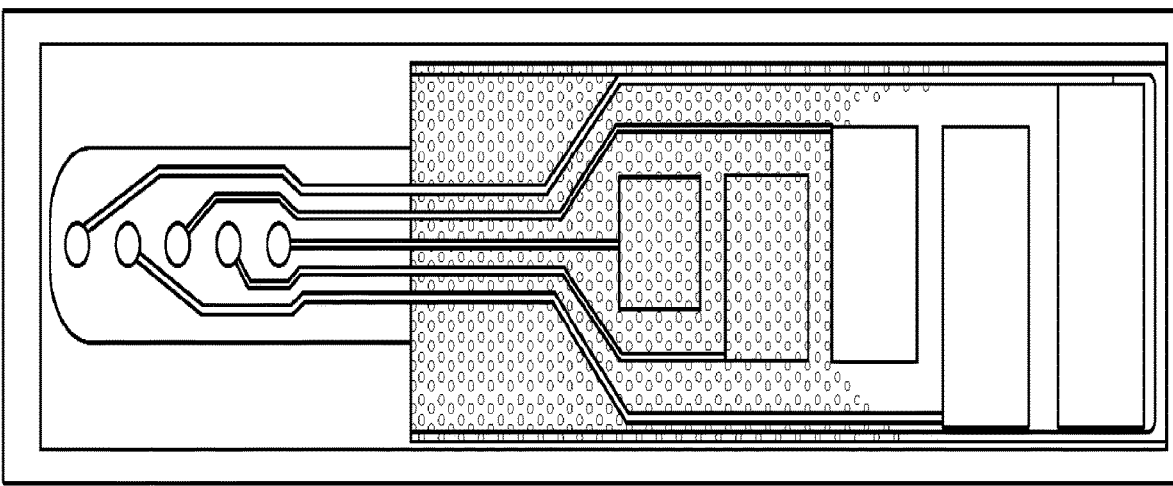
430
420
Figure 4B

800

802    Access a nerve via a surgical procedure

804    Identify a nerve location at which to attach a neural interface device

806    Attach the neural interface device to the nerve at the nerve location

808    Close the surgical site

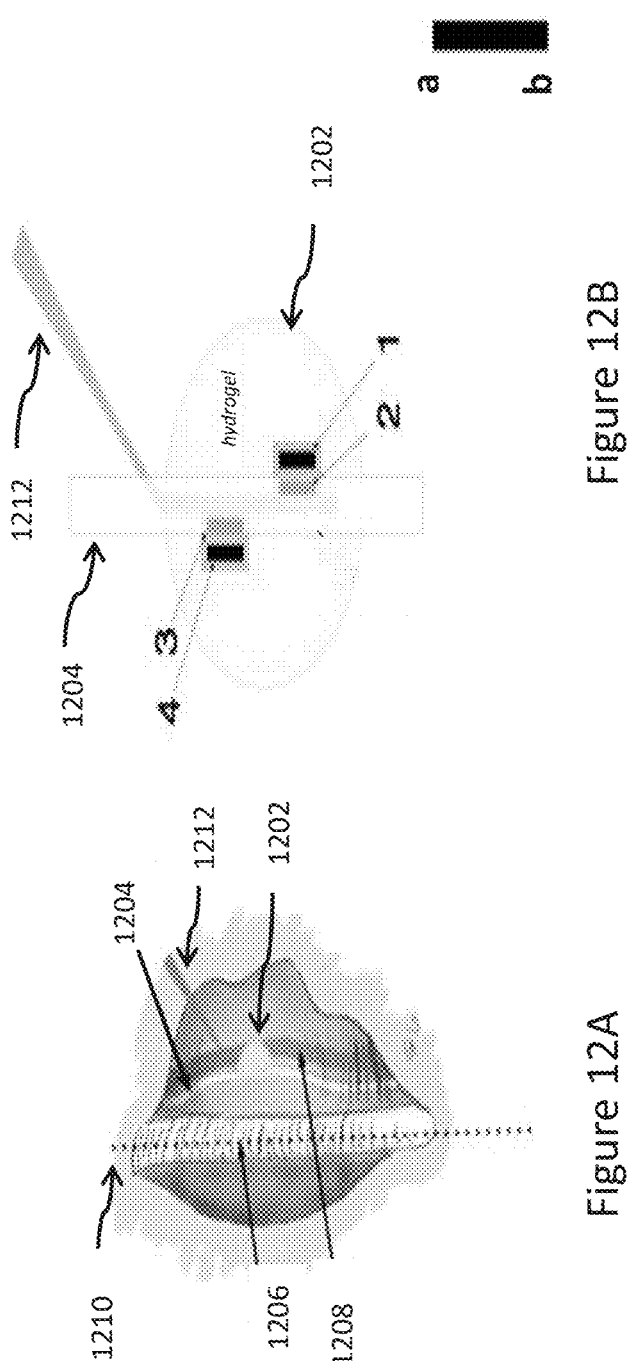
Figure 12A
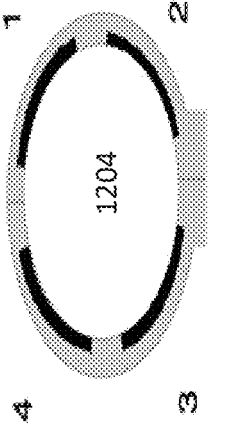
Figure 12B
Figure 12C

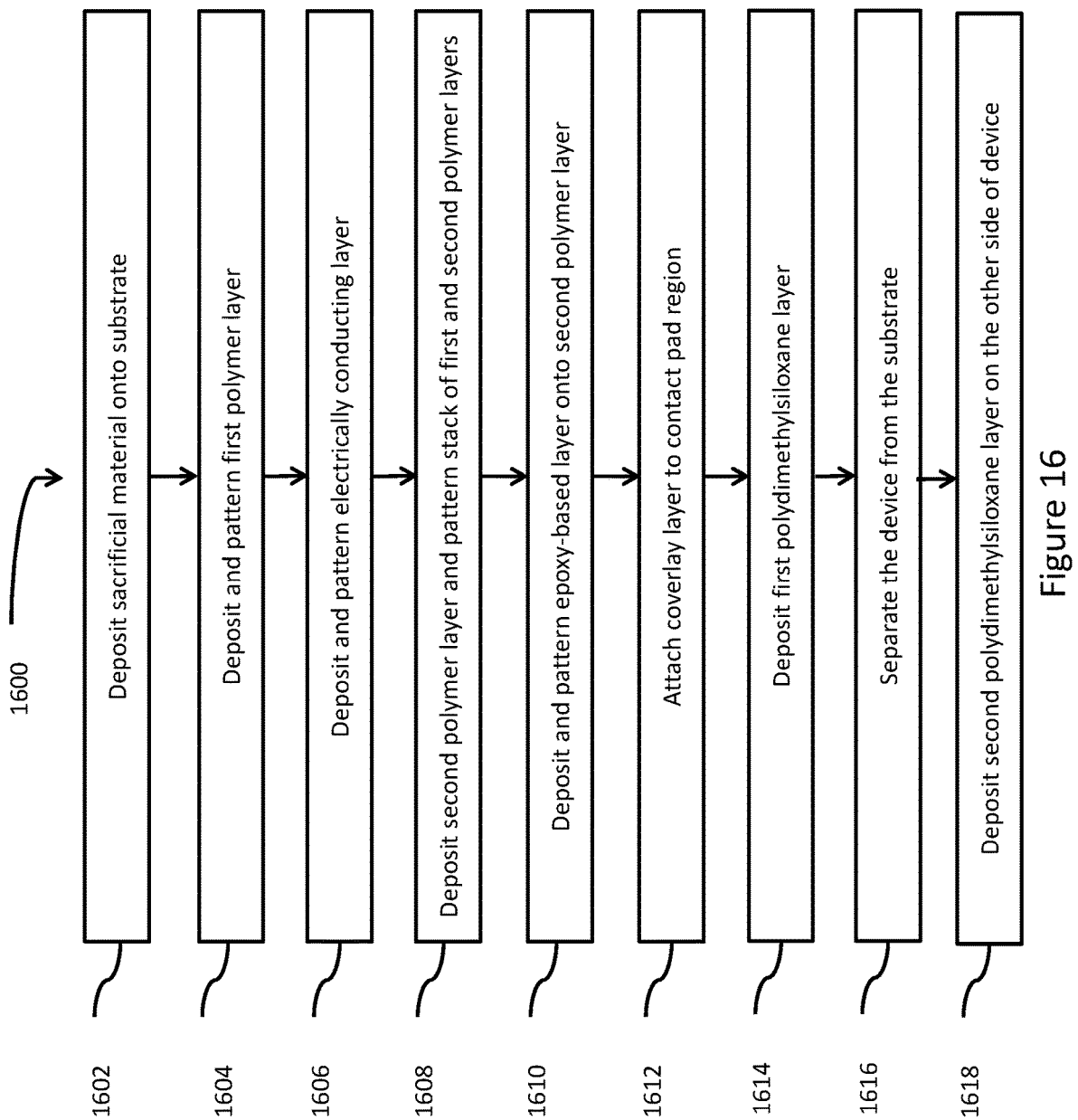

1600

1602 — Deposit sacrificial material onto substrate

1604 — Deposit and pattern first polymer layer

1606 — Deposit and pattern electrically conducting layer

1608 — Deposit second polymer layer and pattern stack of first and second polymer layers 1610 — Deposit and pattern epoxy-based layer onto second polymer layer 1612 — Attach coverlay layer to contact pad region 1614 — Deposit first polydimethylsiloxane layer 1616 — Separate the device from the substrate 1618 — Deposit second polydimethylsiloxane layer on the other side of device

Figure 16

500 µm diameter

450 µm diameter

350 µm diameter 100 um diameter 200 um diameter 300 um diameter

Silicon handle substrate

Cervical vagus probe

Abdominal vagus probe

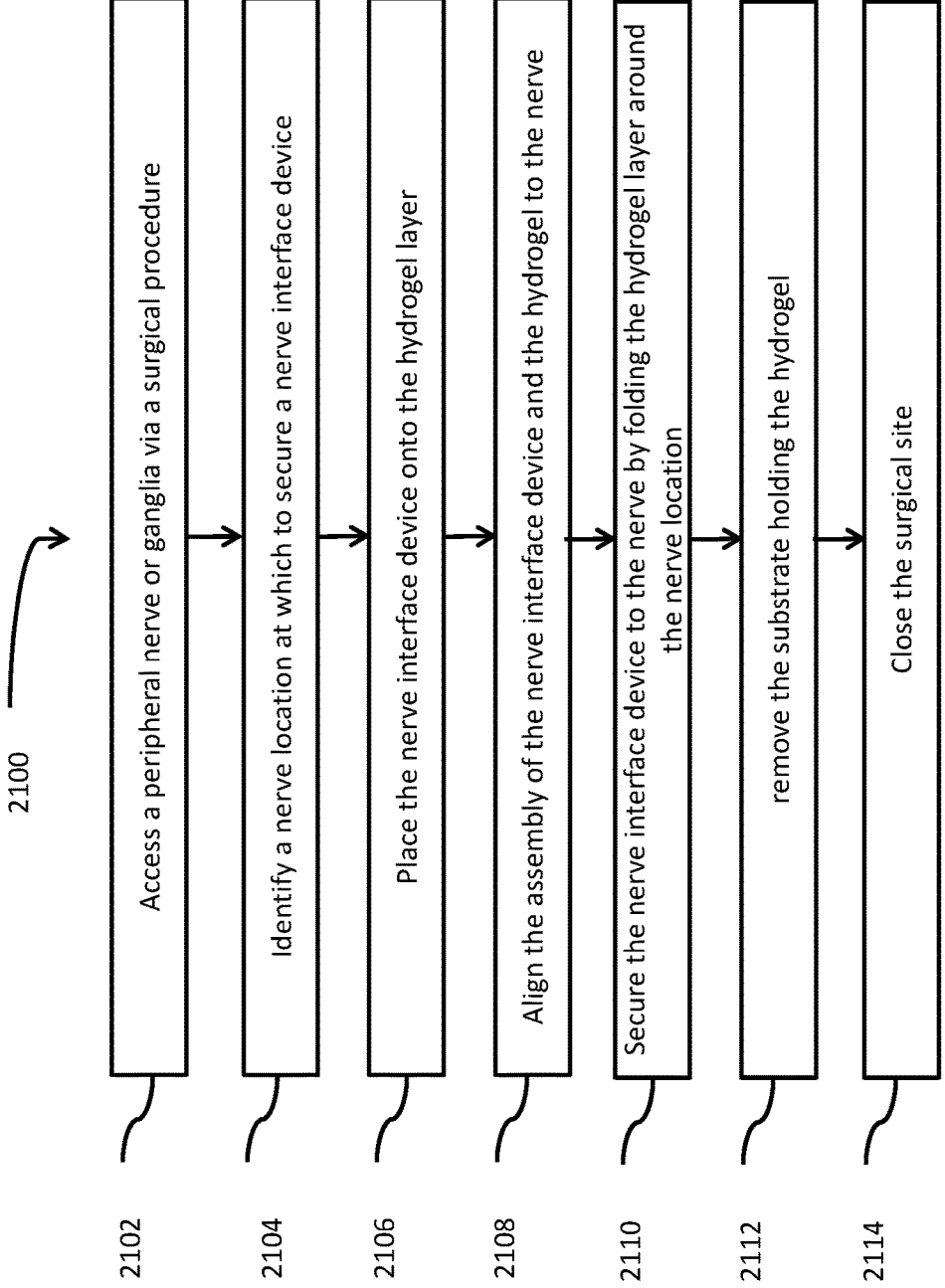

2100

Access a peripheral nerve or ganglia via a surgical procedure

Identify a nerve location at which to secure a nerve interface device

Place the nerve interface device onto the hydrogel layer

Align the assembly of the nerve interface device and the hydrogel to the nerve

Secure the nerve interface device to the nerve by folding the hydrogel layer around the nerve location remove the substrate holding the hydrogel Close the surgical site

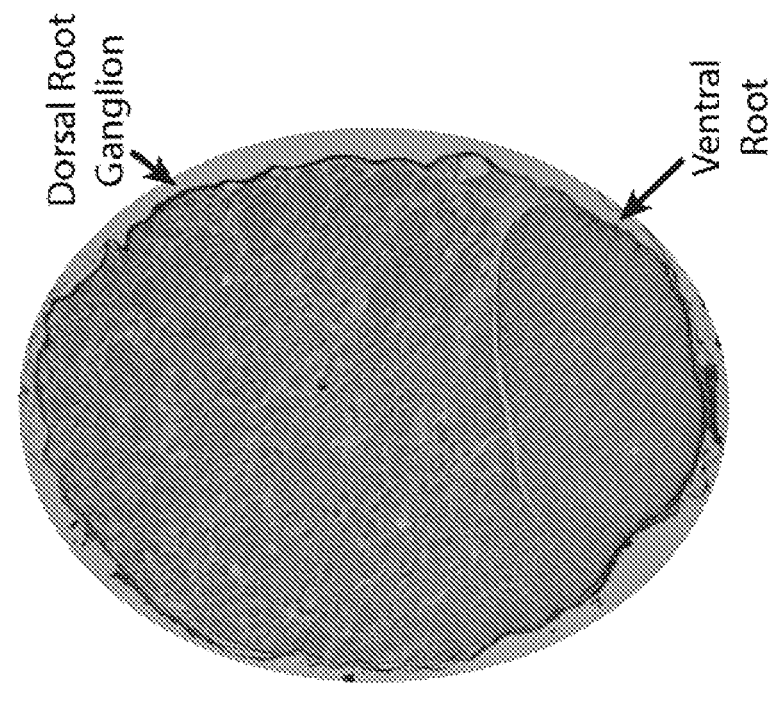
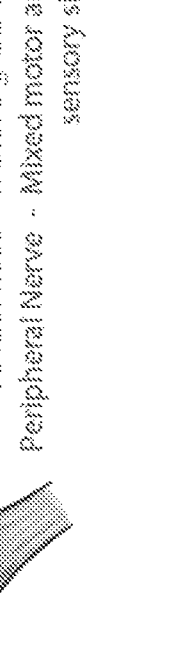
Figure 25

CONFORMABLE NEURAL INTERFACE DEVICE WITH HYDROGEL ADHESION AND METHODS OF USING THE SAME

CROSS-REFERENCE TO RELATED APPLICATION

This application is a U.S. National Stage of International Patent Application No. PCT/US2018/043161, filed Jul. 20, 2018. The contents of this application is incorporated herein by reference in its entirety.

BACKGROUND

A neural interface can serve to bridge the nervous system with a machine interface to achieve one-way or two-way communication. Neural interfaces commonly include electrodes used in sending and receiving electrical signals. Sensing and stimulating nerves in the peripheral nervous system ("peripheral nerves") is useful for numerous applications, such as therapies for dysfunction of major organ systems, such as the heart, lungs, gastrointestinal tract, muscular system, immune system and even neuron system itself. Peripheral neural interfaces can include intrafascicular electrodes, which are invasive, and extraneural electrodes, which are relatively non-invasive. Although extraneural electrodes have the advantage of being less invasive, they may not provide the same spatial selectivity in recording and stimulation because of the increased separation of electrodes from fascicles, which contain a functionally important subset of neuronal fibers to target disease.

SUMMARY

The present disclosure provides systems, apparatuses and methods relating to bioelectronic conformable neural interface devices that address shortcomings of existing neural interfaces, such as by being relatively non-invasive yet able to achieve enhanced selectivity, having enhanced mechanical compliance to more readily conform to peripheral nerves and ganglia, and/or facilitating a better mechanical contact with peripheral neural tissues, including cell bodies or axons, without subjecting the neural tissue to as much mechanical pressure.

In one aspect, the present disclosure provides a suture-like anchor device comprising a gel polymer network that is configured to couple with a probe, wherein the gel polymer network comprises a crosslinkable polymer precursor that is cross linked with a redox active metal.

Also disclosed herein is a suture-like anchor device comprising a gel polymer network having an effective interfacial adhesion of between 0.1 and 10 $J/m^2$ and/or a fracture energy between about 100 to about 1,000 $J/m^2$, wherein the gel polymer network (a) comprises a crosslinkable polymer precursor; and (b) is configured to couple with a probe. In certain embodiments, the crosslinkable polymer precursor is cross linked with a redox active metal.

In some embodiments of the suture-like anchor devices of the present technology, the redox active metal is $Fe^{3+}$, $Au^{3+}$, $V^{5+}$, or $Ag^+$. Additionally or alternatively, in some embodiments, the crosslinkable polymer precursor is selected from the group consisting of polyethylene glycol (PEG), poly(ethylene oxide), gelatin, albumin, poly(ethylene glycol-co-propylene glycol), poly(vinyl pyrrolidinone), poly(vinyl alcohol), polybutylene terephthalate, polysaccharides (including dextran, chitosan, carboxymethyl, curdlan, and pullulan), acrylic polymers, methacrylic polymers, poly(alpha-hydroxy acids), polylactides, polyglycolides, polyacrylamides, polyamides, polyanhydrides, and any block copolymers thereof. The gel polymer network may comprise a hydrogel and/or a dopamine moiety. In some embodiments, the gel polymer network comprises a stimulus-responsive telechelic Dopa-modified polyethylene glycol-based hydrogel. In any of the above embodiments, the gel polymer network can comprise an adhesive hydrogel that includes a drug, ligand, or peptide that binds to a site expressed on a target tissue.

Additionally or alternatively, in some embodiments, the gel polymer network has a thickness of about 0.2 mm, about 0.25 mm, about 0.5 mm, about 0.75 mm, about 1 mm, about 1.25 mm, about 1.5 mm, about 1.75 mm, about 2 mm, about 2.25 mm, about 2.5 mm, about 2.75 mm, about 3 mm, about 3.25 mm, or about 3.5 mm. In certain embodiments, the characteristic Young's modulus of the suture-like anchor device can range from 10 kPa to 100 kPa. Additionally or alternatively, in some embodiments, the shear modulus (G) of the suture-like anchor device can range from 1 kPa to 100 kPa. The yield strength of the suture-like anchor device can range from 1 Pa to 1000 Pa, and the ultimate tensile strength of the suture-like anchor device can range from 10 kPa to 100 kPa.

Additionally or alternatively, in some embodiments, the gel polymer network is deposited on a detachable surgical support substrate, such as parafilm, polytetrafluoroethylene, nylon, or any other type of inert polymer film.

In another aspect, the present disclosure provides suture-like anchor devices for use in surgically implanting an electrode onto a target tissue in a subject. The target tissue may comprise any suitable tissue, such as a nerve, a ganglion, muscle tissue, cardiac tissue, gastrointestinal tissue, liver tissue, pancreatic tissue, or spleen tissue.

In one aspect, the present disclosure provides a method for surgically implanting a probe onto a target tissue in a subject comprising: (a) placing a first surface of the probe onto an adhesive hydrogel layer, wherein the adhesive hydrogel layer comprises a first portion and a second portion; (b) placing a second surface of the probe onto a surface of the target tissue, wherein the second surface of the probe is opposite to the first surface of the probe; and (c) wrapping the adhesive hydrogel layer around the target tissue such that the first portion of the adhesive hydrogel layer contacts the second portion of the adhesive hydrogel layer. The probe may be placed between the first portion and the second portion of the adhesive hydrogel layer. In some embodiments, the length of the probe is less than the circumference of the target tissue. Additionally or alternatively, in some embodiments, the length of the adhesive hydrogel layer is greater than the circumference of the target tissue. The second surface of the probe may be placed onto a dorsal, a ventral, a lateral, an anterior or a posterior surface of the target tissue. In some embodiments, the subject is a human.

Additionally or alternatively, in some embodiments of the method, the adhesive hydrogel layer is deposited onto a detachable surgical support substrate such as parafilm, polytetrafluoroethylene, nylon, or any other type of inert polymer film. In some embodiments, the method further comprises removing the detachable surgical support substrate.

The target tissue may comprise any suitable tissue, such as a nerve, a ganglion, muscle tissue, cardiac tissue, gastrointestinal tissue, liver tissue, pancreatic tissue, or spleen tissue. Examples of nerves include, but are not limited to, abdominal aortic plexus, abducens nerve, accessory nerve, accessory obturator nerve, alderman's nerve, anococcygeal nerve, ansa cervicalis, anterior interosseous nerve, anterior superior alveolar nerve, Auerbach's plexus, auriculotemporal nerve, axillary nerve, brachial plexus, buccal branch of the facial nerve, buccal nerve, cardiac plexus, cavernous nerves, cavernous plexus, cervical branch of the facial nerve, cervical plexus, chorda tympani, coccygeal nerve, cochlear nerve, common fibular nerve, common palmar digital nerves of median nerve, deep branch of the radial nerve, deep fibular nerve, deep petrosal nerve, deep temporal nerves, digastric branch of facial nerve, dorsal branch of ulnar nerve, dorsal nerve of clitoris, dorsal nerve of the penis, dorsal scapular nerve, esophageal plexus, ethmoidal nerves, external laryngeal nerve, external nasal nerve, facial nerve, femoral nerve, frontal nerve, gastric plexuses, genital branch of genitofemoral nerve, genitofemoral nerve, glossopharyngeal nerve, greater auricular nerve, greater occipital nerve, greater petrosal nerve, hepatic plexus, hypoglossal nerve, iliohypogastric nerve, ilioinguinal nerve, inferior alveolar nerve, inferior anal nerves, inferior cardiac nerve, inferior gluteal nerve, inferior hypogastric plexus, inferior mesenteric plexus, inferior palpebral nerve, infraorbital nerve, infraorbital plexus, infratrochlear nerve, intercostal nerve, intercostobrachial nerve, intermediate cutaneous nerve, internal carotid plexus, internal laryngeal nerve, interneuron, lacrimal nerve, lateral cord, lateral cutaneous nerve of forearm, lateral cutaneous nerve of thigh, lateral pectoral nerve, lateral plantar nerve, lateral pterygoid nerve, lesser occipital nerve, lingual nerve, long ciliary nerves, long thoracic nerve, lower subscapular nerve, lumbar nerves, lumbar plexus, lumbar splanchnic nerves, lumboinguinal nerve, lumbosacral plexus, lumbosacral trunk, mandibular nerve, marginal mandibular branch of facial nerve, masseteric nerve, maxillary nerve, medial cord, medial cutaneous nerve of arm, medial cutaneous nerve of forearm, medial cutaneous nerve, medial pectoral nerve, medial plantar nerve, medial pterygoid nerve, median nerve, Meissner's plexus, mental nerve, middle cardiac nerve, middle meningeal nerve, motor nerve, muscular branches of the radial nerve, musculocutaneous nerve, mylohyoid nerve, nasociliary nerve, nasopalatine nerve, nerve of pterygoid canal, nerve to obturator internus, nerve to quadratus femoris, nerve to the Piriformis, nerve to the stapedius, nerve to the subclavius, nervus intermedius, nervus spinosus, obturator nerve, oculomotor nerve, olfactory nerve, ophthalmic nerve, optic nerve, ovarian plexus, palatine nerves, palmar branch of the median nerve, palmar branch of ulnar nerve, pancreatic plexus, patellar plexus, pelvic splanchnic nerves, perforating cutaneous nerve, perineal branches of posterior femoral cutaneous nerve, perineal nerve, pharyngeal branch of vagus nerve, pharyngeal branches of glossopharyngeal nerve, pharyngeal nerve, pharyngeal plexus, phrenic nerve, phrenic plexus, posterior auricular nerve, posterior branch of spinal nerve, posterior cord, posterior cutaneous nerve of arm, posterior cutaneous nerve of forearm, posterior cutaneous nerve of thigh, posterior scrotal nerves, posterior superior alveolar nerve, proper palmar digital nerves of median nerve, prostatic plexus (nervous), pudendal nerve, pudendal plexus, pulmonary branches of vagus nerve, radial nerve, recurrent laryngeal nerve, renal plexus, sacral plexus, sacral splanchnic nerves, saphenous nerve, sciatic nerve, sensory nerve, short ciliary nerves, sphenopalatine nerves, splenic plexus, stylohyoid branch of facial nerve, subcostal nerve, suboccipital nerve, superficial branch of the radial nerve, superficial fibular nerve, superior cardiac nerve, superior gluteal nerve, superior hypogastric plexus, superior labial nerve, superior laryngeal nerve, superior lateral cutaneous nerve of arm, superior mesenteric plexus, superior rectal plexus, supraclavicular nerves, supraorbital nerve, suprarenal plexus, suprascapular nerve, supratrochlear nerve, sural nerve, sympathetic trunk, temporal branches of the facial nerve, third occipital nerve, thoracic aortic plexus, thoracic splanchnic nerves, thoraco-abdominal nerves, thoracodorsal nerve, tibial nerve, transverse cervical nerve, trigeminal nerve, trochlear nerve, tympanic nerve, ulnar nerve, upper subscapular nerve, uterovaginal plexus, vagus nerve, ventral ramus, vesical nervous plexus, vestibular nerve, vestibulocochlear nerve, zygomatic branches of facial nerve, zygomatic nerve, zygomaticofacial nerve, or zygomaticotemporal nerve.

Examples of ganglia include, but are not limited to, dorsal root ganglion, cranial nerve ganglion, autonomic ganglion, basal ganglion, celiac ganglion, ciliary ganglion, geniculate ganglion, inferior cervical ganglion, jugular ganglion, long root of the ciliary ganglion, middle cervical ganglion, nodose ganglion, otic ganglion, petrous ganglion, pterygopalatine ganglion, semilunar ganglion, submandibular ganglion, superior cervical ganglion, superior ganglion of glossopharyngeal nerve, or superior ganglion of vagus nerve.

Examples of muscle tissue include skeletal muscle, smooth muscle and cardiac muscle.

Additionally or alternatively, in some embodiments of the method, the adhesive hydrogel layer comprises a crosslinkable polymer precursor that is cross linked with a redox active metal, such as $Fe^{3+}$, $Au^{3+}$, $V^{5+}$, or $Ag^+$.

Additionally or alternatively, in some embodiments, the method further comprises detecting or monitoring bioelectrical signals generated by the target tissue. Additionally or alternatively, in some embodiments, the method further comprises detecting or monitoring the levels of one or more hormones, neurotransmitters, immune cells, interleukins, cytokines, lymphokines, chemokines, growth factors, and enzymes in a subject.

In one aspect, the conformable neural interface system of the present disclosure may be used to stimulate or inhibit a nerve in a subject in need thereof. The subject may suffer from a disease or medical condition that affects a system or an organ. The organ can be, for example, selected from the group consisting of heart, brain, lungs, an organ of a respiratory system, liver, kidney, stomach, small intestine, large intestine, a muscle of a limb, central nervous system, peripheral nervous system, pancreas, bladder, skin, urinary tract, thyroid gland, pituitary gland, and adrenal cortex.

In another aspect, the conformable neural interface system of the present disclosure may be used for modulating the levels of one or more hormones, neurotransmitters, immune cells, interleukins, cytokines, lymphokines, chemokines, growth factors, and/or enzymes in a subject.

At least one aspect is directed to a bioelectronic neural interface device. The device can comprise one or more polymer layers, an electrically conducting layer, and an adhesive gel layer. An electrode contact region may be configured to interface with a tissue, nerve or ganglion. A plurality of electrodes may be substantially flush with a surface of the electrode contact region for contact with the tissue, nerve, or ganglion. An adhesive hydrogel may be configured to adhere the electrode contact region to the nerve, tissue or ganglion such that the electrodes contact the nerve, tissue or ganglion. A cable electrically and mechanically connects the electrode contact region to the contact pad region, also known as the cable connector region, that may have a plurality of contact pads. The cable connector region may be configured to interface with at least one of a neural signal sensor and a stimulator.

In certain implementations, the electrode contact region may be relatively more compliant than the relatively stiffer contact pad region.

In certain implementations, the device is configured to provide an interface between electrode contacts and the nerve, tissue or ganglion without penetrating an epineurium of the nerve, tissue or ganglion.

In certain implementations, the electrode contact and pad regions form at least part of a probe. The probe may rise in stiffness from the electrode contact region to the contact pad region.

In certain implementations, a quantity of an epoxy-based material may be varied between the electrode contact region and the pad region. Stiffness may increase as the quantity of the epoxy-based material increases from the electrode contact region to the pad region.

At least one aspect is directed to a method of manufacturing a bioelectronic neural interface device for interfacing with a nerve, ganglion or tissue. A sacrificial material may be deposited onto a substrate. The sacrificial material may have tunable solubility in aqueous media. First and second polymer layers sandwiching an electrically conducting layer may be deposited onto the sacrificial material. An epoxy-based layer may be deposited onto the second polymer layer. A polydimethylsiloxane layer may be deposited onto the epoxy-based layer. The neural interface device may be separated from the substrate. The neural interface device may include an electrode contact region with at least one electrode formed at least in part by the electrically conducting layer. The electrode may be substantially flush with a surface of the electrode contact region. An adhesive hydrogel layer may be drop deposited onto a separate substrate. The device may be configured to adhere to a nerve, tissue or ganglion via the hydrogel by wrapping the hydrogel around the device such that the device is in intimate contact with the nerve, tissue or ganglion.

In certain implementations, the adhesive hydrogel layer may be drop deposited onto a detachable surgical support substrate to allow easy peeling of the disk from the substrate.

In certain implementations, the epoxy-based layer may include an epoxy-based photo-patternable material.

In certain implementations, the epoxy-based layer may be patterned so as to impart a transition in stiffness from a relatively flexible electrode region to a relatively stiff pad region.

In certain implementations, the transition in thickness may be achieved at least in part by varying the volume ratio of the epoxy-based material to the hydrogel using patterned pores with varying density. The density of pores may increase from a first pore density at the pad region to a greater second pore density at the electrode contact region. In certain implementations, the epoxy-based layer may be patterned such that there is substantially no epoxy-based material in the electrode contact region.

In certain implementations, the sacrificial material may include primarily polyacrylic acid (PAA).

In certain implementations, the hydrogel may include gold.

In certain implementations, the first polymer layer may be deposited onto the sacrificial layer and patterned. The electrically conducting layer may be deposited onto the first polymer layer and patterned. The second polymer layer may be deposited onto the electrically conducting layer and patterned. Depositing and patterning the first polymer layer, the electrically conducting layer, and the second polymer layer may be part of the deposition of first and second polymer layers sandwiching an electrically conducting layer.

In certain implementations, the first and second polymer layers may be patterned via etching. In certain implementations, the electrically conducting layer may be patterned via ion milling. In certain implementations, the first and second polymer layers may include primarily parylene-C. In certain implementations, a plurality of photoresist development and removal steps may be performed. Dry etching may be performed after each of the plurality of photoresist development and removal steps.

At least one aspect is directed to a bioelectronic neural interface device prepared by the process detailed above.

At least one aspect is directed to a method of securing a bioelectronic neural interface device to a nerve, ganglion or tissue. A nerve, tissue or ganglion may be accessed via a surgical procedure. A nerve, tissue or ganglion location at which to secure the neural interface device may be identified. The neural interface device may be secured to the nerve, tissue or ganglion at the nerve, tissue or ganglion location. An electrode contact region may have a plurality of electrodes configured to interface with the nerve, tissue or ganglion. The plurality of electrodes may be substantially flush with a surface of the electrode contact region such that the electrode contact region is flush with the tissue. An adhesive hydrogel may be configured to adhere the neural interface device to the nerve, tissue or ganglion such that the electrodes contact the nerve, tissue or ganglion. The surgical site may be closed. A cable electrically and mechanically connects the electrode contact region to the contact pad region, also known as the cable connector region, that may have a plurality of contact pads. The electrode contact region may be relatively more compliant than the relatively stiffer cable connector region.

At least one aspect is directed to a method of manufacturing a bioelectronic neural interface device for interfacing with a nerve. The method comprises depositing a sacrificial material onto a substrate to form a sacrificial material layer, the sacrificial material having tunable solubility in aqueous media; depositing onto the sacrificial material, a first polymer layer; patterning the first polymer layer; depositing an electrically conducting layer; patterning the electrically conducting layer; depositing the second polymer layer; patterning a stack of the first polymer layer and the second polymer layer; depositing an epoxy-based layer onto the second polymer layer; attaching a coverlay material to a region where a contact pad is to be formed; and separating the device from the substrate.

In certain implementations, the method further comprises depositing a first silicone-based layer prior to separating the device from the substrate and depositing a second silicone-based layer on a second side of the device opposite a first side of the device on which the first silicone-based layer was deposited.

In certain implementations, the sacrificial material comprises polyacrylic acid (PAA); the sacrificial material comprises a compound selected from the group consisting of block-copolymers of PAA with a non-acrylic acid monomer, polyacrylamide polymers, and a polymer with a side group (s) comprising any ionizable moiety; the sacrificial material comprises a compound selected from the group consisting of poly(styrene)-block-poly(acrylic acid), poly(acrylamide-co-acrylic acid), poly(N-alkylacrylamide-co-acrylic acid) polymers, poly(alkylene-co-acrylic acid) polymers; the sacrificial material layer has a thickness selected from the group consisting of about 200, about 225, about 250, about 275, about 300, about 325, about 350, about 375, about 400, about 425 nm, about 450, about 475, about 500, about 525, about 550 nm, about 600 nm, about 650 nm, about 700 nm, about 750 nm, about 800 nm, about 900 nm, about 1 µm, and about 2 µm; and/or the sacrificial material layer has a thickness of about 700 nm.

In certain implementations, the sacrificial layer is cross-linked with CaCl2) solution so that the sacrificial layer does not dissolve in water; the first polymer layer and the second polymer layer serve as a moisture barrier and/or as a dielectric barrier; and/or the first polymer layer and the second polymer layer comprises a poly(p-xylylene) polymer.

In certain implementations, the thickness of the first polymer layer is about 4.5 µm; and/or the thickness of the first polymer layer is about 1 µm, about 2 µm, about 3 µm, about 4 µm, about 5 µm, about 6 µm, about 7 µm, about 8 µm, about 9 µm, about 10 µm, about 15 µm, about 20 µm, or about 25 µm.

In certain implementations, patterning the first polymer layer comprises patterning the first polymer layer to form tapered sidewalls by blurring the edges during exposure; patterning the first polymer layer to form tapered sidewalls by blurring the edges during exposure comprises (i) flipping a transparency mask and (ii) plasma etching the first polymer layer to form vias in the first polymer layer.

In certain implementations, the electrically conducting layer (a) comprises a material allows the flow of a suitable electrical current; (b) comprises a biologically inert material; (c) comprises a biologically compatible conductive metal or and polymer; (d) comprises a metal selected from the group consisting of platinum, gold, platinum/iridium, and titanium; (e) comprises a polymer selected from the group consisting of polypyrrole, polyaniline, poly (3,4-ethylenedioxythiophene), poly(3-hexylthiophene), polythiophene, poly(3-octylthiophnene-3-methylthiophene), poly(p-phenylene-terephthalamide), polythiophene-vinylene, poly(3-alkylthiophene), poly(p-phenylene), poly-p-phenylene-sulphide, polybutadiene, poly(p-phenylenevinylene), poly (p-phenylene-terephthalamide), polyacetylene, polyfuran, polyisoprene, polyazulene, poly(isothianaphthene), and poly (α-naphthylamine); (f) comprises platinum; (g) has a thickness selected from the group consisting of about 25, about 50, about 75, about 80, about 90, about 100, about 110, about 120, about 130, about 140, about 150, about 175, about 200, about 225, about 250, about 275, about 300, about 325, about 350, about 375, about 400, about 425 nm, about 450, about 475, about 500, about 525, about 550, about 575, about 600, about 625, about 650, about 675, about 700, about 725, about 750, about 775, about 800 nm, about 850 nm, about 900 nm, about 950 nm, or about 1 µm thick; and/or (h) has a thickness of about 125 nm.

In certain implementations, the epoxy-based layer includes an epoxy-based photo-patternable material; comprises a polymer with a crosslinkable epoxide side group; and/or comprises a polymer selected from the group consisting of SU-8, HARE-SQ (KemLab) and EPON Resin 1002F; patterning a stack of the first polymer layer and the second polymer layer comprises (i) patterning the epoxy-based layer so as to impart a transition in stiffness from a relatively flexible electrode contact region to a relatively stiff contact pad (cable connector) region; and/or (ii) patterning the epoxy-based layer so as to impart a transition in stiffness from a relatively flexible electrode region to a relatively stiff contact pad (cable connector) region, wherein the transition in thickness is achieved at least in part by varying the volume ratio of the epoxy-based material to the hydrogel using patterned pores with varying density, wherein the density of pores increases from a first pore density at the contact pad region to a greater second pore density at the electrode contact region.

In certain implementations, (a) the epoxy-based layer is patterned such that there is substantially no epoxy-based material in the electrode contact region; (b) the first and second polymer layers are patterned via etching; (c) the electrically conducting layer is patterned via ion milling; and/or (d) the first and second polymer layers comprise parylene-C.

In certain implementations, the method further comprising a plurality of photoresist development and removal steps, wherein dry etching is performed after each of the plurality of photoresist development and removal steps.

At least one aspect is directed to a conformable neural interface system comprising (a) a neural interface device prepared by a process as disclosed herein; and (b) the suture-like anchor device as disclosed herein.

In certain implementations, the conformable neural interface system (a) for use in stimulating or inhibiting a nerve in a subject in need thereof; (b) for use wherein the subject suffers from a disease or medical condition that affects a system or an organ selected from the group consisting of heart, brain, lungs, an organ of a respiratory system, liver, kidney, stomach, small intestine, large intestine, a muscle of a limb, central nervous system, peripheral nervous system, pancreas, bladder, skin, urinary tract, thyroid gland, pituitary gland, and adrenal cortex; and/or (c) for use in modulating the levels of one or more hormones, neurotransmitters, immune cells, interleukins, cytokines, lymphokines, chemokines, growth factors, and/or enzymes in a subject.

At least one aspect is directed to a bioelectronic neural interface device comprising: (a) at least one first polymer layer; (b) an electrically conducting layer; (c) a probe region comprising an electrode contact region comprising a plurality of electrodes; and (d) an adhesive hydrogel layer, wherein the electrode contact region is configured to interface with a nerve, ganglion or tissue, and wherein the adhesive hydrogel layer is configured to adhere the electrode contact region to the nerve, ganglion or tissue such that the plurality of electrodes contact the nerve, ganglion or tissue.

In certain implementations, (a) the electrode contact region forms a first portion of a first surface of the neural interface device, and wherein the adhesive hydrogel layer forms a second portion of a second surface of the neural interface device opposite the first surface; and/or (b) the device further comprises a second polymer layer between the electrically conducting layer and the hydrogel layer; and/or (c) the device is configured to provide an interface between electrode contacts and the nerve without penetrating an epineurium of the nerve.

In certain implementations, wherein the first and second polymer layers (a) comprises polymers with a relatively low dielectric constant; (b) comprises a compound selected from the group consisting of a fluorinated polymer, an aryl comprising polymer, an heteroaryl comprising polymer, and silicon comprising polymers; (c) comprises a compound selected from the group consisting of Teflon, polystyrene, a parylene, parylene-c, and polysilsesquioxane; (d) comprises parylene-c; (e) have a thickness selected from the group consisting of about 50 nm, about 75 nm, about 100 nm, about 125 nm, about 150 nm, about 175 nm, about 200 nm, about 225 nm, about 250 nm, about 275 nm, about 300 nm, about 325 nm, about 350 nm, and about 375 nm; and/or (f) have a thickness of about 250 nm.

In certain implementations, the electrically conducting layer (the electrically conducting layer (a) comprises a material allows the flow of a suitable electrical current; (b)

comprises a biologically inert material; (c) comprises a biologically compatible conductive metal or and polymer; (d) comprises a metal selected from the group consisting of platinum, gold, platinum/iridium, and titanium; (e) comprises a polymer selected from the group consisting of polypyrrole, polyaniline, poly (3,4-ethylenedioxythiophene), poly(3-hexylthiophene), polythiophene, poly(3-octylthiophnene-3-methylthiophene), poly(p-phenylene-terephthalamide), polythiophene-vinylene, poly(3-alkylthiophene), poly(p-phenylene), poly-p-phenylene-sulphide, polybutadiene, poly(p-phenylenevinylene), poly (p-phenylene-terephthalamide), polyacetylene, polyfuran, polyisoprene, polyazulene, poly(isothianaphthene), and poly (α-naphthylamine); (f) comprises platinum; (g) has a thickness selected from the group consisting of about 25, about 50, about 75, about 80, about 90, about 100, about 110, about 120, about 130, about 140, about 150, about 175, about 200, about 225, about 250, about 275, about 300, about 325, about 350, about 375, about 400, about 425 nm, about 450, about 475, about 500, about 525, about 550, about 575, about 600, about 625, about 650, about 675, about 700, about 725, about 750, about 775, about 800 nm, about 850 nm, about 900 nm, about 950 nm, or about 1 m thick; and/or (h) has a thickness of about 125 nm.

In certain implementations, the adhesive hydrogel layer (a) comprises a crosslinkable polymer precursor that is cross linked with a redox active metal, wherein the redox active metal is optionally Fe3+ or Au+; (b) comprises polyethylene glycol; (c) comprises a polymer crosslinked to form a hydrogel; (d) comprises a crosslinked polymers selected from the group consisting of poly(ethylene oxide), poly (ethylene glycol-co-propylene glycol), poly(vinyl pyrrolidinone), poly(vinyl alcohol), acrylic polymers, and methacrylic polymers; (e) comprises a synthetically prepared monomer crosslinked to form a hydrogel, wherein the monomer is selected from the group consisting of ethylenically unsaturated hydrocarbons such as acrylic monomers and methacrylic monomers; (f) comprises a stimulus-responsive telechelic Dopa-modified polyethylene glycol; (g) comprises H+ ions; (h) has a thickness selected from the group consisting of about 25 μm, about 50 μm, about 75 μm, about 100 μm, about 125 μm, about 150 μm, about 175 μm, about 200 μm, about 225 μm, about 250 μm, about 275 μm, about 300 μm, about 325 μm, about 350 μm, about 400 μm, about 500 μm, about 750 μm, and about 1 mm; and/or (i) has a thickness of about 200 μm.

In certain implementations, the device further comprises (a) an epoxy-based layer between the hydrogel layer and other layers of the device; and/or (b) a cable connector region having a plurality of contact pads, the cable connector region being configured to interface with at least one of a neural signal sensor and a stimulator.

In certain implementations, the epoxy-based layer (i) is deposited on the second polymer layer; (ii) comprises an epoxy-based photo-patternable material; (iii) comprises an epoxy-based photo-patternable material which is an epoxy-based photoresist; (iv) comprises an epoxy-based photo-patternable material which is an epoxy-based photoresist which is SU-8; (v) comprises a polymer with a crosslinkable epoxide side group; (vi) comprises a polymer selected from the group consisting of SU-8 (MicroChem), HARE-SQ (KemLab) and EPON Resin 1002F; (vii) has a thickness selected from the group consisting of about 5 μm, about 10 μm, about 15 μm, about 20 μm, about 25 μm, about 30 μm, about 35 μm, and about 40 μm; and/or (viii) has a thickness of about 25 μm.

In certain implementations, the electrode contact and contact pad regions form at least part of a probe, and wherein the probe rises in stiffness from the electrode contact region to the contact pad region.

In certain implementations, the device comprises a varying quantity of the epoxy-based material that makes up the epoxy-based layer between the electrode contact region and the contact pad region, wherein stiffness increases as the quantity of the epoxy-based material increases from the electrode contact region to the contact pad region.

In certain implementations, the electrode contact region is relatively more compliant than the relatively stiffer contact pad region. In certain implementations, the plurality of electrodes are substantially flush with a surface of the electrode contact region for contact with the nerve.

In certain implementations, the substantially flush electrode contact (a) has a separation of no more than about 5 nm from the surface of the probe and the surface of the electrode contact; (b) has a separation of no more than about 25 nm from the surface of the probe and the surface of the electrode contact; (c) has a separation of no more than about 10 nm, about 15 nm, or about 20 nm from the surface of the probe and the surface of the electrode contact; (d) is configured to protrude or extend out from the surface of the probe a distance selected from the group consisting of about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, and about 25 nm.

In certain implementations, the device is for use in treating a disease or medical condition in a subject in need thereof. In certain implementations, the subject suffers from a disease or medical condition that affects a system or an organ selected from the group consisting of heart, brain, lungs, an organ of a respiratory system, liver, kidney, stomach, small intestine, large intestine, a muscle of a limb, central nervous system, peripheral nervous system, pancreas, bladder, skin, urinary tract, thyroid gland, pituitary gland, and adrenal cortex.

A method of manufacturing a bioelectronic neural interface device for interfacing with a nerve, tissue or ganglion, the method comprising (a) depositing a sacrificial material onto a substrate to form a sacrificial material layer, the sacrificial material having tunable solubility in aqueous media; (b) depositing onto the sacrificial material, first and second polymer layers sandwiching an electrically conducting layer; (c) depositing an epoxy-based layer onto the second polymer layer; (d) depositing a hydrogel in the sol state and allowing the hydrogel to gelate into a gel state, wherein the hydrogel increases the solubility of the sacrificial layer; and (e) separating the neural interface device from the substrate, wherein (i) the neural interface device comprises an electrode contact region having at least one electrode formed at least in part by the electrically conducting layer, the electrode being substantially flush with a surface of the electrode contact region, and (ii) the neural interface device is configured to adhere to a nerve, tissue or ganglion via the hydrogel.

In certain implementations, (a) the epoxy-based layer includes an epoxy-based photo-patternable material; (b) comprises a polymer with a crosslinkable epoxide side group; and/or (c) comprises a polymer selected from the group consisting of SU-8, HARE-SQ (KemLab) and EPON Resin 1002F.

In certain implementations, the method further comprising (a) patterning the epoxy-based layer so as to impart a transition in stiffness from a relatively flexible electrode contact region to a relatively stiff contact pad region; and/or (b) patterning the epoxy-based layer so as to impart a transition in stiffness from a relatively flexible electrode region to a relatively stiff contact pad region, wherein the transition in thickness is achieved at least in part by varying the volume ratio of the epoxy-based material to the hydrogel using patterned pores with varying density, wherein the density of pores increases from a first pore density at the contact pad region to a greater second pore density at the electrode contact region; (c) patterning the epoxy-based layer such that there is substantially no epoxy-based material in the electrode contact region; and/or (d) a plurality of photoresist development and removal steps, wherein dry etching is performed after each of the plurality of photoresist development and removal steps.

Certain implementations relate to a method of manufacturing a bioelectronic neural interface device for interfacing with a nerve, tissue or ganglion, wherein (a) the sacrificial material comprises polyacrylic acid (PAA); (b) the sacrificial material comprises a compound selected from the group consisting of block-copolymers of PAA with a non-acrylic acid monomer, polyacrylamide polymers, and a polymer with a side group(s) comprising any ionizable moiety; (c) the sacrificial material comprises a compound selected from the group consisting of poly(styrene)-block-poly(acrylic acid), poly(acrylamide-co-acrylic acid), poly(N-alkylacrylamide-co-acrylic acid) polymers, poly(alkylene-co-acrylic acid) polymers; (d) the sacrificial material layer has a thickness selected from the group consisting of about 200, about 225, about 250, about 275, about 300, about 325, about 350, about 375, about 400, about 425 nm, about 450, about 475, about 500, about 525, about 550 nm, about 600 nm, about 650 nm, about 700 nm, about 750 nm, about 800 nm, about 900 nm, about 1 μm, and about 2 μm; and/or (e) the sacrificial material layer has a thickness of about 700 nm.

In certain implementations, (a) the hydrogel comprises positive ions that dissolve regions of the sacrificial material exposed to the hydrogel; and/or (b) depositing the first and second polymer layers sandwiching an electrically conducting layer comprises: (i) depositing and patterning the first polymer layer onto the sacrificial layer; (ii) depositing and patterning the electrically conducting layer onto the first polymer layer; and (iii) depositing and patterning the second polymer layer onto the electrically conducting layer.

In certain implementations, (a) the first and second polymer layers are patterned via etching; and/or (b) the electrically conducting layer is patterned via ion milling; and/or (c) the first and second polymer layers comprise parylene-C.

In one aspect, the conformable neural interface system of the present disclosure may be used to stimulate or inhibit a nerve, tissue or ganglion in a subject in need thereof. The subject may suffer from a disease or medical condition that affects a system or an organ selected from the group consisting of heart, brain, lungs, an organ of a respiratory system, liver, kidney, stomach, small intestine, large intestine, a muscle of a limb, central nervous system, peripheral nervous system, pancreas, bladder, skin, urinary tract, thyroid gland, pituitary gland, and adrenal cortex.

In another aspect, the conformable neural interface system of the present disclosure may be used for modulating the levels of one or more hormones, neurotransmitters, immune cells, interleukins, cytokines, lymphokines, chemokines, growth factors, and/or enzymes in a subject.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

FIG. 1B is a nerve cross-sectional diagram showing the unique close position of the electrode pads in the device to the nerve fascicles. This position is distinct from traditional neural interface devices with recessed electrode pads and allows the electrode to be as close as possible to nerve fibers without traumatic piercing of the epineurium.

FIG. 2 is an illustrative flowchart for an example bioelectronic neural interface device manufacturing process in accordance with at least some embodiments of the present disclosure. The flowchart 200 details the following steps: (1) deposit sacrificial material onto substrate (202); (2) deposit and pattern first polymer layer (204); (3) deposit and pattern electrically conducting layer (206); (4) deposit second polymer layer (208) and pattern stack of first and second polymer layers; (5) deposit and pattern epoxy-based layer onto second polymer layer (210); (6) attach coverlay layer to contact pad region; (7) deposit first polydimethylsiloxane layer; (8) separate device from the substrate (216); and (9) deposit second polydimethylsiloxane layer on the other side of device.

FIG. 3A depicts polyacrylic acid (PAA) spin-coated, and a first layer of parylene-C deposited and patterned, with silicon substrate 302, sacrificial material 304, and a first polymer layer 306 identified. FIG. 3B depicts an electrically conducting layer of platinum (Pt) patterned by ion-milling, with silicon substrate 302, a first polymer layer 306, and a patterned electrically-conductive layer 310 identified. FIG. 3C depicts a second layer of parylene-C 320 deposited. FIG. 3D depicts patterned parylene-C and deposited and patterned SU-8 layer 330. FIG. 3E depicts hydrogel drop coated on the neural interface device, with silicon substrate 302, sacrificial material 304, sol state 340, and glass spacer 342 depicted. FIG. 3F depicts release of the neural interface device once the PAA has dissolved, with a patterned electrically-conductive layer 310, gel state 350, and resulting electrode geometry flush with the surface of the probe 360 identified.

FIGS. 4A and 4B correspond with an example probe fabricated on polyacrylic acid (PAA) in accordance with at least some embodiments of the present disclosure. FIG. 4A is man optical image of a probe fabricated on PAA, with bioelectronic interface device 400, parylene-C 402, Pt 404, PAA 406, and SU-8 408 identified. FIG. 4B is a representation of the probe of FIG. 4A, with bioelectronic interface device 400, pad region 420 and electrode contact region 430 identified.

FIG. 7A shows a poly(ethylene glycol)-dopamine ([PEG-Dopa]₄) hydrogel in the sol state poured over devices fabricated on PAA, with a device 700, electrode region 710, pad region 712, and glass substrate 702 identified. FIG. 7B shows the device after PAA is dissolved, with glass substrate 702 identified.

FIGS. 12A-12C provide various views illustrating surgical implantation of a bioelectronic neural interface device in accordance with at least some embodiments of the present disclosure. FIG. 12A shows a neural interface device 1202, cervical vagus nerve 1204, trachea 1206, carotid artery 1208, connector 1212, and probe 1212. The midline is represented by a dotted line and indicated by numeral 1210. The left cervical vagus is shown but the probe can be placed on the left or the right or on any distal or proximal branch of the vagus nerve. FIG. 12B shows the neural interface device 1202 and cervical vagus nerve 1204, depicted in FIG. 12B, with four electrode contacts illustrated. Electrodes can be configured for monopolar or bipolar simulation or recording. The electrode contacts are labeled "1," "2," "3," and "4," and each of the electrode contacts includes an "a" connection and a "b" connection. The connection between "a" and "b" is used to confirm electrode conductivity of the device. Finally, FIG. 12C depicts a rostral view illustrating a cross-section of the cervical vagus nerve 1204. Electrode contacts "1," "2," "3," and "4" are numbered arbitrarily in a crosswise manner.

Figures 13A, 13B:
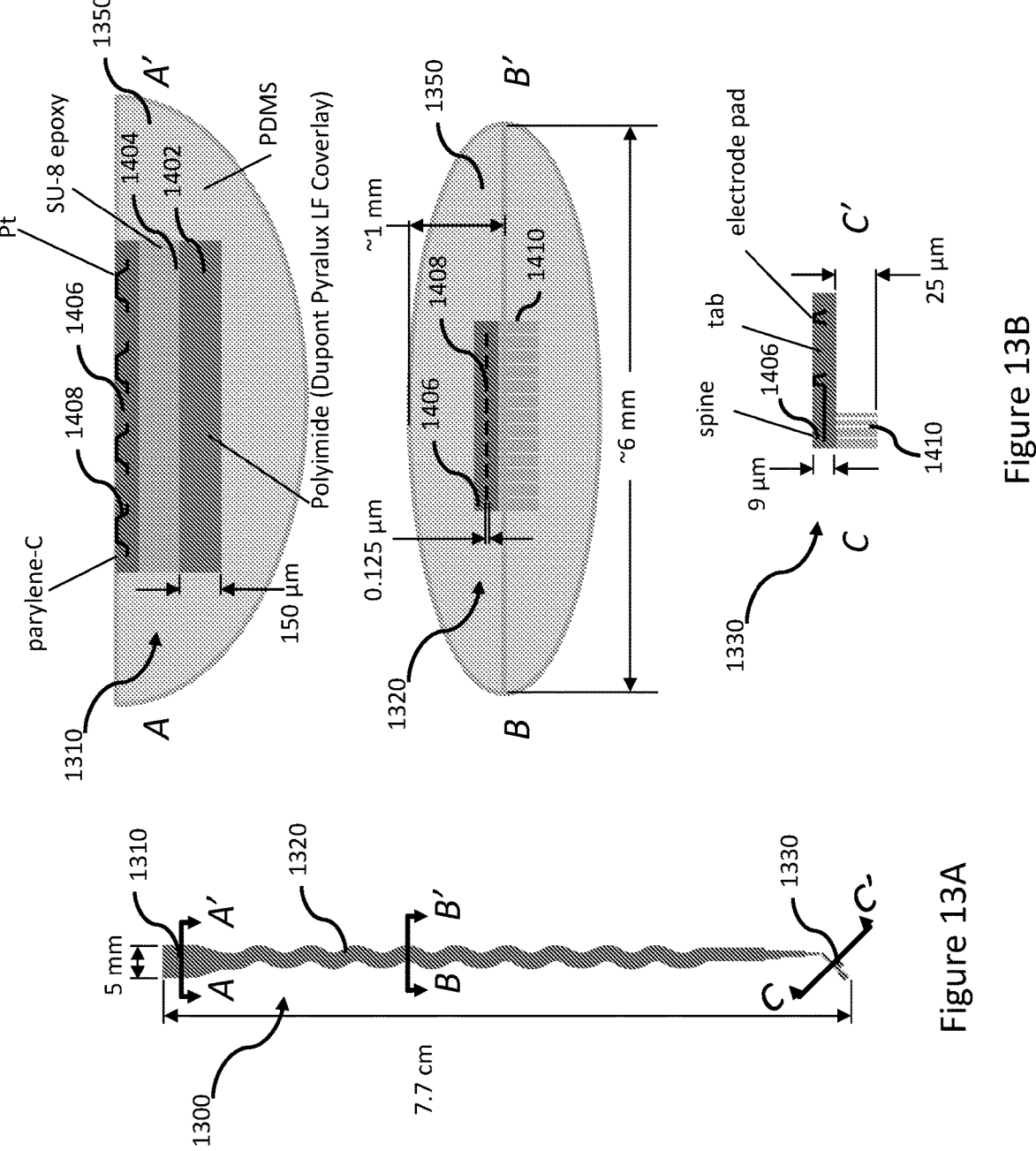
FIGS. 13A-13B provide an overview of the probe geometry and cross-sections through the cable connector region (A-A'), the cable region (B-B') and the electrode region.

14A-14H show example processing steps for fabricating the electrode region (C-C') of the neural interface device shown in FIG. 13A.

FIGS. 15A-15D show example processing steps for fabricating example neural interface devices in accordance with one or more example embodiments. In particular, FIGS. 15A-15D show example processing steps for fabricating the cable region (B-B') of the neural interface device shown in FIG. 13A.

FIG. 16 is an illustrative flowchart for an example bioelectronic neural interface device manufacturing process in accordance with at least some embodiments of the present disclosure. The flowchart 1600 details the following steps: (1) deposit sacrificial material onto substrate (1602); (2) deposit and pattern first polymer layer (1604); (3) deposit and pattern electrically conducting layer (1606); (4) deposit second polymer layer and pattern stack of first and second polymer layers (1608); (5) deposit and pattern epoxy-based layer onto second polymer layer (1610); (6) attach coverlay layer to contact pad region (1612); (7) deposit first polydimethylsiloxane layer (1614); (8) separate device from the substrate (1616); and (9) deposit second polydimethylsiloxane layer on the other side of device (1618).

Figures 17A, 17B, 17C:
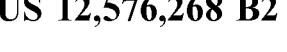

FIGS. 17A-C illustrate various cervical vagus probes of differing sizes configured to accommodate nerve diameters of 350 μm, 450 μm, and 500 μm.

Figures 18A, 18B, 18C:
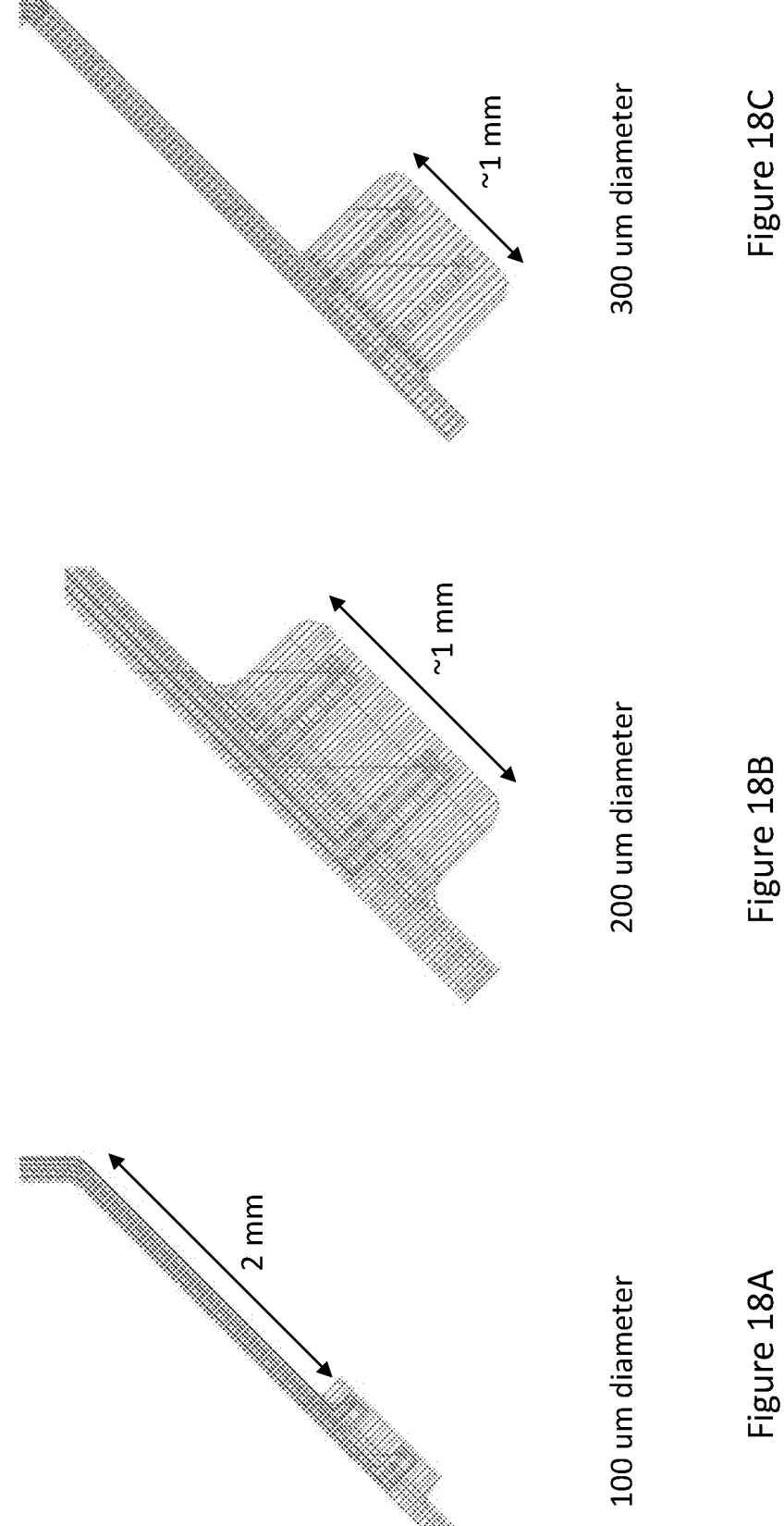

FIGS. 18A-C illustrate various abdominal vagus probes of differing sizes configured to accommodate nerve diameters of 100 μm, 200 μm, and 300 μm.

Figure 19:
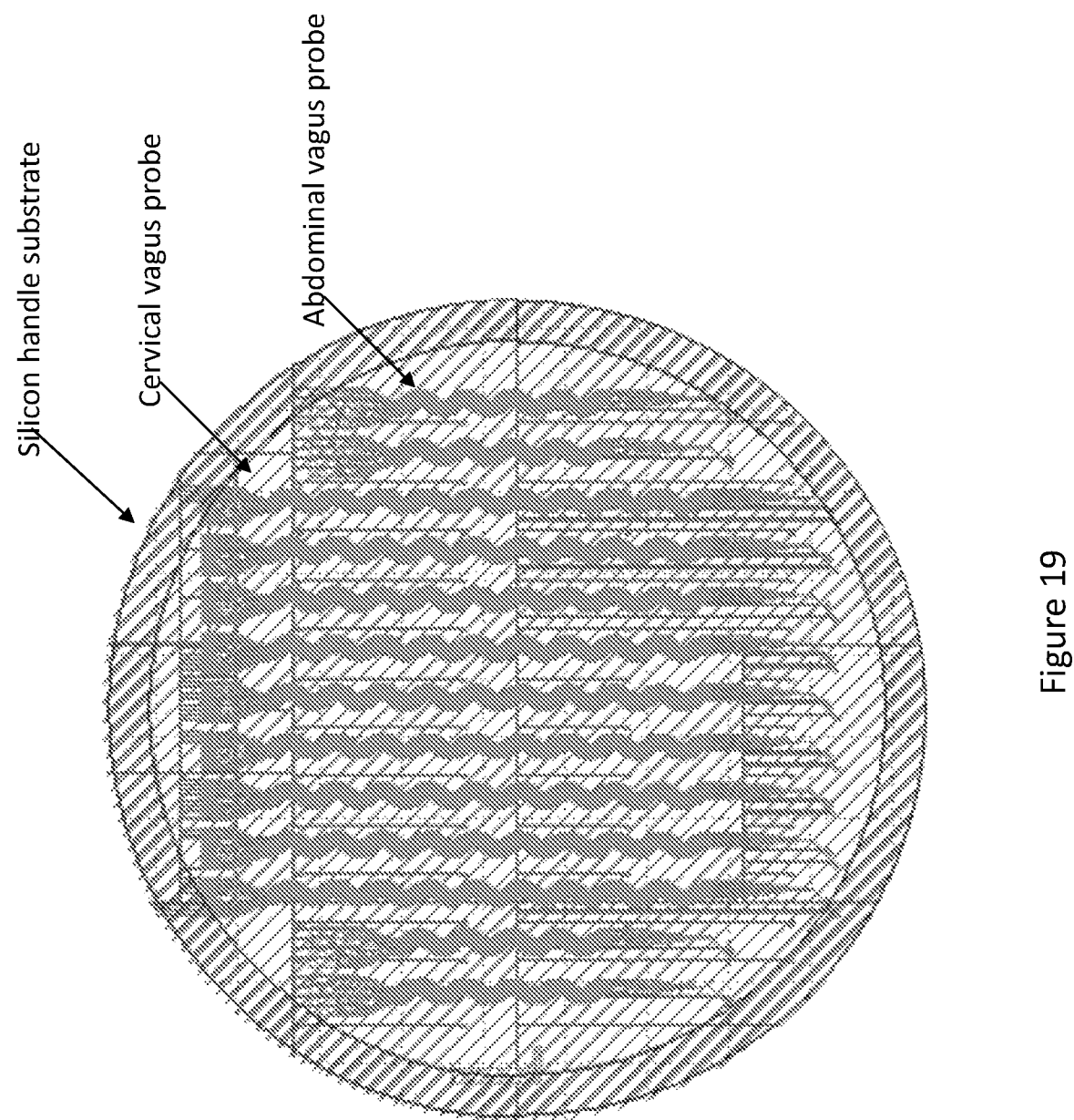

FIG. 19 illustrates a plan view of the wafer layout used to manufacture the probes of the nerve interface devices described herein.

FIGS. 20A-20E illustrates a ventral view of the sequence of events during a surgical procedure to attach the neural interface device to a nerve. (a) Hydrogel and probe are placed under the vagus nerve. (b) Probe is placed onto hydrogel. (c) Nerve is positioned on top of the probe. (d) Hydrogel is pulled around vagus and opposing halves of the hydrogel are stuck together. (Not shown: The second tab further down the nerve completes the circumferential electrode arrangement.)

FIG. 21 is an illustrative flowchart 2100 for an example method of securing the electrode pads and hydrogel to a nerve in accordance with at least some embodiments of the present disclosure. The flowchart depicts the following steps: (1) access a peripheral nerve or ganglia via a surgical procedure (2102); (2) identify a nerve, tissue, or ganglion location at which to secure a neural interface device (2104); (3) place the neural interface device on to the hydrogel layer (2106); (4) align the assembly of the neural interface device and hydrogel to the nerve, or ganglia (2108); (5) secure the neural interface device to the nerve, or ganglia by folding the hydrogel layer around the tissue location (2110); (6) remove the substrate holding the hydrogel (2112); and (7) close the surgical site (2114).

FIGS. 22A-22D illustrate a method of wrapping the vagus nerve with the conformable neural interface system. (1) The hydrogel, with probe on top, is positioned on surgical support substrate (such as Parafilm) and placed under the vagus nerve. (2) Nerve is positioned against the probe. (3) The hydrogel is pulled around the nerve. (4) The detachable surgical support substrate is removed, which leaves the hydrogel and probe in place.

Figure 23:

FIG. 23 is an image of a rat vagus nerve that has been completely wrapped by the conformable neural interface system of the present disclosure.

Figure 24:
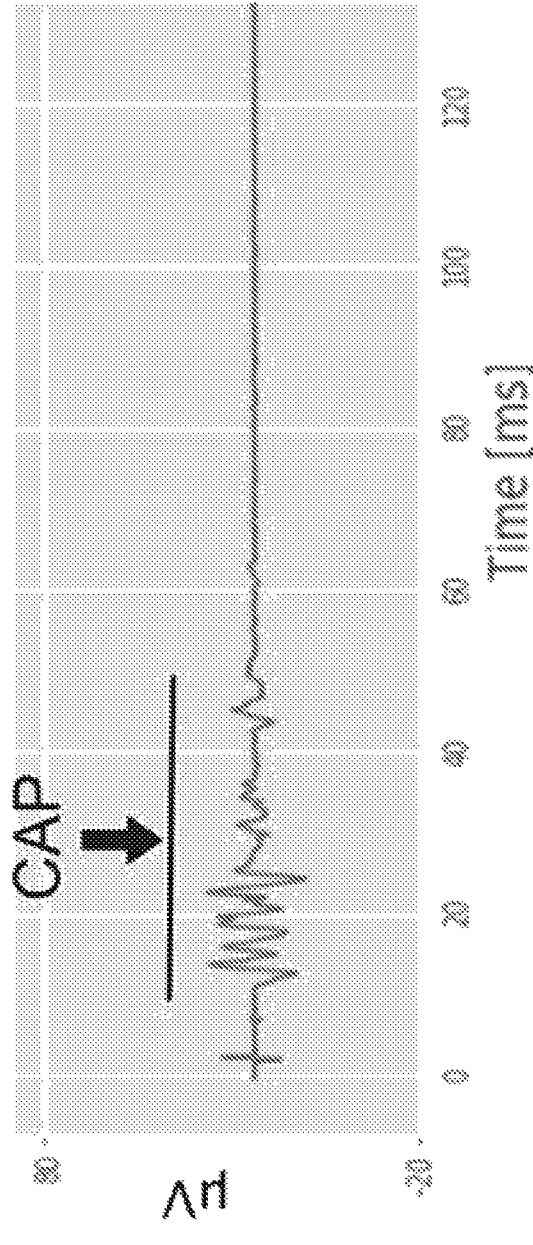

FIG. 24 is an exemplary recording from a vagus nerve stimulation test in rats. The vagus nerve was stimulated with the conformable neural interface system attached to the cervical vagus nerve and the compound action potential (CAP) was recorded from the abdominal vagus nerve using a platinum-iridium hook electrode.

FIG. 25 shows a scheme and image of the dorsal root ganglia (DRG).

The foregoing and other features of the present disclosure will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

I. Overview

In the following detailed description, reference is made to the accompanying drawings, which form a part of the disclosure. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, may be arranged, substituted, combined, and designed in a wide variety of different configurations, all of which are explicitly contemplated and make part of this disclosure.

Conventional "cuff" electrodes or flat planar devices are usually composed of materials that exhibit flexible rigidities between about $10^{-3}$ and about $10^{-2}$ Pa m$^3$ for films about ~100 μm in thickness. However, excitable tissues in the central and peripheral nervous systems with millimetric-scale thicknesses have estimated flexural rigidities of about $10^{-7}$-about $10^{-5}$ Pa m$^3$. Moreover, the surfaces of such nerve targets is quite limited as compared to other larger targets (e.g., organs), thus making it challenging to achieve good electrical and mechanical contact with nerve tissue. Indeed, it is usually necessary to apply compressive force when using existing cuff electrodes, which can damage the nerve or the blood supply to the nerve. Further, cuff electrodes exhibit low adhesion to target neural tissue because anchorage generally occurs as a result of scar tissue formation, which takes about 1 month to develop. The intrinsic mechanical mismatch at the tissue-device interface, relatively high rigidity of many existing probes, and micromotion due to poor adhesion to target neural tissue can damage organs, induce inflammation, alter local anatomy, and compromise device performance. Thus, existing "cuff" electrodes are ill-suited for neural interfaces on account of their mechanical properties and inability to conform to the anatomy of neural tissue.

In contrast, the conformable neural interface systems disclosed herein offer many advantages when integrating electrodes with tissue targets in nerves, muscle, cardiac cells, and the like. The conformable neural interface systems exhibit ultracompliant mechanical properties that are compatible with those of excitable tissue in the CNS and peripheral nervous systems. The suture-like anchoring device disclosed herein increases adhesion and electrical contact between a neural probe and the surface of a target tissue, thus improving signal transduction between the neural interface and the target tissue. The suture-like anchoring device of the present disclosure permits the integration of flexible electrodes with extremely fine structures such as ultrafine nerve fibers in the distal peripheral nervous system. Accordingly, unlike existing neural interface systems which require multiple invasive surgical intervention steps and exhibit poor adhesion to target tissue (e.g, nerve, ganglion, or other tissue), the conformable neural interface systems disclosed herein permit non-invasive yet sensitive detection or modulation of bioelectric signals in a target tissue (e.g., a peripheral nerve) immediately after implantation. The conformable neural interface systems of the present technology also exhibit reduced impedance as compared to other interface systems that have been fabricated on inorganic substrate counterparts.

The present document provides, inter alia, details for example bioelectronic conformable neural interface systems, example methods of manufacturing bioelectronic conformable neural interface systems and probes thereof, example methods of attaching bioelectronic conformable neural interface systems and probes thereof to nerves, and method of using the same for treatment of various diseases and conditions.

In various embodiments, methods of fabricating bioelectronic conformable neural interface systems including a sticky hydrogel are disclosed. In various implementations, the electrodes of the neural interface devices when adhered with hydrogel are significantly more compliant, as compared to existing cuff electrodes made of polyimide or polydimethylsiloxane (PDMS) that wrap around the nerve and create pressure, and include adhesion-promoting functional groups that facilitate enhanced electrical contact with the nerve, ganglion or tissue without the need for continuous application of pressure on the nerve, tissue or ganglion. This is highly advantageous, as continuous application of pressure on the nerve, tissue or ganglion can result in tissue damage and side effects. In addition, a more compliant neural interface device is easier to surgically place on the nerve, for example, the hydrogel folding process illustrated in FIG. 12 provides gentle non-traumatic sizing of the probe on the nerve, tissue or ganglion without the typically ill-fitting fixed sizes of rigid cuff electrodes.

In certain implementations, a transfer process is used to fabricate the bioelectronic conformable neural interface device using a sacrificial material that has tunable solubility in aqueous media. An example of such a material is polyacrylic acid (PAA), although other sacrificial materials are described herein. This can help avoid the need for harsh release chemicals that may affect the properties of the hydrogel.

The transfer process can also allow for electrode contacts that are flush with the surface (or in some embodiments, protruding outwardly from the surface) of the neural interface device and facilitate a more intimate/direct contact with the nerve, as compared with recessed electrode contacts which are common with prior neural interface devices. In some implementations, a patterned epoxy layer (having, e.g., an epoxy-based photo-patternable material such as SU-8) may provide a gradual change in Young's modulus from the stiff pad region to the compliant electrode contact region. In some implementations, polydimethylsiloxane (PDMS) layers cast onto both sides of the device cabling that connect the electrode region to the contact pad region provide further stiffening of the cabling for robust handling in surgery.

Thus, in one embodiment of the invention, the electrode contact region is relatively more compliant than the relatively stiffer contact pad region. The difference in compliance between the two regions can be, for example, about 5%, about 10%, about 15%, about 20%, about 25%, about 30%, about 35%, about 40%, about 45%, about 50%, about 55%, about 60%, about 65%, about 70%, about 75%, about 85%, about 90%, about 95%, or about 100%.

A primary trade-off between intrafascicular electrodes and extraneural electrodes is the degree of invasiveness and the spatial selectivity of the recording or stimulation, since selectivity is dependent on the proximity of the electrode contacts to the site of interest. Disclosed are example hydrogel-attached extraneural electrodes that are separated from the fascicle (which is the recording or stimulation site of interest) by the epineurium and perineurium. In various embodiments, selectivity of neural interface devices is improved in part by increasing the number of electrode contacts. In certain implementations, a higher number and/or density of electrode contacts can be achieved using microfabrication technology. In certain embodiments, the neural interface device can include at least two electrode contacts. In certain embodiments, the neural interface device can include two or more contacts placed circumferentially around the nerve, tissue or ganglion. Additionally, each row of circumferential electrode contacts can be spaced apart and positioned longitudinally along the neural interface device to increase response selectivity. Providing additional electrode contacts can increase the granularity at which the nerve can be stimulated or recorded by providing different stimulation or recorded signals to the electrode contacts. This functional selectivity is dependent on the number and size of functionally different fascicles within each nerve, for example, the application of the neural interface device with multiple electrode contacts on the cervical vagus would be expected to provide neuromodulation capabilities for the cardiac, pulmonary, and gastrointestinal systems because of the nerve fiber content of this nerve as compared to the more restricted motor and sensory functions of spinal nerves.

The present disclosure describes various neural interface devices that rely on the use of a hydrogel to improve the adherence of the neural interface device to a target tissue. The first neural interface device corresponds to a conformable neural interface device manufactured with an integrated adhesive hydrogel layer in accordance with the process described in FIGS. 2 and 3A-3F in which the neural interface device is attached to a hydrogel layer during the fabrication process of the neural interface device as described in FIGS. 3A-3F. The second neural interface device corresponds to a conformable neural interface device that is manufactured in accordance with the process described in FIGS. 14A-14H and 15A-15D and subsequently placed on a suture-like anchor device after fabrication of the neural interface device and prior to surgically implanting the neural interface device within a subject.

Figure 1A:
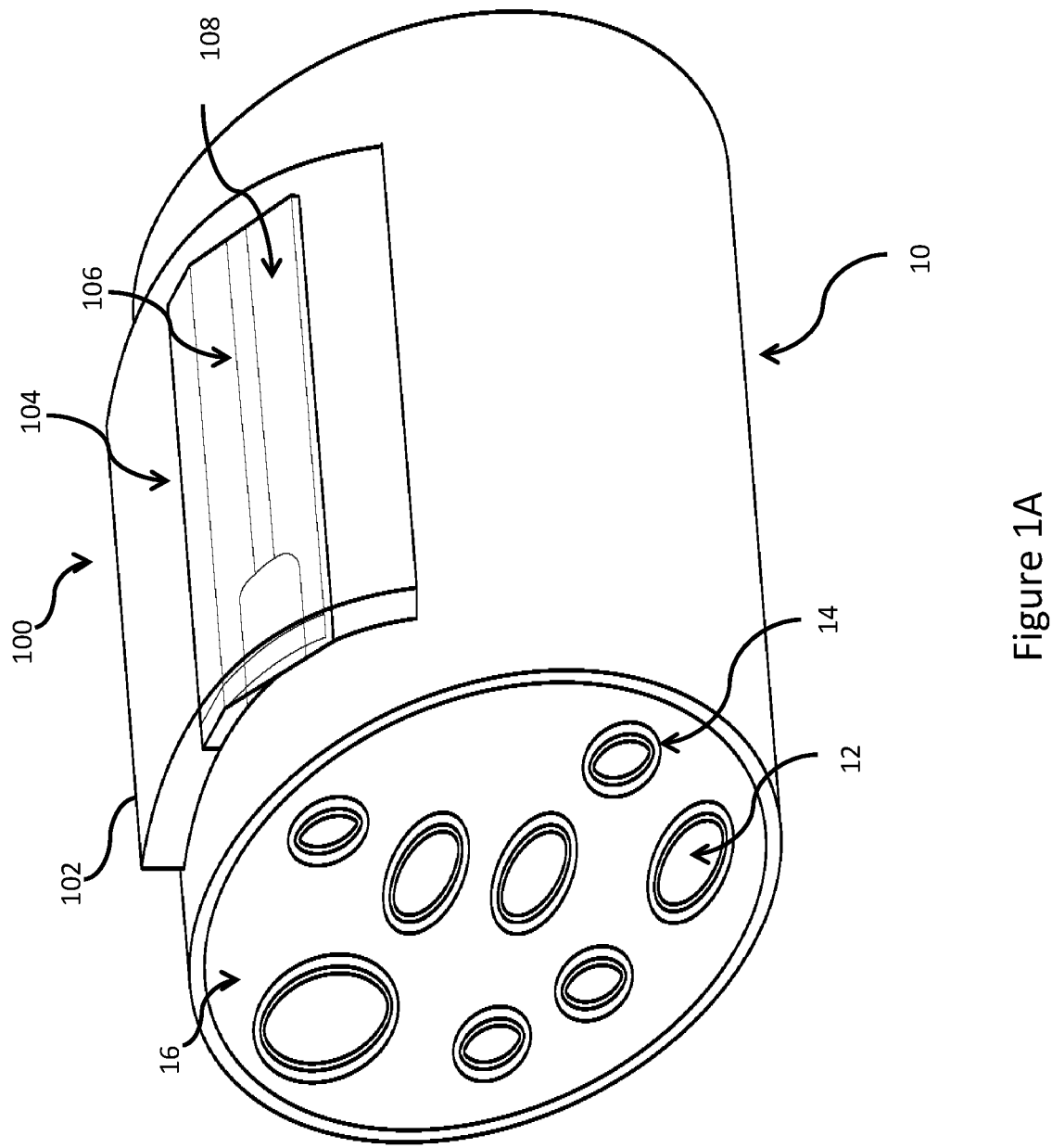
FIGS. 1A and 1B illustrate an example bioelectronic neural interface system 100 placed on a nerve 10 in accordance with at least some embodiments of the present disclosure. The nerve 10 includes nerve fascicles, such as 12, each surrounded by a perineurium 14. A number of sheathed fascicles 12, may be bundled within an epineurium 16. Aspects of the bioelectronic neural interface system 100 depicted in FIG. 1A include "sticky" hydrogel region 102 and a probe region 104 having an electrically conducting member 106 at least partially embedded in one or more polymer layers 108.
Figure 1B:
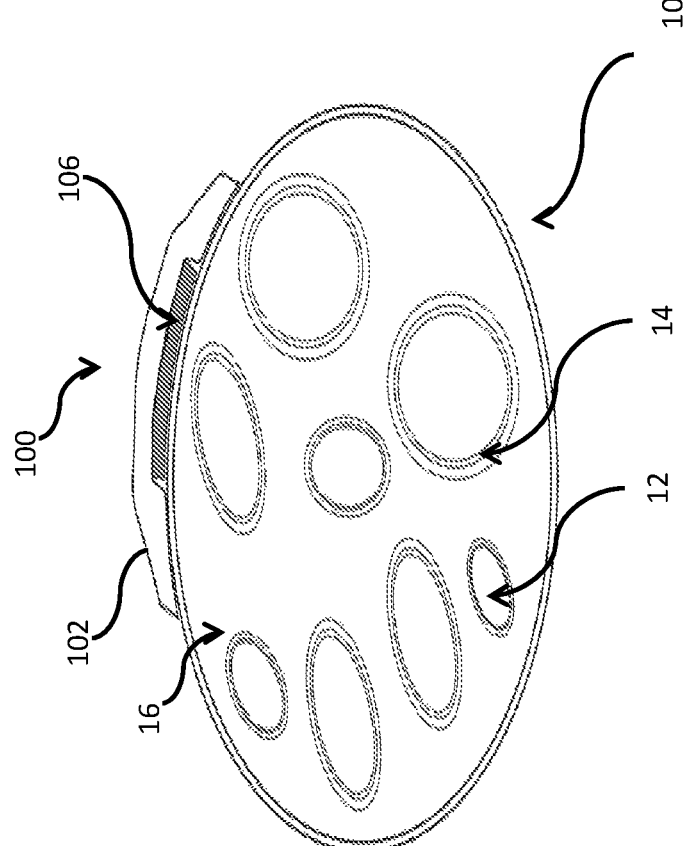

II. Conformable Neural Interface Device Manufactured with an Integrated Adhesive Hydrogel Layer Referring to FIGS. 1A and 1i, an example bioelectronic neural interface system 100 secured to a nerve 10 is depicted. The nerve 10 includes nerve fascicles 12, with bundles of nerve fibers (axons), each surrounded by a protective sheath known as the perineurium 14. A number of sheathed fascicles 12 may be bundled within another sheath known as the epineurium 16. The neural interface system 100 can comprise a neural interface device that can be attached to a nerve via an adhesive hydrogel structure. In some embodiments, the adhesive hydrogel structure is integrated with the neural interface device, which can include one or more polymer layers, an electrically conducting layer, optionally an epoxy-based layer, and one or more PDMS outer layers. As shown in FIGS. 1A and 1, the neural interface device forms the neural interface system 100. FIG. 1B is a nerve cross-sectional diagram showing the unique close position of the electrode pads in the neural interface device to the nerve fascicles. This position is distinct from traditional neural interface devices with recessed electrode pads and allows the electrode of the neural interface device to be as close as possible to nerve fibers without traumatic invasive implant.

Polymer Layer

As shown in FIGS. 1A and 1B, a "sticky" hydrogel region 102 helps secure the bioelectronic neural interface system to nerve 10. The bioelectronic neural interface system includes a probe region 104 having an electrically conducting member or layer 106 at least partially embedded in one or more electrically insulating polymer layers 108 (comprising, e.g., parylene-c). Any suitable pharmaceutically acceptable polymer may be utilized in the methods and devices of the invention, as long as the polymer is electrically insulating and also amenable to deposition and patterning with thin-film microfabrication techniques. Examples of other useful polymers include, for example, polymers with a relatively low dielectric constant, for example fluorinated polymers, e.g., Teflon; aryl and/or heteroaryl containing polymers, e.g., a polystyrene or a parylene; and silicon containing polymers, e.g., polysilsesquioxane. Polyimides may also serve as the insulating layers. The polymer layer may serve, in various embodiments, as a moisture barrier and/or as a dielectric barrier. Other variants may include additional moisture barriers between the electronically conducting layer and the polymer layers (e.g., silicon carbide, oxides, and ceramic materials).

Parylene is the generic name for a variety of chemical vapor deposited poly(p-xylylene) polymers used as moisture and dielectric barriers. These members (or variations of Parylene) each offer their own, slightly different, coating properties to engineers. Commercially available Parylene variants include Parylene N (poly(para-xylylene or [2.2] paracyclophane), Parylene C (Dichloro[2,2]paracyclophane), Parylene D, Parylene AF-4 and Parylene VT-4. Among them, Parylene C is the most popular due to its combination of barrier properties, cost, and other processing advantages. Parylene C and to a lesser extent AF-4, SF, HT are used for coating printed circuit boards (PCBs) and medical devices. There are numerous other applications as parylene is an excellent moisture barrier. It is the most bio-accepted coating for stents, defibrillators, pacemakers and other devices permanently implanted into the body.

The one or more polymer layers can have a thickness of, for example, about 50 nm, about 75 nm, about 100 nm, about 125 nm, about 150 nm, about 175 nm, about 200 nm, about 225 nm, about 250 nm, about 275 nm, about 300 nm, about 325 nm, about 350 nm, about 400 nm, about 500 nm, about 800 nm, about 1 μm, about 2 μm, about 3 μm, about 4 μm, about 5 μm, or about 10 μm. In an exemplary embodiment, the one or more polymer layers each have a thickness of about 4.5 μm, and in the case of two polymer layers sandwiched around the conductive layer, the total thickness at the electrode region located next to the nerve is approximately 9 μm.

Probe

As further discussed below, probe region 104 may include, in various implementations, an electrode contact region having electrode contacts that are flush with nerve 10 to enhance the ability of the bioelectronic neural interface system 100 to interface (i.e., communicatively or electrically couple so as to be able to sense and/or deliver electrical signals) with the nerve 10 (see, e.g., FIG. 3F and corresponding discussion). FIG. 1B shows a cross sectional view of the neural interface system 100 attached to the nerve 10. As shown in FIG. 1B, the electrode is substantially flush with the bottom surface of the neural interface system 100 and in contact with the nerve 10. Multiple electrode contacts positioned about a nerve can be seen in FIGS. 12B and 12C, also discussed below.

Advantageously, a bioelectronic neural interface device, such as the bioelectronic neural interface system 100, which does not include electrodes that penetrate the fascicles 12, is non-invasive relative to devices with electrodes that are intrafascicular.

In one aspect of the invention, the bioelectronic neural interface device can be fabricated in an inverted manner with the electrode contacts facing down (as compared to existing processes where the insulation is first deposited prior to etching of the electrode contacts). As a result, the surface of the electrode contact is not exposed to oxygen reactive-ion etching (RIE) that otherwise would oxidize the surface of the electrically conducting layer and deteriorate electrode performance. Furthermore, the resulting electrode geometry is substantially flush with the surface of the probe (see numeral 360 in FIG. 3F), in contrast with existing neural interface device that have recessed electrodes. The flush electrodes facilitate intimate contact with the nerve.

Electrically Conducting Layer

The electrically conducting layer may include any combination of metals or other materials that allow the flow of electrical current deemed suitable. An example of electrically-conducting metal includes but is not limited to platinum (Pt). In various embodiments, the metals or other materials are selected based on their biological inertness so that they are unlikely to initiate or otherwise result in an undesired biological or chemical response when in contact with nerves or other biological tissue. Examples of other biologically compatible conductive materials include metals and polymers. Suitable metals include, for example, platinum, platinum/iridium, gold, and titanium. Electrically conducting polymers may be placed at the electrode site. Suitable polymers include, for example, polypyrrole, polyaniline, poly (3,4-ethylenedioxythiophene), poly(3-hexylthiophene), polythiophene, poly(3-octylthiophnene-3-methyl-thiophene), poly(p-phenylene-terephthalamide), polythiophene-vinylene, poly(3-alkylthiophene), poly(p-phenylene), poly-p-phenylene-sulphide, polybutadiene, poly(p-phenylenevinylene), poly(p-phenylene-terephthalamide), polyacetylene, polyfuran, polyisoprene, polyazulene, poly(isothianaphthene), and poly(α-naphthylamine).

The electrically conducting layer can have a thickness of, for example, about 150, about 175, about 200, about 225, about 250, about 275, about 300, about 325, about 350, about 375, about 400, or about 425 nm. In an exemplary embodiment, the electrically conducting layer can has a thickness of about 250 nm.

Epoxy-Based Layer

In certain embodiments, the neural interface device may additionally comprise an epoxy-based layer, which is preferably deposited onto the polymer layer. In certain embodiments, the epoxy-based layer may include an epoxy-based photo-patternable material, such as an epoxy-based photoresist. In certain implementations, the epoxy-based layer may include an epoxy-based negative photoresist such as SU-8 (MicroChem). SU-8 is a commonly used epoxy-based negative photoresist. Negative refers to a photoresist whereby the parts exposed to ultraviolet (UV) light become cross-linked, while the remainder of the film remains soluble and can be washed away during development. In some implementations, portions of the epoxy-based layer, when exposed to ultraviolet or other light, become cross-linked, while unexposed portions remain soluble and may be washed away in a subsequent step. Any pharmaceutically acceptable epoxy can be utilized in this aspect of the invention. Examples of other useful epoxy-based compounds include, for example, HARE-SQ (KemLab), and generally any polymer with a crosslinkable epoxide side group that can be photo-patterned.

The epoxy-based layer, which is preferably photo-patternable, can have a thickness of, for example, about 5, about 10, about 15, about 20, about 25, about 30, about 35, or about 40 μm. In an exemplary embodiment, the epoxy-based layer has a thickness of about 25 μm.

Because abrupt changes in stiffness creates stress concentrators that can lead to damage when stress is applied during handling, the photo-patternable material such as SU-8 may, in various embodiments, be patterned to impart a gradual transition in stiffness from the flexible electrode region to the stiff pad region by varying the volume ratio of the photo-patternable material such as SU-8 to hydrogel using patterned pores with varying density.

Figure 4A:
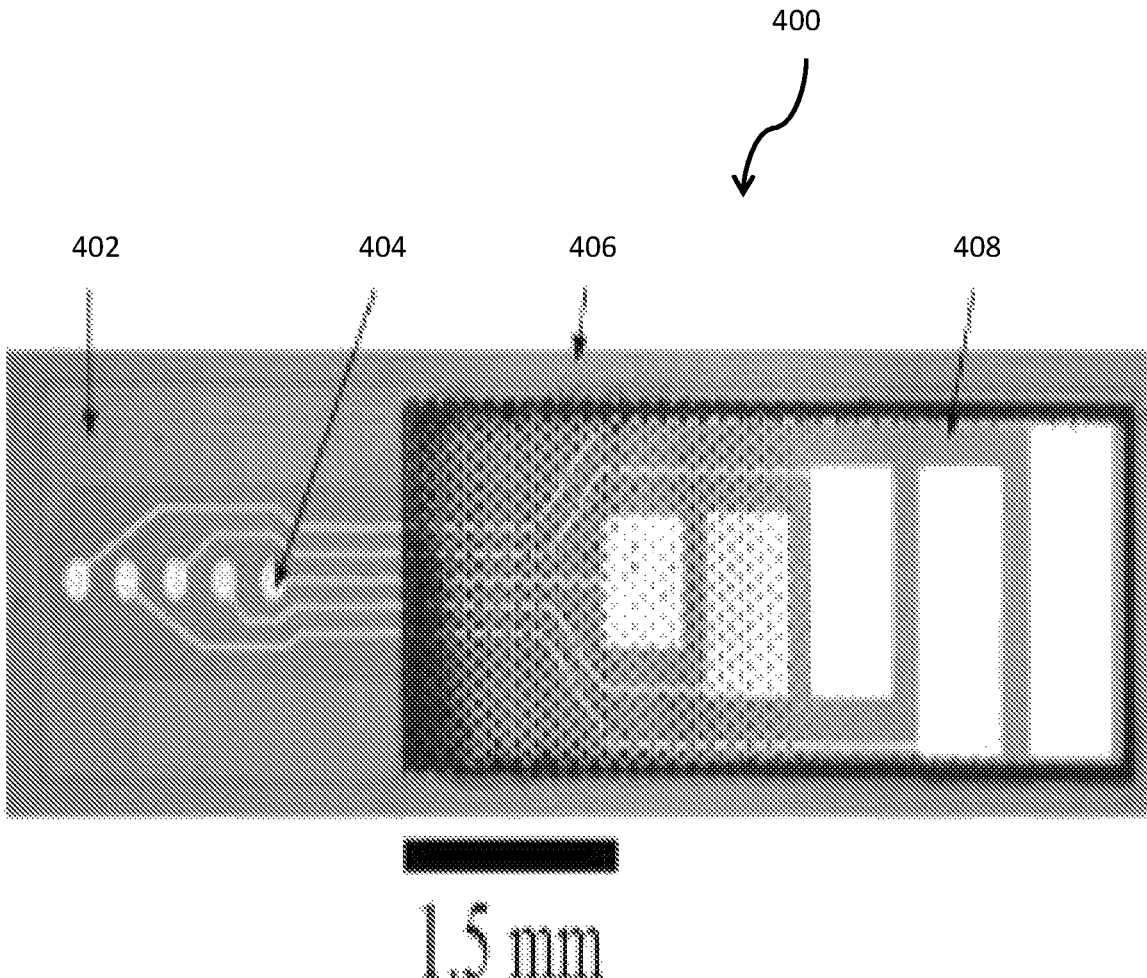

As shown in FIGS. 4A and 4B, in certain implementations of bioelectronic interface device 400, the density of the pores may start from substantially all SU-8 with no pores (i.e., 0% pore density) at the pad region 420 (which interfaces with an external connector) and may be gradually increased until there is no SU-8 (i.e., 100% pore density) in the electrode contact region 430 (which interfaces with the nerve) of the device. In other embodiments, the density of the pores may start from about 0%, about 5%, about 10%, about 15%, about 20%, about 25%, about 30%, about 35%, about 40%, about 45%, or about 50%, and gradually increase until the pore density is about 55%, about 60%, about 65%, about 70%, or about 75%. In FIG. 4A, numeral 402 references parylene-C, numeral 404 references Pt, numeral 406 references PAA, and numeral 408 references SU-8.

Silicone-Based Layer

In certain embodiments, the neural interface device may additionally comprise silicone-based layers, which are preferably deposited onto the epoxy-based layer on one side of the device and onto the polymer layer (parylene-C) on the other side of the device. Any pharmaceutically acceptable silicone encapsulant can be utilized in this aspect of the invention. In an exemplary embodiment, the silicone is polydimethylsiloxane (PDMS) and specifically Sylgard 184 (Dow Corning) silicone elastomer encapsulant.

The silicone-based layers can have a gradient in thickness that ranges from zero thickness near the electrode region of the device to a maximum thickness at the contact pad region of the device. The silicone-based layer on each side can have a maximum thickness of of, for example, about 0.5 mm, about 1 mm, about 1.5 mm, about 2 mm, about 2.5 mm, or about 3 mm. In an exemplary embodiment, the silicone-based layer on each side has a maximum thickness of about 1.5 mm.

21

Hydrogel Layer

In certain implementations, the hydrogel layer may be, or may include, polyethylene glycol (PEG). Examples of other useful hydrogels include, but are not limited to, various polymers crosslinked to form hydrogels. Examples include crosslinked polymers of poly(ethylene oxide), poly(ethylene glycol-co-propylene glycol), poly(vinyl pyrrolidinone), poly (vinyl alcohol), acrylic polymers, and methacrylic polymers. Examples of synthetically prepared monomers that may be crosslinked to form these hydrogels include ethylenically unsaturated hydrocarbons such as acrylic monomers and methacrylic monomers.

Figures 3A, 3B, 3C, 3D, 3E, 3F:
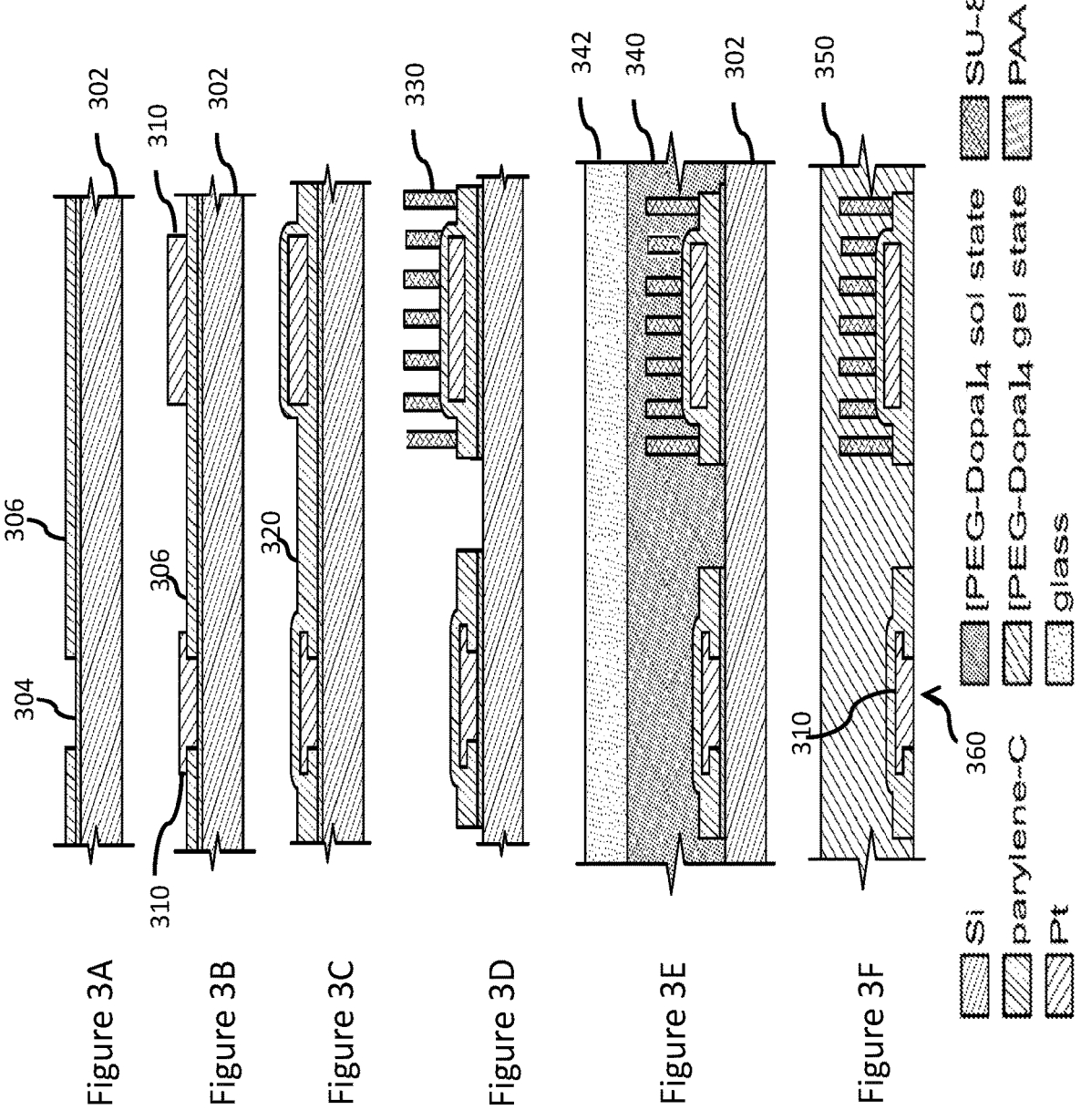
FIGS. 3A-3F represent example processing steps for fabricating example neural interface devices in accordance with one or more example embodiments.

The hydrogel layer may, in various implementations, have a thickness of, for example, about 1 to about 2 millimeters (mm) as measured from the bottom of spacer 342 in FIG. 3E to the top of the sacrificial layer 304 or to the top of the substrate 302.

In some embodiments, the adhesive hydrogel layer can have a thickness selected from the group consisting of about 0.25 mm, about 0.5 mm, about 0.75 mm, about 1 mm, about 1.25 mm, about 1.5 mm, about 1.75 mm, about 2 mm, about 2.25 mm, about 2.5 mm, about 2.75 mm, about 3 mm, about 3.25 mm, and about 3.5 mm.

In certain implementations, the hydrogel may be synthesized separately as a stimulus-responsive telechelic Dopa-modified polyethylene glycol-based hydrogel. For example, $Fe^{3+}$-[PEG-Dopa]$_4$ hydrogels may be formed through $Fe^{3+}$-induced cross-linking of four-arm polyethylene glycol-dopamine precursors to produce networks. The relative amounts of H-bonds, coordination bonds, and covalent bonds can be controlled by the [$Fe^{3+}$]:[Dopa] molar ratio in precursor solutions. Sustained ultrasonic energy may stabilize hydrogels through the formation of additional cross-links via free radical-mediated coupling of pendant catechols.

In various embodiments, the hydrogel includes $H^+$ ions that dissolve the PAA, releasing the device after a certain time (e.g., about 2 hours or less). At the same time, gelation of the hydrogel occurs, represented as hydrogel in the gel state 350 in FIG. 3F. The hydrogel, with the attached device, may then be removed from the glass or silicon substrate 302.

III. Methods of Manufacturing the Conformable Neural Interface Device Including the Adhesive Hydrogel Layer Referring to FIG. 2, an example method 200 for manufacturing a bioelectronic neural interface device is provided. More specific details of particular implementations of method 200 are provided below in the context of the discussion of FIGS. 3A-3F, below. In particular, FIG. 2 depicts a flowchart 200 for an example electrode manufacturing process in accordance with at least some embodiments of the present disclosure. The flowchart 200 details the following steps: (1) deposit sacrificial material onto substrate (202); (2) deposit and pattern first polymer layer (204); (3) deposit and pattern electrically conducting layer (206); (4) deposit second polymer layer (208) and pattern stack of first and second polymer layers; (5) deposit epoxy-based layer onto second polymer layer (210); (6) deposit hydrogel in sol state (212); (7) allow hydrogel to gelate and sacrificial layer to transform (214); and (8) separate device from the substrate (216).

Method 200 focuses on the layers and materials that may be added in the example manufacturing process. Once each material/layer is deposited or otherwise applied, the material/layer may be "patterned" to yield desired structural characteristics. Patterning may be accomplished in various ways deemed suitable to achieve a desired product in an effective manner. Examples of patterning steps are also discussed below in the context of FIGS. 3A-3F.

At process step 202, a sacrificial material is deposited onto a substrate. The sacrificial material may be deposited as part of a layer that includes at least a portion or region that is temporary or is otherwise subsequently changed, structurally or compositionally, in the manufacturing process. A substrate may be a solid (often planar) substance, such as a semiconductor or an insulator like glass, which serves as a foundation onto which another substance may be applied. Example substrates include but are not limited to thin slices or wafers of material such as silicon, silicon dioxide, glass, quartz, aluminum oxide, sapphire, germanium, gallium arsenide (GaAs), an alloy of silicon and germanium, indium phosphide (InP), etc.

The sacrificial material layer can have a thickness of, for example, about 200, about 225, about 250, about 275, about 300, about 325, about 350, about 375, about 400, about 425 nm, about 450, about 475, about 500, about 525, about 550, about 575, about 600, about 625, about 650, about 675, about 700, about 725, about 750, about 775, or about 800 nm. In an exemplary embodiment, the sacrificial material layer can has a thickness of about 700 nm.

The sacrificial material, in various embodiments, has a manipulatable, modifiable, transformational, or otherwise "tunable" characteristic or property, such as a tunable solubility in aqueous media. For example, the sacrificial material may have a first solubility in a first state and a second solubility in a second state. In certain implementations, the sacrificial material may be relatively insoluble when first deposited, under a first set of conditions (e.g., in a certain pH, temperature, etc.), and/or when in contact with certain materials, and may be relatively soluble after a certain time, under a second set of conditions, and/or when in contact with certain other materials. In some embodiments, the sacrificial material may not be soluble in typical organic solvents such as acetone, isopropyl alcohol, ethanol and hexane since these solvents can be used in the device fabrication.

At process step 204, a first polymer layer may be deposited onto the sacrificial material. The polymer layer may serve, in various embodiments, as a moisture barrier and/or as a dielectric barrier. In certain implementations, the first polymer layer may be, partially or entirely, a poly(p-xylylene) polymer such as a parylene. In some implementations, the polymer may be parylene-C. Other useful polymers are described herein.

At process step 206, an electrically conducting layer may be deposited. The electrically conducting layer may include any combination of metals or other materials that allow the flow of electrical current deemed suitable. An example of electrically-conducting metal includes but is not limited to platinum (Pt).

At process step 208, a second polymer layer may be deposited onto the electrically conducting layer. Like the first polymer layer, the second polymer layer may also be, partially or entirely, a poly(p-xylylene) polymer such as a parylene, including for example parylene-C. Other useful polymers are described herein.

At process step 210, an epoxy-based layer may be deposited onto the second polymer layer. In certain embodiments, the epoxy-based layer may include an epoxy-based photo-patternable material, such as an epoxy-based photoresist. In certain implementations, the epoxy-based layer may include an epoxy-based negative photoresist such as SU-8. In some implementations, portions of the epoxy-based layer, when exposed to ultraviolet or other light, become cross-linked, while unexposed portions remain soluble and may be washed away in a subsequent step. Any pharmaceutically acceptable epoxy can be utilized in this aspect of the invention.

By fabricating electrode contacts that are substantially flush with the surface of the probe (i.e., not significantly recessed), enhanced electrical contact with the nerve can be achieved. In various embodiments, a substantially flush electrode contact has no measurable distance from the surface of the probe and the surface of the electrode contact (i.e., zero recess).

In certain implementations, a substantially flush electrode contact has a separation of no more than about 5 nanometers (nm) from the surface of the probe and the surface of the electrode contact (i.e., a recess of about 5, about 4, about 3, about 2, or about 1 nm or less). In some implementations, a substantially flush electrode contact has a separation of no more than about 25 nm from the surface of the probe and the surface of the electrode contact (i.e., a recess of about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, about 2, or about 1 nm or less). In other embodiments of the invention, a substantially flush electrode contact has a separation of no more than about 10, about 15, or about 20 nm from the surface of the probe and the surface of the electrode contact (i.e., a recess of about 10, about 15, or about 20 nm or less). In alternative embodiments, the electrode contacts may be configured to protrude or extend out (e.g., about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24 or about 25 nm) from the surface of the probe.

In various embodiments, the device is immersed in water to dissolve the sacrificial material (e.g., PAA), releasing the device after a certain time (e.g., about 2 hours or less). In other embodiments of the invention, the device is released after about 15 mins, about 30 mins, about 45 mins, about 1 hr, about 1.5 hrs, about 2 hrs, about 2.5 hrs, about 3 hrs, about 3.5 hrs, or about 4 hrs. The optional presence of silicone-based layers may result in wider cabling as part of the device and thus require a longer time to release the device from its substrate (e.g., 20 hrs). The attached device may then be removed from the glass or silicon substrate 302.

In various embodiments, PAA may be selected as the sacrificial layer material because it has tunable solubility in water and thus may help ensure that the hydrogel does not need to contact the sort of relatively harsher chemicals used in existing fabrication steps. Other examples of sacrificial materials with tunable solubility include block-copolymers of PAA with a non-acrylic acid monomer, e.g., poly(styrene)-block-poly(acrylic acid); polyacrylamide polymers, e.g., poly(acrylamide-co-acrylic acid), poly(N-alkylacrylamide-co-acrylic acid) polymers; a poly(alkylene-co-acrylic acid) polymer; and generally a polymer with a side group(s) containing any ionizable moiety. Non-limiting examples of such ionizable moieties include carboxylic acid, hydroxyl, amide, sulfonamide, phosphate, sulfate, sulfonate, sulfinate, amine, thiol, imide, oxime, peroxide, carbamate, guanidine, hydrazine, hydrazide, hydrazine, hydroxamic acid, and hydroxamic amidine. In various embodiments, PAA is used as sacrificial material for its stability in typical organic solvents, such as alcohols, acetone, isopropyl alcohol, ethanol, and hexane used in the device fabrication. In an exemplary embodiment, the sacrificial material is PAA, which is insoluble in water when treated with bivalent ions such as $Ca^{2+}$. At the transfer process step, the PAA is treated first with NaCl solution to reverse its water solubility property. The $Na^+$ displaces the $Ca^{2+}$ and makes the PAA soluble in water. Immersion in water of the device on the substrate eventually dissolves the PAA sacrificial material and releases the device from the substrate.

In example embodiments, the dopamine groups in this hydrogel may have adhesive properties and may, in some implementations, be found in mussels. See e.g., Ding et al., "Mussel-inspired polydopamine (PDA) for bio-surface functionalization," *Biosurface and Biotribology*, 2(4): 121-136 (2016); and P. Forooshane and B. Lee, "Recent approaches in designing bioadhesive materials inspired by mussel adhesive protein," *Polymer Chemistry*, 55(1): 9-33 (Jan. 1, 2017).

IV. Neural Interface Device Components Corresponding to the Neural Interface Device Attachable to a Target Tissue Using a Suture-Like Anchor Device FIGS. 13A-13B provide an overview of the probe geometry and cross-sections through a cable connector region 1310 (A-A'), a cable region 1320 (B-B') and an electrode region 1330 of the neural interface device 1300. As shown in FIG. 13B, the cable connector region includes a first layer of polyimide, a second layer of SU-8 epoxy, and a third layer stack of polymer that includes a layer of an electrically conducting layer. In certain embodiments, the electrically conducting layer Is Pt and the third layer stack of polymer is parylene-C.

In some embodiments, the polyimide layer has a thickness of about 150 μm. In some embodiments, the one or more polyimide layers can have a thickness of, for example, about 1 μm, about 10 μm, about 25 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, about 220 μm, about 250 μm, about 275 μm, about 300 μm, about 325 μm, about 350 μm, about 400 μm, about 500 μm, or about 800 μm. In some implementations, silicone-based layers can be cast onto both sides of the cable connector region to provide further stiffening of the cabling for robust handling in surgery.

The cable region is similar to the cable connector region except that it does not include a polyimide layer. Furthermore, the SU-8 epoxy layer is patterned. The thickness of the electrically conducting layer is about 0.125 μm or about 125 nm. In some embodiments, the one or more electrically conducting layers can have a thickness of, for example, about 1 nm, about 10 nm, about 25 nm, about 50 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, about 200 nm, about 220 nm, about 250 nm, about 275 nm, about 300 nm, about 325 nm, about 350 nm, about 400 nm, about 500 nm, about 600 nm, about 700 nm, about 800 nm, or about 900 nm. The dimensions of each of the PDMS layers can be, for example, about 1 mm in thickness and about 6 mm in width. In other embodiments, the PDMS layers can be, for example, about 0.1 to about 5 mm in thickness and about 1 mm to about 15 mm in width. Other thicknesses and widths are possible.

The electrode region 1330 of the neural interface device is similar to the cable region except that it does not include the silicone-based layer. The electrode region includes a spine and a tab region. The total thickness of the stack of polymer layers, along with the electrically conducting layer 1408 sandwiched in between can be, for example, about 9 μm. Furthermore, the SU-8 epoxy layer is patterned. In some embodiments, the polymer layer can have a thickness of, for example, about 400 nm, about 500 nm, about 600 nm, about 700 nm, about 800 nm, about 900 nm, about 1 μm, about 5 μm, about 10 μm, about 25 μm, about 50 μm, about 60 μm, about 70 μm, about 80 μm, about 90 μm, or about 100 μm.

The nerve electrode region of the probe, as shown in cross-section in FIG. 13B, has a spine, a tab (or tabs), and one or more electrodes. The spine is stiff relative to the tab by the presence of the patterned SU-8 epoxy layer 1410. In certain embodiments, the thickness of the SU-8 layer is about 25 μm. The spine is to be aligned axially with the nerve. The tab is made of the flexible polymer layers (parylene-C) and an electrically conducting layer (e.g., Pt), and with a patterned volume gradient of the SU-8 layer that starts on the spine with around 100% volume of SU-8 (i.e., no slots or pores in the SU-8 pattern) and ends with 0% volume of SU-8 (i.e., no SU-8) on the tab. The tab is designed to be compliant so it can easily wrap around a nerve. The electrode(s) on the tab are flush with the surface of the tab so that when the tab is wrapped around the nerve, the electrode(s) contact the nerve with no gap.

FIG. 13A illustrates a full probe design with a flexible cable 1320 that electrically and mechanically connects the nerve electrode region 1330 to the cable connector region 1310. Cross-section [A-A'] in FIG. 13B is of the cable connector region. The connector region is stiffened with the addition of the polyimide stiffening layer, also known as a "coverlay", in order to function as a robust connector that can fit into a cable receptacle without breaking. The cable connector region may have a plurality of contact pads. The contact pads electrically connect through the patterned electrically conducting layer in the cable to the electrode(s) located in the nerve electrode region. Cross-section [B-B'] in FIG. 13B is of the cable region. The cable region does not include the polyimide coverlay and is more flexible than the cable connector region. It is generally thicker and wider than the nerve electrode region in order to be robust with handling during surgery, yet remains flexible to enable minimally invasive layup within the body. Cross-section [C-C'] in FIG. 13B is of the nerve electrode region. This part of the probe has one or more highly flexible polymer tabs that wrap around the nerve and form intimate connection of the electrode(s) with the nerve. The nerve electrode region is anchored to the nerve using a suture-like anchor device comprising a gel polymer network that is configured to be able to wrap around the nerve. FIG. 20, explained later in more detail, illustrates the assembly of the nerve electrode region with the suture-like anchor device for attachment onto a nerve.

V. Methods of Manufacturing the Neural Interface Device Attachable to a Target Tissue Using a Suture-Like Anchor Device FIGS. 14A-14H show example processing steps for fabricating example neural interface devices in accordance with one or more example embodiments. In particular, FIGS. 14A-14H show example processing steps for fabricating the electrode region (C-C') of the neural interface device shown in FIG. 13A.

Referring to FIG. 16, an example method 1600 for manufacturing a bioelectronic neural interface device is provided. More specific details of particular implementations of method 1600 are provided below in the context of the discussion of FIGS. 14A-14H and 15A-15D, below. In particular, FIG. 16 is an illustrative flowchart for an example neural interface device manufacturing process in accordance with at least some embodiments of the present disclosure. The flowchart 1600 details the following steps: (1) deposit sacrificial material onto substrate (1602); (2) deposit and pattern first polymer layer (1604); (3) Deposit and pattern electrically conducting layer (1606); (4) deposit second polymer layer (1608) and pattern stack of first and second polymer layers; (5) deposit and pattern epoxy-based layer onto second polymer layer (1610); (6) attach a coverlay layer to contact pad region (1612); (7) deposit a first polydimethylsiloxane layer (1614); (8) separate the device from the substrate (1616); and (9) deposit a second polydimethylsiloxane layer on the other side of device (1618).

Method 1600 focuses on the layers and materials that may be added in the example manufacturing process. Once each material/layer is deposited or otherwise applied, the material/layer may be "patterned" to yield desired structural characteristics. Patterning may be accomplished in various ways deemed suitable to achieve a desired product in an effective manner. Examples of patterning steps are also discussed below in the context of FIGS. 14A-14H and 15A-15D.

At process step 1602, a sacrificial material is deposited onto a substrate. The sacrificial material may be deposited as part of a layer that includes at least a portion or region that is temporary or is otherwise subsequently changed, structurally or compositionally, in the manufacturing process. A substrate may be a solid (often planar) substance, such as a semiconductor or an insulator like glass, which serves as a foundation onto which another substance may be applied. Example substrates include but are not limited to thin slices or wafers of material such as silicon, silicon dioxide, glass, quartz, aluminum oxide, sapphire, germanium, gallium arsenide (GaAs), an alloy of silicon and germanium, indium phosphide (InP), etc. In some embodiments, the substrate can be a silicon handle wafer. In certain implementations, the sacrificial layer 1404 is spin cast onto the handle wafer 1402.

The sacrificial material layer 1404 can have a thickness of, for example, about 200, about 225, about 250, about 275, about 300, about 325, about 350, about 375, about 400, about 425 nm, about 450, about 475, about 500, about 525, about 550, about 575, about 600, about 625, about 650, about 675, about 700, about 725, about 750, about 775, about 800 nm, about 850 nm, about 900 nm, about 950 nm, about 1 μm, about 2 μm, about 3 μm, about 4 μm or about 5 μm. In an exemplary embodiment, the sacrificial material layer can has a thickness of about 700 nm.

The sacrificial material 1404, in various embodiments, has a manipulatable, modifiable, transformational, or otherwise "tunable" characteristic or property, such as a tunable solubility in aqueous media. For example, the sacrificial material may have a first solubility in a first state and a second solubility in a second state. In certain implementations, the sacrificial material may be relatively insoluble when first deposited, under a first set of conditions (e.g., in a certain pH, temperature, etc.), and/or when in contact with certain materials, and may be relatively soluble after a certain time, under a second set of conditions, and/or when in contact with certain other materials. In some embodiments, the sacrificial material may not be soluble in typical organic solvents such as acetone, isopropyl alcohol, ethanol and hexane since these solvents can be used in the device fabrication. In some embodiments, the sacrificial material can be polyacrylic acid (PAA), although other sacrificial materials are described herein.

In certain embodiments, the sacrificial layer 1404 can be crosslinked with CaCl$_2$ solution so that the sacrificial layer 1404 does not dissolve in water. Other materials or compounds similar to CaCl$_2$ may be used instead of CaCl$_2$.

Figures 14A, 14B, 14C, 14D, 14E, 14F, 14G, 14H:
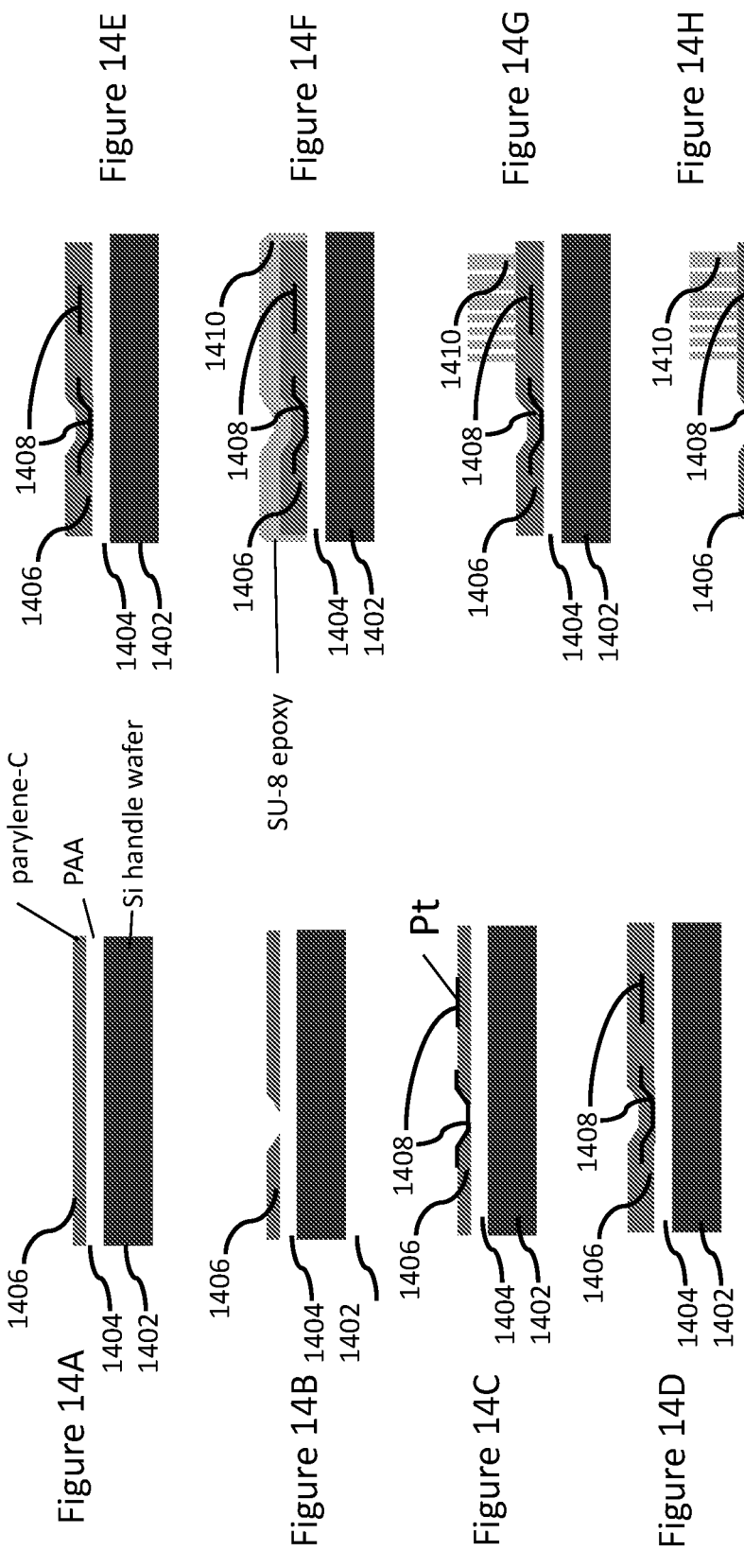
FIGS. 14A-14H show example processing steps for fabricating example neural interface devices in accordance with one or more example embodiments. In particular, FIGS.

At process step 1604, a first polymer layer 1406 may be deposited as shown in FIG. 14A and patterned onto the sacrificial material 1404 as shown in FIG. 14B. The polymer layer may serve, in various embodiments, as a moisture barrier and/or as a dielectric barrier. In certain implementations, the first polymer layer may be, partially or entirely, a poly(p-xylylene) polymer such as a parylene. In some implementations, the polymer may be parylene-C. Other useful polymers are described herein.

In some embodiments, the first polymer layer 1406 can be vapor deposited onto the sacrificial layer. In some embodiments, the thickness of the first polymer layer is about 4.5 μm. In some embodiments, the thickness of the first polymer layer is about 1 μm, about 2 μm, about 3 μm, about 4 μm, about 5 μm, about 6 μm, about 7 μm, about 8 μm, about 9 μm, about 10 μm, about 15 μm, about 20 μm, or about 25 μm.

The first polymer layer 1406 can be patterned to tapered sidewalls by 'blurring' the edges during exposure, which is done by flipping the transparency mask. The first polymer layer can then be plasma etched to form vias in the first polymer layer.

At process step 1606, an electrically conducting layer 1406 may be deposited and patterned as shown in FIG. 14C. The electrically conducting layer may include any combination of metals or other materials that allow the flow of electrical current deemed suitable. An example of electrically-conducting metal comprises a metal selected from the group including platinum, gold, platinum/iridium, and titanium. In certain embodiments, the electrically conducting layer is about 125 nm thick. In certain embodiments, the electrically conducting layer is about 25, about 50, about 75, about 80, about 90, about 100, about 110, about 120, about 130, about 140, about 150, about 175, about 200, about 225, about 250, about 275, about 300, about 325, about 350, about 375, about 400, about 425 nm, about 450, about 475, about 500, about 525, about 550, about 575, about 600, about 625, about 650, about 675, about 700, about 725, about 750, about 775, about 800 nm, about 850 nm, about 900 nm, about 950 nm, or about 1 μm thick. The electrically conducting layer 1406 is then masked and etched to form wiring, electrodes, and pads. This process forms electrodes at the beginning of the process to enable the electrodes to be along the same surface as the first polymer layer, rather than recessed from the first polymer layer. The electrodes can be formed to be flush with the first polymer layer surface to enable better adjacency to the nerve and in principle better electrical connectivity.

At process step 1608, a second polymer layer may be deposited and patterned onto the electrically conducting layer as shown in FIG. 14E. Like the first polymer layer, the second polymer layer may also be, partially or entirely, a poly(p-xylylene) polymer such as a parylene, including for example parylene-C. Other useful polymers are described herein. In some embodiments, the second polymer layer 1406 can be vapor deposited onto the sacrificial layer. In some embodiments, the thickness of the first polymer layer is about 4.5 μm. In some embodiments, the thickness of the first polymer layer is about 1 μm, about 2 μm, about 3 μm, about 4 μm, about 5 μm, about 6 μm, about 7 μm, about 8 μm, about 9 μm, about 10 μm, about 15 μm, about 20 μm, or about 25 μm. In certain embodiments, the second polymer layer can be patterned by plasma etching via into the second polymer layer.

At process step 1610, an epoxy-based layer 1410 may be deposited and patterned onto the second polymer layer. In certain embodiments, the epoxy-based layer may include an epoxy-based photo-patternable material, such as an epoxy-based photoresist. In certain implementations, the epoxy-based layer may include an epoxy-based negative photoresist such as SU-8. In some implementations, portions of the epoxy-based layer, when exposed to ultraviolet or other light, become cross-linked, while unexposed portions remain soluble and may be washed away in a subsequent step. Any pharmaceutically acceptable epoxy can be utilized in this aspect of the invention. In certain embodiments, the epoxy-based layer 1410 can be spin cast onto the second polymer layer 1408. In some embodiments, the epoxy-based layer can be about 25 μm thick. In some embodiments, the epoxy-based layer 1410 can be about 1 μm, about 5 μm, about 10 μm, about 15 μm, about 20 μm, about 21 μm, about 22 μm, about 23 μm, about 24 μm, about 25 μm, about 26 μm, about 27 μm, about 28 μm, about 29 μm, about 30 μm, about 35 μm, about 40 μm, about 45 μm, about 50 μm, about 65 μm, about 100 μm, or about 200 μm thick.

In certain embodiments, the process includes photolithographically defining the epoxy-based layer 1410 to form patterns that provide gradual stiffening along the cable indicated by the varying thickness of the patterns shown in FIG. 14G.

Although the description of FIG. 16 is described with respect to the process flow of FIG. 14, it should be appreciated that the steps 1602-1610 are performed to form the cable connector region, the cable region and the nerve electrode region shown in FIG. 13B and the process of FIG. 16 can be applied to the process flow of FIG. 15, which corresponds to the cable region of FIG. 13B.

Once the epoxy-based layer 1410 may be deposited and patterned onto the second polymer layer, at process step 1612, a coverlay layer is attached to contact pad region (1612). In certain embodiments, a coverlay material can be cut and adhered to the backside of the contact pad region shown in FIG. 14G-14H. The coverlay provides appropriate stiffness and thickness at the contact region for insertion into an electrical receptacle for interconnection to the electrical systems for stimulation or recording. In an exemplary embodiment the coverlay material is Dupont Pyralux LF Coverlay and is around 150 m in thickness. In some embodiments, the coverlay material can have a thickness of, for example, about 10, about 25, about 50, about 100, about 110, about 120, about 130, about 140, about 150, about 160, about 170, about 180, about 190, about 200, about 225, about 250, about 275, about 300, about 325, about 350, about 375, about 400, or about 425 μm.

Figures 15A, 15B, 15C, 15D:
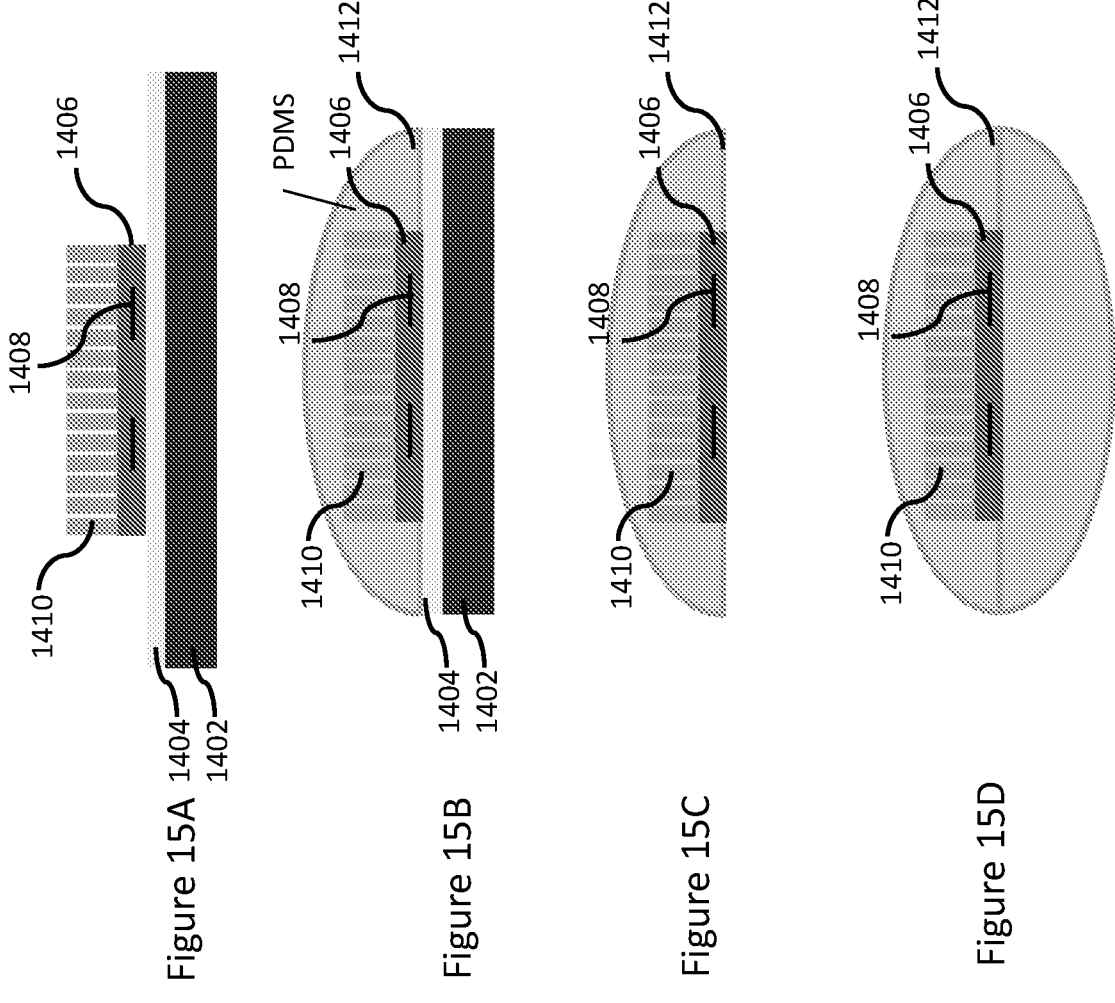

At step 1614, a first silicone-based layer 1412 is deposited as shown in FIG. 15B. In certain embodiments, the first silicone-based layer 1412 can be deposited to stiffen the cable region of the neural interface device for robustness. In certain embodiments, the cable can be probed on the substrate 1402. The substrate 1402 can be diced to form a specific width. The first silicone-based layer can then be drop cast at an angle to form a meniscus over the probe extending to the edges of the diced substrate 1402. In certain embodiments, certain silicone-based layers may replace the silicone-based layer 1412.

In certain embodiments, the silicone-based layer may be deposited onto the epoxy-based layer on one side of the device and onto the polymer layer (such as parylene-C layer)

on the other side of the device. Any pharmaceutically acceptable silicone encapsulant can be utilized in this aspect of the invention. In an exemplary embodiment, the silicone is polydimethylsiloxane (PDMS) and specifically Sylgard 184 (Dow Corning) silicone elastomer encapsulant.

At step 1616, the device is separated from the substrate (1616). In certain embodiments, the structure is immersed in water to dissolve the PAA sacrificial layer 1404 and to release the neural interface device that includes the probe. In certain embodiments, the structure is immersed in sodium chloride solution to dissolve the PAA sacrificial layer 1404 and to release the neural interface device that includes the probe.

At step 1618, a second silicone-based layer is deposited on the other side of the neural interface device that was released or separated from the substrate. In certain embodiments, the second silicone-based layer is drop cast at an angle on the other side of the neural interface device. In certain embodiments, the second silicone-based layer is drop cast at an angle on the other side of the neural interface device such that the second silicone-based layer is formed on the other side of the cable region shown in FIG. 15D but not around the contact pad region shown in FIG. 14H.

The silicone-based layers can have a gradient in thickness that ranges from zero thickness near the electrode region of the device to a maximum thickness at the contact pad region of the device. The silicone-based layer on each side can have a maximum thickness of, for example, about 0.5, about 1, about 1.5, about 2, about 2.5, or about 3 mm. In an exemplary embodiment, the silicone-based layer on each side has a maximum thickness of about 1.5 mm.

As described in the process of FIG. 16, the electrode contacts can be formed to be substantially flush with the surface of the probe of the neural interface device. By fabricating electrode contacts that are substantially flush with the surface of the probe (i.e., not significantly recessed), enhanced electrical contact with the nerve can be achieved. In various embodiments, a substantially flush electrode contact has no measurable distance from the surface of the probe and the surface of the electrode contact (i.e., zero recess).

In certain implementations, a substantially flush electrode contact has a separation of no more than about 5 nanometers (nm) from the surface of the probe and the surface of the electrode contact (i.e., a recess of about 5, about 4, about 3, about 2, or about 1 nm or less). In some implementations, a substantially flush electrode contact has a separation of no more than about 25 nm from the surface of the probe and the surface of the electrode contact (i.e., a recess of about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, about 2, or about 1 nm or less). In other embodiments of the invention, a substantially flush electrode contact has a separation of no more than about 10, about 15, or about 20 nm from the surface of the probe and the surface of the electrode contact (i.e., a recess of about 10, about 15, or about 20 nm or less). In alternative embodiments, the electrode contacts may be configured to protrude or extend out (e.g., about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24 or about 25 nm) from the surface of the probe).

In various embodiments, the device is immersed in water to dissolve the sacrificial material (e.g., PAA), releasing the device after a certain time (e.g., about 2 hours or less). In other embodiments of the invention, the device is released after about 15 mins, about 30 mins, about 45 mins, about 1 hr, about 1.5 hrs, about 2 hrs, about 2.5 hrs, about 3 hrs, about 3.5 hrs, or about 4 hrs. The optional presence of silicone-based layers may result in wider cabling as part of the device and thus require a longer time to release the device from its substrate (e.g., about 20 hrs or less than about 24 hrs). The attached device may then be removed from the glass or silicon substrate 302.

In various embodiments, PAA may be selected as the sacrificial layer material because it has tunable solubility in water and thus may help ensure that the hydrogel does not need to contact the sort of relatively harsher chemicals used in existing fabrication steps. Other examples of sacrificial materials with tunable solubility include block-copolymers of PAA with a non-acrylic acid monomer, e.g., poly(styrene)-block-poly(acrylic acid); polyacrylamide polymers, e.g., poly(acrylamide-co-acrylic acid), poly(N-alkylacrylamide-co-acrylic acid) polymers; a poly(alkylene-co-acrylic acid) polymer; and generally a polymer with a side group(s) containing any ionizable moiety. Non-limiting examples of such ionizable moieties include carboxylic acid, hydroxyl, amide, sulfonamide, phosphate, sulfate, sulfonate, sulfinate, amine, thiol, imide, oxime, peroxide, carbamate, guanidine, hydrazine, hydrazide, hydrazine, hydroxamic acid, and hydroxamic amidine.

In various embodiments, PAA is used as a sacrificial material for its stability in typical organic solvents, such as alcohols, acetone, isopropyl alcohol, ethanol, and hexane used in the device fabrication. In an exemplary embodiment, the sacrificial material is PAA, which is insoluble in water when treated with bivalent ions such as $Ca^{2+}$. At the transfer process step, the PAA is treated first with NaCl solution to reverse its water solubility property. The $Na^+$ displaces the $Ca^{2+}$ and makes the PAA soluble in water. Immersion in water of the device on the substrate eventually dissolves the PAA sacrificial material and releases the device from the substrate.

In example embodiments, the dopamine groups in this hydrogel may have adhesive properties and may, in some implementations, be found in mussels. See e.g., Ding et al., "Mussel-inspired polydopamine (PDA) for bio-surface functionalization," *Biosurface and Biotribology*, 2(4): 121-136 (2016); and P. Forooshane and B. Lee, "Recent approaches in designing bioadhesive materials inspired by mussel adhesive protein," *Polymer Chemistry*, 55(1): 9-33 (Jan. 1, 2017).

FIG. 19 illustrates a plan view of the wafer layout used to manufacture the probes of the nerve interface devices described herein. The wafer layout shown in FIG. 19 includes 6 cervical vagus probes and 4 abdominal vagus probes (having the shorter lengths). The outer circle is 4" (10.2 cm) in diameter denoting the extent of the wafer and the inner circle is 3.8" in diameter, denoting the inner region for highest manufacturing yield.

In some embodiments, the probes can differ in size, as shown in FIG. 19. For instance, the probes can have differing cable lengths and the shape of the cable can be different. In addition, the probes can include differing numbers of wires to accommodate the number of electrodes on a given probe. In some embodiments, each probe instance on the wafer could be a different design variant of the tabs and electrodes if desired.

VI. Cervical Vagus Probes

FIGS. 17A-17C illustrate various vagus probes of differing sizes configured to accommodate nerve diameters of about 350 μm, about 450 μm, or about 500 μm. The vagus neural probes shown in FIGS. 17A-17C can be a part of corresponding neural interface devices and used to attach to the cervical vagus nerve. The probes include two tabs, and each tab includes two electrodes. The electrodes are axial in line with the nerve. Thus in this configuration, the electrodes are meant to selectively stimulate or record nerve fibers. Different length tabs and locations of electrodes were designed to accommodate different nerve radii and diameters, as indicated; these can be changed in size to position the probe on the cervical vagus nerve trunk or any of its distal branches in the thoracic or abdominal cavities. In some embodiments, each tab can include one or more electrodes. In some embodiments, each probe can include one or more tabs. The tabs can be located on either side of the spine (as shown in FIGS. 18A-C), or the tabs can be located on only one side of the spine. By including more electrodes per tab, the probe can include a larger number of electrodes. Moreover, the electrodes can be staggered in distance from the spine of the probe to locate the electrodes in different locations along the circumference of the nerve as shown in FIGS. 12A-12C. In some embodiments, the size of the electrodes can vary based on the type of nerve, tissue or ganglion to which to attach the probe.

Note that each electrode has two wires connected to it in an electrical loop. This enables the user to check the resistance of the loop with an ohmmeter prior to use to ensure the connection is sound. If the resistance is an open circuit (or significantly high such as over 100 kohm), then the electrode wiring has a break. The two wires connected to the electrode may provide redundancy such that if one wire is broken, the other wire can still be used to complete the neural connection. In some embodiments, the dimensions of the tabs, including the length of the tabs can vary. Longer tabs can be used for nerves with larger diameters while shorter tabs can be used for nerves with smaller diameters.

VII. Abdominal Vagus Probes

FIGS. 18A-C illustrate various abdominal vagus probes of differing sizes configured to accommodate nerve diameters of about 100 μm, about 200 μm, or about 300 μm, or any amounts in-between these values. The abdominal vagus neural probes shown in FIGS. 18A-18C can be a part of corresponding neural interface devices and used to attach to the abdominal vagus nerve. The probes include two tabs, and each tab includes two electrodes. The electrodes are axial in line with the nerve. Thus in this configuration, the electrodes are meant to record or stimulate the whole nerve. Different length tabs and locations of electrodes were designed to accommodate different nerve radii and diameters, as indicated. In some embodiments, each tab can include one or more electrodes. In some embodiments, each probe can include one or more tabs. By including more electrodes per tab, the probe can include a larger number of electrodes. Moreover, the electrodes can be staggered in distance from the spine of the probe to locate the electrodes in different locations along the circumference of the nerve as shown in FIGS. 12A-12C. In some embodiments, the size of the electrodes can vary based on the type of nerve to which to attach the probe.

Note that each electrode has two wires connected to it in an electrical loop. This enables the user to check the resistance of the loop with an ohmmeter prior to use to ensure the connection is sound. If the resistance is an open circuit (or significantly high such as over 100 kohm), then the electrode wiring has a break. The two wires connected to the electrode may provide redundancy such that if one wire is broken, the other wire can still be used to complete the neural connection. In some embodiments, the dimensions of the tabs, including the length of the tabs can vary. Longer tabs can be used for nerves with larger diameters while shorter tabs can be used for nerves with smaller diameters.

Suture-Like Anchoring Device

In one aspect, the present disclosure provides a suture-like anchor device comprising a gel polymer network comprising a crosslinkable polymer precursor, wherein the gel polymer network is configured to couple with any neural interface device disclosed herein. The suture-like anchor device is configured to be able to wrap around a target tissue to anchor a probe to the target tissue. In some implementations, the suture-like anchor device comprises non-toxic and physiologically acceptable materials.

In some implementations, the gel polymer network comprises a hydrogel. The hydrogel may be, or may include, polyethylene glycol (PEG). Examples of other useful hydrogels include, but are not limited to, various polymers crosslinked to form hydrogels. Examples include crosslinked polymers of poly(ethylene oxide), gelatin, albumin, poly (ethylene glycol-co-propylene glycol), poly(vinyl pyrrolidinone), poly(vinyl alcohol), polybutylene terephthalate, polysaccharides including dextran, chitosan, carboxymethyl, curdlan, and pullulan, acrylic polymers, methacrylic polymers, poly(alpha-hydroxy acids), polylactides, polyglycolides, polyacrylamides, polyamides, polyanhydrides, or any block copolymers thereof. Examples of synthetically prepared monomers that may be crosslinked to form these hydrogels include ethylenically unsaturated hydrocarbons.

Additionally or alternatively, in some implementations, the crosslinkable polymer precursor comprises a dopamine moiety. In some implementations, the hydrogel is polydopamine-polyacrylamide (PDA-PAM). Dopamine containing hydrogels may be synthesized according to Han et al., *NPG Asia Materials,* 9: 372 (2017), or Huang et al., *Adv. Funct. Mater.,* 28: 1801059 (2018). In certain implementations, the hydrogel may be synthesized separately as a telechelic Dopa-modified polyethylene glycol-based hydrogel.

Crosslinkable polymer precursors or hydrogels of the suture-like anchor device provided herein may be adhesive. Adhesive hydrogels may comprise a drug, ligand, or peptide that binds to a site expressed on a target tissue. In some implementations, adhesive hydrogels are strained and attached to the target tissue to facilitate adhesion. The level of strain may be about 500-about 1,000%, about 1,000-about 1,500% about 1,500-about 2,000%, about 2,000-about 2,500%, or about 2,500-about 3,000%. In some implementations the hydrogel is strained greater than about 3,000%.

In some implementations, the hydrogel comprises a Young's modulus (E) between about 10 kPa and about 100 kPa. In some implementations, the Young's modulus is about 10 kPa, about 15 kPa, about 20 kPa, about 25 kPa, about 30 kPa, about 35 kPa, about 40 kPa, about 45 kPa, about 50 kPa, about 55 kPa, about 60 kPa, about 65 kPa, about 70 kPa, about 75 kPa, about 80 kPa, about 85 kPa, about 90 kPa, about 95 kPa or about 100 kPa.

In some implementations, the hydrogel comprises a shear modulus (G) between about 1 kPa and about 100 kPa. In some implementations, the shear modulus is about 1 kPa, about 5 kPa, about 10 kPa, about 15 kPa, about 20 kPa, about 25 kPa, about 30 kPa, about 35 kPa, about 40 kPa, about 45 kPa, about 50 kPa, about 55 kPa, about 60 kPa, about 65 kPa, about 70 kPa, about 75 kPa, about 80 kPa, about 85 kPa, about 90 kPa, about 95 kPa, or about 100 kPa.

In some implementations, the hydrogel comprises a Poisson's ratio (v) between 0 and about 0.5. In some implementations, the Poisson's ratio (v) is about 0, about 0.1, about 0.2, about 0.3, about 0.4 or about 0.5.

In some implementations, the hydrogel comprises a yield strength between about 1 Pa and about 1000 Pa. In some implementations, the yield strength is about 1 Pa, about 5 Pa, about 10 Pa, about 15 Pa, about 20 Pa, about 25 Pa, about 30 Pa, about 35 Pa, about 40 Pa, about 45 Pa, about 50 Pa, about 55 Pa, about 60 Pa, about 65 Pa, about 70 Pa, about 75 Pa, about 80 Pa, about 85 Pa, about 90 Pa, about 95 Pa, about 100 Pa, about 150 Pa, about 200 Pa, about 250 Pa, about 300 Pa, about 350 Pa, about 400 Pa, about 450 Pa, about 500 Pa, about 550 Pa, about 600 Pa, about 650 Pa, about 700 Pa, about 750 Pa, about 800 Pa, about 850 Pa, about 900 Pa, about 950 Pa, or about 1000 Pa.

In some implementations, the hydrogel comprises an ultimate tensile strength between about 10 kPa and about 100 kPa. In some implementations, the ultimate tensile strength is about 10 kPa, about 15 kPa, about 20 kPa, about 25 kPa, about 30 kPa, about 35 kPa, about 40 kPa, about 45 kPa, about 50 kPa, about 55 kPa, about 60 kPa, about 65 kPa, about 70 kPa, about 75 kPa, about 80 kPa, about 85 kPa, about 90 kPa, about 95 kPa or about 100 kPa.

In some implementations, the hydrogel can exhibit an effective interfacial adhesion of between 0.1 and 10 $J/m^2$. In some implementations, the effective interfacial adhesion is about 0.1 $J/m^2$, about 0.2 $J/m^2$, about 0.3 $J/m^2$, about 0.4 $J/m^2$, about 0.5 $J/m^2$, about 0.6 $J/m^2$, about 0.7 $J/m^2$, about 0.8 $J/m^2$, about 0.9 $J/m^2$, about 1 $J/m^2$, about 2 $J/m^2$, about 3 $J/m^2$, about 4 $J/m^2$, about 5 $J/m^2$, about 6 $J/m^2$, about 7 $J/m^2$, about 8 $J/m^2$, about 9 $J/m^2$, or about 10 $J/m^2$.

In some implementations the hydrogel has a fracture energy between about 100-about 1,000 $J/m^2$. In some implementation, the fracture energy is about 100 $J/m^2$, about 150 $J/m^2$, about 200 $J/m^2$, about 250 $J/m^2$, about 300 $J/m^2$, about 350 $J/m^2$, about 400 $J/m^2$, about 450 $J/m^2$, about 500 $J/m^2$, about 550 $J/m^2$, about 600 $J/m^2$, about 650 $J/m^2$, about 700 $J/m^2$, about 750 $J/m^2$, about 800 $J/m^2$, about 850 $J/m^2$, about 900 $J/m^2$, about 950 $J/m^2$, or about 1000 $J/m^2$.

Properties of the hydrogel may be determined by the skilled worker by methods known in the art, including extensiometry, compression testing, bulge testing, or indentation testing as described in Ahearne et. al. *Topics in Tissue Engineering, Vol.* 4. Eds. N Ashammakhi, R Reis, & F Chiellini (2008).

Additionally or alternatively, in some implementations, the gel polymer network may comprise one or more of the following: (a) comprises polyethylene glycol; (b) comprises a crosslinked polymers selected from the group consisting of poly(ethylene oxide), poly(ethylene glycol-co-propylene glycol), poly(vinyl pyrrolidinone), poly(vinyl alcohol), acrylic polymers, and methacrylic polymers; (c) comprises a synthetically prepared monomer crosslinked to form a hydrogel, wherein the monomer is selected from the group consisting of ethylenically unsaturated hydrocarbons such as acrylic monomers and methacrylic monomers; (e) comprises a stimulus-responsive telechelic Dopa-modified polyethylene glycol; and/or (f) has a thickness selected from the group consisting of about 0.2 mm, about 0.25 mm, about 0.5 mm, about 0.75 mm, about 1 mm, about 1.25 mm, about 1.5 mm, about 1.75 mm, about 2 mm, about 2.25 mm, about 2.5 mm, about 2.75 mm, about 3 mm, about 3.25 mm, and about 3.5 mm.

Additionally or alternatively, in some implementations, the gel polymer network is formed by crossing linking a redox active metal and crosslinkable polymer precursor. The redox active metal may be, for example, $Fe^{3+}$, $Au^{3+}$, $V^{5+}$, or $Ag^+$.

In certain implementations of the suture like anchor device, $Fe^{3+}$-$[PEG\text{-}Dopa]_4$ hydrogels may be formed through $Fe^{3+}$-induced cross-linking of four-arm polyethylene glycol-dopamine precursors to produce networks. This metal ion can induce covalent coupling of the dopamines or can bridge catechols through coordination bond formation. The relative amounts of H-bonds, coordination bonds, and covalent bonds can be controlled by the $[Fe^{3+}]$: [Dopa] molar ratio from 0.5:1 to >2:1 in precursor solutions. Sustained ultrasonic energy may stabilize hydrogels through the formation of additional cross-links via free radical-mediated coupling of pendant catechols.

In certain implementations of the suture like anchor device, $Au^{3+}$-$[PEG\text{-}Dopa]_4$ hydrogels may be formed through $Au^{3+}$-induced cross-linking of four-arm polyethylene glycol-dopamine precursors to produce networks. In some implementations, $HAuCl_4$ ($Au^{3+}$) is used as a source of the redox active metal. The $Au^{3+}$ can also create a hydrogel through redox coupling of pendant catechols followed by subsequent gelation. However, unlike $Fe^{3+}$, the reduction of $Au^{3+}$ into Au(0) produces benign nanoparticles that do not bind to catechols, thus leading to the availability of more free catechols that can bind to electronics, tissue, or other substrates and an improvement in the handle-ability and adhesion to tissue of the probes disclosed herein. Further, it has been found that free $Fe^{3+/2+}$ ions in hydrogels that are formed by using $Fe^{3+}$ are more susceptible to bacterial infection. Without wishing to be bound by theory, it is believed that the increased susceptibility to bacterial infection may be due to the possible uptake of iron by bacteria, which is an important component in bacterial metabolism. Accordingly, the use of $Au^{3+}$-$[PEG\text{-}Dopa]_4$ hydrogels as a suture-like anchoring device is significantly less susceptible to infection compared to $Fe^{3+}$ containing hydrogel counterparts.

Additionally or alternatively, in some implementations, the suture like anchor device may further comprise a detachable surgical support substrate, wherein the gel polymer network is deposited on the detachable surgical support substrate. In some implementations, the detachable surgical support substrate is parafilm, polytetrafluoroethylene, nylon, or any other type of inert polymer film.

Additionally or alternatively, in some implementations, the Young's modulus of the suture-like anchor device is about 10 kPa to about 100 kPa. In some implementations, the Young's modulus of the suture-like anchor device is about 10 kPa, about 15 kPa, about 20 kPa, about 25 kPa, about 30 kPa, about 35 kPa, about 40 kPa, about 45 kPa, about 50 kPa, about 55 kPa, about 60 kPa, about 65 kPa, about 70 kPa, about 75 kPa, about 80 kPa, about 85 kPa, about 90 kPa, about 95 kPa or about 100 kPa.

Additionally or alternatively, in some implementations, the shear modulus (G) of the suture-like anchor device is about 1 kPa to about 100 kPa. In some implementations, the shear modulus of the suture-like anchor device is about 1 kPa, about 5 kPa, about 10 kPa, about 15 kPa, about 20 kPa, about 25 kPa, about 30 kPa, about 35 kPa, about 40 kPa, about 45 kPa, about 50 kPa, about 55 kPa, about 60 kPa, about 65 kPa, about 70 kPa, about 75 kPa, about 80 kPa, about 85 kPa, about 90 kPa, about 95 kPa, or about 100 kPa.

Additionally or alternatively, in some implementations, the yield strength of the suture-like anchor device is about 1 Pa to about 1000 Pa. In some implementations, the yield strength of the suture-like anchor device is about 1 Pa, about 5 Pa, about 10 Pa, about 15 Pa, about 20 Pa, about 25 Pa, about 30 Pa, about 35 Pa, about 40 Pa, about 45 Pa, about 50 Pa, about 55 Pa, about 60 Pa, about 65 Pa, about 70 Pa, about 75 Pa, about 80 Pa, about 85 Pa, about 90 Pa, about 95 Pa, about 100 Pa, about 150 Pa, about 200 Pa, about 250 Pa, about 300 Pa, about 350 Pa, about 400 Pa, about 450 Pa, about 500 Pa, about 550 Pa, about 600 Pa, about 650 Pa, about 700 Pa, about 750 Pa, about 800 Pa, about 850 Pa, about 900 Pa, about 950 Pa, or about 1000 Pa.

Additionally or alternatively, in some implementations, the suture-like anchor device comprises a Poisson's ratio (v) of about 0 to about 0.5. In some implementations, the Poisson's ratio (v) of the suture-like anchor device is about 0, about 0.1, about 0.2, about 0.3, about 0.4 or about 0.5.

Additionally or alternatively, in some implementations, the ultimate tensile strength of the suture-like anchor device is about 10 kPa to about 100 kPa. In some implementations, the ultimate tensile strength of the suture-like anchor device is about 10 kPa, about 15 kPa, about 20 kPa, about 25 kPa, about 30 kPa, about 35 kPa, about 40 kPa, about 45 kPa, about 50 kPa, about 55 kPa, about 60 kPa, about 65 kPa, about 70 kPa, about 75 kPa, about 80 kPa, about 85 kPa, about 90 kPa, about 95 kPa or about 100 kPa.

Additionally or alternatively, in some implementations, the effective interfacial adhesion of the suture-like anchor device is about 0.1 to about 10 J/m$^2$. In some implementations, the effective interfacial adhesion is about 0.1 J/m$^2$, about 0.2 J/m$^2$, about 0.3 J/m$^2$, about 0.4 J/m$^2$, about 0.5 J/m$^2$, about 0.6 J/m$^2$, about 0.7 J/m$^2$, about 0.8 J/m$^2$, about 0.9 J/m$^2$, about 1 J/m$^2$, about 2 J/m$^2$, about 3 J/m$^2$, about 4 J/m$^2$, about 5 J/m$^2$, about 6 J/m$^2$, about 7 J/m$^2$, about 8 J/m$^2$, about 9 J/m$^2$, or about 10 J/m$^2$.

Additionally or alternatively, in some implementations, the suture-like anchor device has a fracture energy between about 100-about 1,000 J/m$^2$. In some implementation, the fracture energy of the suture-like anchor device is about 100 J/m$^2$, about 150 J/m$^2$, about 200 J/m$^2$, about 250 J/m$^2$, about 300 J/m$^2$, about 350 J/m$^2$, about 400 J/m$^2$, about 450 J/m$^2$, about 500 J/m$^2$, about 550 J/m$^2$, about 600 J/m$^2$, about 650 J/m$^2$, about 700 J/m$^2$, about 750 J/m$^2$, about 800 J/m$^2$, about 850 J/m$^2$, about 900 J/m$^2$, about 950 J/m$^2$, or about 1000 J/m$^2$.

The suture-like anchor device of the present disclosure is useful for anchoring a probe disclosed herein to various tissue structures upon implantation. For example, decoupling an electrode from the suture-like anchor device allows for the integration of flexible electrodes with extremely fine structures such as ultrafine nerve fibers in the distal peripheral nervous system, which are typically difficult to adhere to/maintain constant electrical contact with.

VIII. Methods of Surgically Implanting the Neural Interface Device Using a Suture-Like Anchoring Device Referring now to FIGS. 20A-20E and FIG. 21, the present disclosure provides a method for surgically implanting a probe onto a target tissue in a subject comprising (a) placing a first surface of the probe 2010 onto an adhesive hydrogel layer 2012, wherein the adhesive hydrogel layer 2012 comprises a first portion and a second portion; (b) placing a second surface of the probe 2010 onto a surface of the target tissue 2002, wherein the second surface of the probe 2010 is opposite to the first surface of the probe 2010; and (c) wrapping the adhesive hydrogel layer 2012 around the target tissue 2002 such that the first portion of the adhesive hydrogel layer 2012 contacts the second portion of the adhesive hydrogel layer 2012. In some implementations, the probe 2010 is placed between the first portion 2016a and the second portion 2016b of the adhesive hydrogel layer 2012. Additionally or alternatively, in some implementations, the length of the probe 2010 is less than the circumference of the target tissue 2002. Additionally or alternatively, in some implementations, the length of the adhesive hydrogel layer 2012 is greater than the circumference of the target tissue 2002. The second surface of the probe 2010 may be placed onto a dorsal, ventral, lateral, anterior or posterior surface of the target tissue. In some implementations, the subject is a mammal, such as a human.

Additionally or alternatively, in some implementations, the adhesive hydrogel layer 2012 is deposited onto a detachable surgical support substrate 2014. In some implementations, the method further comprises removing the detachable surgical support substrate. Examples of detachable surgical support substrate include parafilm, polytetrafluoroethylene, nylon, or any other type of inert polymer film.

Figures 20A, 20B, 20C, 20D, 20E:
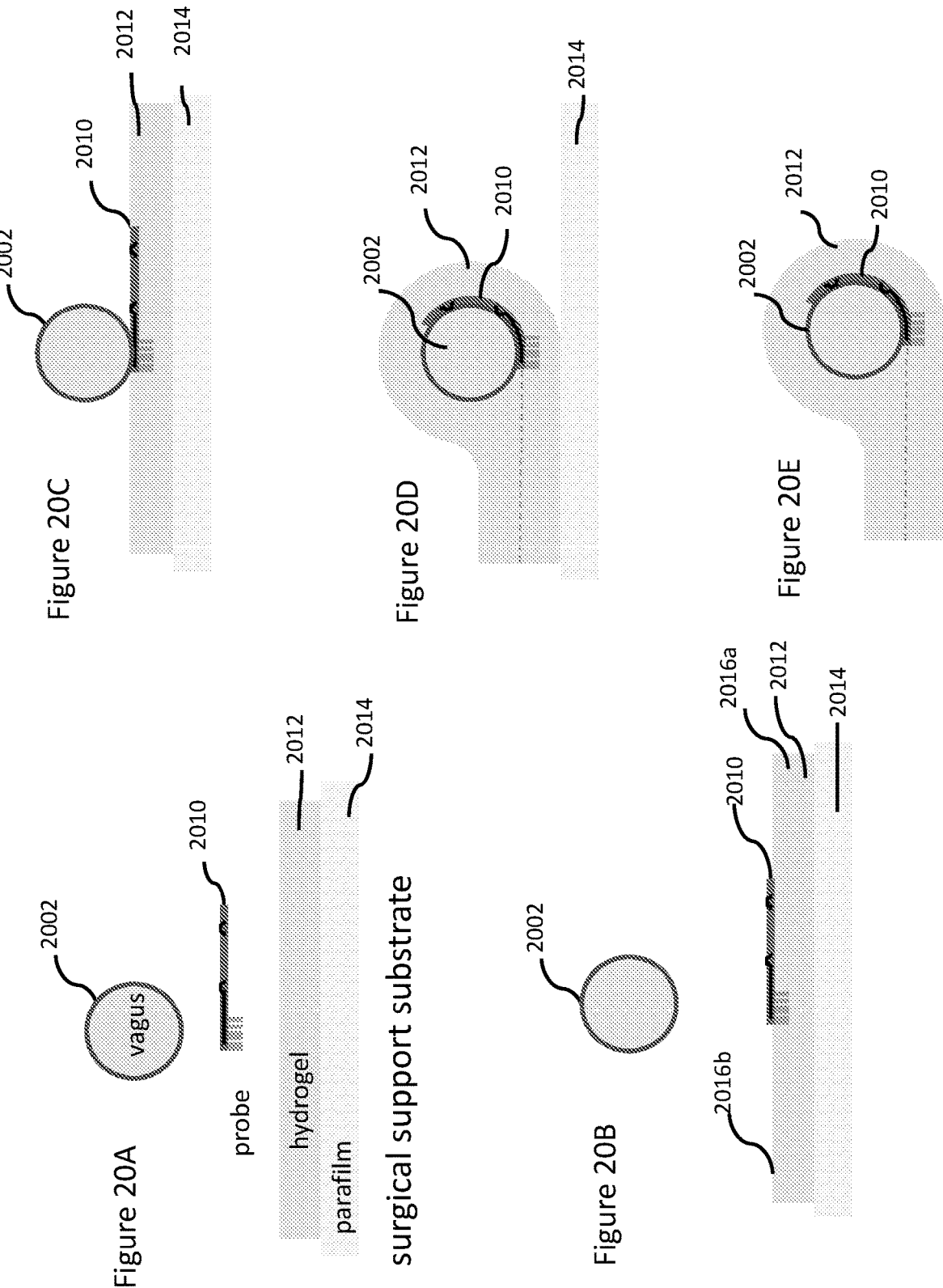

FIGS. 20A-20E illustrates a ventral view of the sequence of events during a surgical procedure to attach the neural interface device to a nerve. As shown in FIG. 20A, a hydrogel 2012 supported by a detachable surgical support substrate 2014 and a neural interface device, such as a probe 2010 is placed under a nerve 2002. As shown in FIG. 20B, the probe 2010 is placed onto the hydrogel 2012. As shown in FIG. 20C, the nerve 2002 is positioned on top of the probe 2010. As shown in FIG. 20D, the hydrogel 2012 is then pulled or wrapped around the nerve 2002 and opposing halves of the hydrogel 2012 are stuck together. Although not shown in the FIGS. 21A-21D, the electrodes on a second tab of the probe 2010 are similarly brought into contact with the nerve 2002 further along the length of the nerve, thereby completing the circumferential electrode arrangement.

FIG. 21 is an illustrative flowchart 2100 for an example method of securing the electrode pads and hydrogel to a nerve, tissue, or ganglion in accordance with at least some embodiments of the present disclosure. The flowchart depicts the following steps: (1) access a peripheral nerve or ganglia via a surgical procedure (2102); (2) identify a nerve location at which to secure a neural interface device (2104); (3) place the neural interface device on to the hydrogel layer (2106); (4) align the assembly of the neural interface device and hydrogel to the nerve (2108); (5) secure the neural interface device to the nerve by folding the hydrogel layer around the nerve location (2110); (6) remove the substrate holding the hydrogel (2112); and (7) close the surgical site (2114).

Figures 22A, 22B, 22C, 22D:
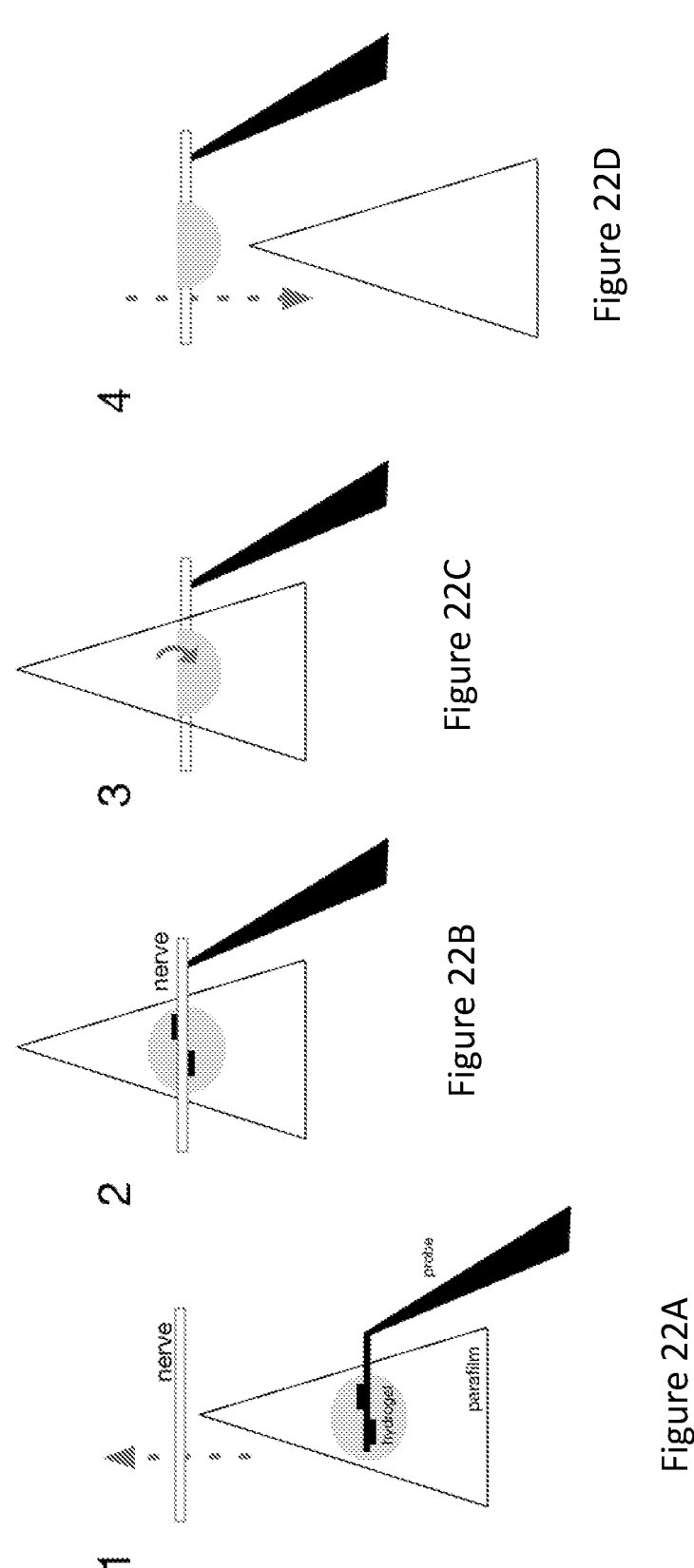

FIGS. 22A-22D illustrate a method of wrapping the vagus nerve with the conformable neural interface system. FIG. 22A shows the neural interface system including the suture-like anchor device and the neural interface device, such as the probe, placed under the vagus nerve. FIG. 22B shows the nerve positioned against the probe. FIG. 22C shows that the suture-like anchor device, optionally a hydrogel is pulled around the nerve. FIG. 22D shows the removal of the detachable surgical support substrate holding the suture-like anchor device.

IX. Methods of Use

The bioelectronic neural interface devices of the present invention can be used in a wide variety of indications. For example, in one aspect, the bioelectronic neural interface device of the present disclosure may be used to stimulate or modulate (e.g., activate or inhibit) one or more neurons, ganglia, or tissue for the treatment of a particular disease or medical condition.

The modulation of nerve tissues such as autonomic nerve tissue including central and peripheral, sympathetic and parasympathetic, and enteric may be used to achieve a desired physiological result or treatment of various medical conditions. In some embodiments, the method of treatment involves electrical activation of one or more nerves. Unilateral activation or bilateral activation may be utilized.

Electrical nerve modulation (nerve activation, stimulation, and/or inhibition) is accomplished by applying an energy signal (pulse) at a certain frequency to the neurons of a nerve (nerve stimulation). The energy pulse causes depolarization of neurons within the nerve above the activation threshold resulting in an action potential. The energy applied is a function of the current (or voltage) amplitude and pulse width or duration. Biphasic pulses help inhibit buildup of charge and are often used. Activation or inhibition can be a function of the frequency of the energy signal, with low frequencies on the order of about 1 to about 50 Hz resulting in activation of a nerve for some embodiments and high frequencies greater than about 100 Hz resulting in inhibition of a nerve for some embodiments. Inhibition can also be accomplished by continuous energy delivery resulting in sustained depolarization. Different neuronal types may respond to different energy signal frequencies and energies with activation or inhibition.

Various stimulation patterns, ranging from continuous to intermittent, may be utilized for various embodiments. With intermittent stimulation of nerves, an energy signal is delivered to a nerve or nerve tissue for a period of time at a certain frequency during the signal on-time. The signal on-time is followed by a period of time with no energy delivery, referred to as signal-off time. The ratio of the signal on-time to the sum of the signal on-time plus the signal off time is referred to as the duty cycle and it can in some embodiments range from about 1% to about 100%. Alternatively, nerve stimulation may be conducted at nearly a continuous, or 100%, duty cycle.

To help determine the strength and/or duration of electrical stimulation required to produce the desired effect, in some embodiments, a patient's response to and/or need for treatment is monitored. For example, muscle activity (e.g., limb EMG), electrical activity of a nerve (e.g., ENG), and/or electrical activity of the brain (e.g., EEG) may be detected. Other measures of the state of the patient may additionally or alternatively be detected. For instance, medication, cells and in particular immune cells, neurotransmitter, hormone, interleukin, cytokine, lymphokine, chemokine, growth factor, and/or enzyme levels or their changes, and/or levels or changes in other substance(s) borne in the blood cerebrospinal fluid (CSF), bronchoalveolar lavage fluid (BALF) and/or breath may be detected, using conventional detection methods known in the art.

In addition to the duty cycle and signal parameters (frequency, on-time, current pulse amplitude and pulse width) are treatment parameters. Therapy may be delivered at different intervals during the day or week, or continuously. Continuous treatment may prevent the progression of a disease or condition during the off therapy time. Intermittent treatment may prevent the development of tolerance to the therapy. A desirable intermittent therapy embodiment may be, for example, about 18 hours on and about 6 hours off, about 12 hours on and about 12 hours off, about 3 days on and about 1 day off, about 3 weeks on and about one week off or some other combination of daily or weekly cycling.

Alternatively, treatment may be delivered at a higher interval rate, say, about every three hours, for shorter durations, such as about 2 minutes to about 30 minutes. The treatment duration and frequency may be tailored to achieve a desired result. Treatment duration for some embodiments may last for as little as a few minutes to as long as several hours.

Additionally or alternatively, in some implementations, the method further comprises detecting or monitoring bioelectrical signals generated by the target tissue. Additionally or alternatively, in some implementations, the method further comprises detecting or monitoring the levels of one or more hormones, neurotransmitters, immune cells, interleukins, cytokines, lymphokines, chemokines, growth factors, and enzymes in a subject.

Additionally or alternatively, in some implementations, the target tissue comprises a nerve, a ganglion, muscle tissue, cardiac tissue, gastrointestinal tissue, liver tissue, pancreatic tissue, spleen tissue, and the like. The nerve may be a peripheral nerve, a cranial nerve, a spinal nerve, a sympathetic nerve, a parasympathetic nerve, a sensory nerve, a motor nerve, or a mixed nerve. Examples of cranial nerves include olfactory nerves (and tracts), optic nerves, oculomotor nerve, trochlear nerve, trigeminal nerve, abducent nerve, facial nerve, vestibulocochlear nerve, glossopharyngeal nerve, vagus nerve, accessory nerve, and hypoglossal nerve. Examples of spinal nerves include posterior divisions, anterior divisions, thoracic nerves, lumbosacral plexus, sacral nerves and coccygeal nerves. Examples of sympathetic nerves include the cephalic portion, the cervical portion, the thoracic portion, the abdominal portion, the pelvic portion, or the great plexuses of the sympathetic system.

Examples of nerves include but are not limited to abdominal aortic plexus, abducens nerve, accessory nerve, accessory obturator nerve, alderman's nerve, anococcygeal nerve, ansa cervicalis, anterior interosseous nerve, anterior superior alveolar nerve, Auerbach's plexus, auriculotemporal nerve, axillary nerve, brachial plexus, buccal branch of the facial nerve, buccal nerve, cardiac plexus, cavernous nerves, cavernous plexus, cervical branch of the facial nerve, cervical plexus, chorda tympani, coccygeal nerve, cochlear nerve, common fibular nerve, common palmar digital nerves of median nerve, deep branch of the radial nerve, deep fibular nerve, deep petrosal nerve, deep temporal nerves, digastric branch of facial nerve, dorsal branch of ulnar nerve, dorsal nerve of clitoris, dorsal nerve of the penis, dorsal scapular nerve, esophageal plexus, ethmoidal nerves, external laryngeal nerve, external nasal nerve, facial nerve, femoral nerve, frontal nerve, gastric plexuses, genital branch of genitofemoral nerve, genitofemoral nerve, glossopharyngeal nerve, greater auricular nerve, greater occipital nerve, greater petrosal nerve, hepatic plexus, hypoglossal nerve, iliohypogastric nerve, ilioinguinal nerve, inferior alveolar nerve, inferior anal nerves, inferior cardiac nerve, inferior gluteal nerve, inferior hypogastric plexus, inferior mesenteric plexus, inferior palpebral nerve, infraorbital nerve, infraorbital plexus, infratrochlear nerve, intercostal nerve, intercostobrachial nerve, intermediate cutaneous nerve, internal carotid plexus, internal laryngeal nerve, interneuron, lacrimal nerve, lateral cord, lateral cutaneous nerve of forearm, lateral cutaneous nerve of thigh, lateral pectoral nerve, lateral plantar nerve, lateral pterygoid nerve, lesser occipital nerve, lingual nerve, long ciliary nerves, long thoracic nerve, lower subscapular nerve, lumbar nerves, lumbar plexus, lumbar splanchnic nerves, lumboinguinal nerve, lumbosacral plexus, lumbosacral trunk, mandibular nerve, marginal mandibular branch of facial nerve, masseteric nerve, maxillary nerve, medial cord, medial cutaneous nerve of arm, medial cutaneous nerve of forearm, medial cutaneous nerve, medial pectoral nerve, medial plantar nerve, medial pterygoid nerve, median nerve, Meissner's plexus, mental nerve, middle cardiac nerve, middle meningeal nerve, motor nerve, muscular branches of the radial nerve, musculocutaneous nerve, mylohyoid nerve, nasociliary nerve, nasopalatine nerve, nerve of pterygoid canal, nerve to obturator internus, nerve to quadratus femoris, nerve to the Piriformis, nerve to the stapedius, nerve to the subclavius, nervus intermedius, nervus spinosus, obturator nerve, oculomotor nerve, olfactory nerve, ophthalmic nerve, optic nerve, ovarian plexus, palatine nerves, palmar branch of the median nerve, palmar branch of ulnar nerve, pancreatic plexus, patellar plexus, pelvic splanchnic nerves, perforating cutaneous nerve, perineal branches of posterior femoral cutaneous nerve, perineal nerve, pharyngeal branch of vagus nerve, pharyngeal branches of glossopharyngeal nerve, pharyngeal nerve, pharyngeal plexus, phrenic nerve, phrenic plexus, posterior auricular nerve, posterior branch of spinal nerve, posterior cord, posterior cutaneous nerve of arm, posterior cutaneous nerve of forearm, posterior cutaneous nerve of thigh, posterior scrotal nerves, posterior superior alveolar nerve, proper palmar digital nerves of median nerve, prostatic plexus (nervous), pudendal nerve, pudendal plexus, pulmonary branches of vagus nerve, radial nerve, recurrent laryngeal nerve, renal plexus, sacral plexus, sacral splanchnic nerves, saphenous nerve, sciatic nerve, sensory nerve, short ciliary nerves, sphenopalatine nerves, splenic plexus, stylohyoid branch of facial nerve, subcostal nerve, suboccipital nerve, superficial branch of the radial nerve, superficial fibular nerve, superior cardiac nerve, superior gluteal nerve, superior hypogastric plexus, superior labial nerve, superior laryngeal nerve, superior lateral cutaneous nerve of arm, superior mesenteric plexus, superior rectal plexus, supraclavicular nerves, supraorbital nerve, suprarenal plexus, suprascapular nerve, supratrochlear nerve, sural nerve, sympathetic trunk, temporal branches of the facial nerve, third occipital nerve, thoracic aortic plexus, thoracic splanchnic nerves, thoraco-abdominal nerves, thoracodorsal nerve, tibial nerve, transverse cervical nerve, trigeminal nerve, trochlear nerve, tympanic nerve, ulnar nerve, upper subscapular nerve, uterovaginal plexus, vagus nerve, ventral ramus, vesical nervous plexus, vestibular nerve, vestibulocochlear nerve, zygomatic branches of facial nerve, zygomatic nerve, zygomaticofacial nerve, and zygomaticotemporal nerve.

Examples of ganglia include but are not limited to dorsal root ganglia, cranial nerve ganglia, autonomic ganglia, basal ganglia, celiac ganglia, ciliary ganglion, geniculate ganglion, inferior cervical ganglion, jugular ganglion, long root of the ciliary ganglion, middle cervical ganglion, nodose ganglion, otic ganglion, petrous ganglion, pterygopalatine ganglion, semilunar ganglion, submandibular ganglion, superior cervical ganglion, superior ganglion of glossopharyngeal nerve, and superior ganglion of vagus nerve.

Examples of muscle include skeletal muscle, smooth muscle and cardiac muscle.

Additionally or alternatively, in some implementations, the adhesive hydrogel layer comprises any crosslinkable polymer precursor disclosed herein that has been cross linked with a redox active metal, such as $Fe^{3+}$, $Au^{3+}$, $V^{5+}$, or $Ag^+$.

Additionally or alternatively, in some implementations, the adhesive hydrogel layer comprises one or more of the following: (a) comprises polyethylene glycol; (b) comprises a crosslinked polymers selected from the group consisting of poly(ethylene oxide), poly(ethylene glycol-co-propylene glycol), poly(vinyl pyrrolidinone), poly(vinyl alcohol), acrylic polymers, and methacrylic polymers; (c) comprises a synthetically prepared monomer crosslinked to form a hydrogel, wherein the monomer is selected from the group consisting of ethylenically unsaturated hydrocarbons such as acrylic monomers and methacrylic monomers; (e) comprises a stimulus-responsive telechelic Dopa-modified polyethylene glycol; and/or (f) has a thickness selected from the group consisting of about 0.2 mm, about 0.25 mm, about 0.5 mm, about 0.75 mm, about 1 mm, about 1.25 mm, about 1.5 mm, about 1.75 mm, about 2 mm, about 2.25 mm, about 2.5 mm, about 2.75 mm, about 3 mm, about 3.25 mm, and about 3.5 mm.

The conformable neural interface system described herein can be used in the treatment of a wide variety of indications. For example, in one aspect, the conformable neural interface system of the present disclosure may be used to stimulate or modulate (e.g., activate or inhibit) one or more target tissues disclosed herein for the treatment of a particular disease or medical condition. For example, the disease or medical condition may affect a system or organ selected from the group consisting of heart, brain, lungs, an organ of a respiratory system, liver, kidney, stomach, small intestine, large intestine, a muscle of a limb, central nervous system, peripheral nervous system, pancreas, bladder, skin, urinary tract, thyroid gland, pituitary gland, and adrenal cortex. Additionally or alternatively, in some implementations, the conformable neural interface system of the present disclosure may be used to modulate the levels of one or more hormones, neurotransmitters, cells (and in particular immune cells), interleukins, cytokines, lymphokines, chemokines, growth factors, and/or enzymes in a subject.

In one example, the modulation of nerve tissues such as autonomic nerve tissue including central and peripheral, sympathetic and parasympathetic, may be used to achieve a desired physiological result or treatment of various medical conditions. In some implementations, the method of treatment involves electrical activation of one or more nerves. Unilateral activation or bilateral activation may be utilized.

Electrical nerve modulation (nerve activation, stimulation, and/or inhibition) is accomplished by applying an energy signal (pulse) at a certain frequency to the neurons of a nerve (nerve stimulation). The energy pulse causes depolarization of neurons within the nerve above the activation threshold resulting in an action potential. The energy applied is a function of the current (or voltage) amplitude and pulse width or duration. Biphasic pulses help inhibit buildup of charge and are often used in some implementations. Activation or inhibition can be a function of the frequency of the energy signal, with low frequencies on the order of about 1 to about 50 Hz resulting in activation of a nerve for some implementations and high frequencies greater than about 100 Hz resulting in inhibition of a nerve for some implementations. Inhibition can also be accomplished by continuous energy delivery resulting in sustained depolarization. Different neuronal types may respond to different energy signal frequencies and energies with activation or inhibition.

Various stimulation patterns, ranging from continuous to intermittent, may be utilized for various implementations. With intermittent stimulation of nerves, an energy signal is delivered to a nerve or nerve tissue for a period of time at a certain frequency during the signal on-time. The signal on-time is followed by a period of time with no energy delivery, referred to as signal-off time. The ratio of the signal on-time to the sum of the signal on-time plus the signal off time is referred to as the duty cycle and it can in some implementations range from about 1% to about 100%. Alternatively, nerve stimulation may be conducted at nearly a continuous, or 100%, duty cycle.

To help determine the strength and/or duration of electrical stimulation required to produce the desired effect, in some implementations, a patient's response to and/or need for treatment is monitored. For example, muscle activity (e.g., limb EMG), electrical activity of a nerve (e.g., ENG), and/or electrical activity of the brain (e.g., EEG) may be detected. Other measures of the state of the patient may additionally or alternatively be detected. For instance, medication, neurotransmitter, cells (and in particular immune cells), hormone, interleukin, cytokine, lymphokine, chemokine, growth factor, and/or enzyme levels or their changes, and/or levels or changes in other substance(s) borne in the blood, cerebrospinal fluid (CSF), bronchoalveolar lavage fluid (BALF) and/or breath may be detected, using conventional detection methods known in the art.

In addition to the duty cycle and signal parameters (frequency, on-time, current pulse amplitude, and pulse width) are treatment parameters. Therapy may be delivered at different intervals during the day or week, or continuously. Continuous treatment may prevent the progression of a disease or condition during the off therapy time. Intermittent treatment may prevent the development of tolerance to the therapy. A desirable intermittent therapy embodiment may be, for example, about 18 hours on and about 6 hours off, about 12 hours on and about 12 hours off, about 3 days on and about 1 day off, about 3 weeks on and about one week off or some other combination of daily or weekly cycling. Alternatively, treatment may be delivered at a higher interval rate, say, about every three hours, for shorter durations, such as about 2 minutes to about 30 minutes. The treatment duration and frequency may be tailored to achieve a desired result. Treatment duration for some implementations may last for as little as a few minutes to as long as several hours.

X. Definitions

The following definitions are provided to facilitate understanding of certain terms used throughout this specification.

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein "subject" or "patient" or "individual" refers to any subject, patient, or individual, and the terms are used interchangeably herein. In this regard, the terms "subject," "patient," and "individual" includes mammals, and, in particular humans.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

As used herein, "about" will be understood by persons of ordinary skill in the art and will vary to some extent depending upon the context in which it is used. Certain ranges are presented herein with numerical values being preceded by the term "about". The term "about" is used herein to provide literal support for the exact number that it precedes, as well as a number that is near to or approximately the number that the term precedes. If there are uses of the term which are not clear to persons of ordinary skill in the art, given the context in which it is used, "about" will mean up to plus or minus 10% of the particular term, for example, $\pm1\%$, $\pm2\%$, $\pm3\%$, $\pm4\%$, $\pm5\%$, $\pm6\%$, $\pm7\%$, $\pm8\%$, $\pm9\%$ or $\pm10\%$.

It should be noted that the terms "exemplary," "example," "potential," and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

Additional background and supporting information can be found in the following document, which is hereby incorporated by reference, along with all publicly available documents referenced herein directly or indirectly: X. C. Ong et al., "Ultra-compliant peripheral nerve cuff electrode with hydrogel adhesion," 2018 *IEEE Micro Electro Mechanical Systems (MEMS)*, Belfast, 2018, pp. 376-379 (doi: 10.1109/MEMSYS.2018.8346566).

"Dorsal root ganglia (DRG)" are enlargements of the spinal roots that house cell bodies for all primary afferent neurons projecting from the periphery. See FIG. 25. The structure is surrounded by epineurium and completely segregated from efferent motor pathways which travel through the ventral root. Each DRG houses cell bodies and axons projecting from a particular dermatomal region of the limbs or body, and cell bodies tend to cluster around the outer circumference of the DRG.

The "nervous system" is a complex network of nerve cells, or neurons, found centrally in the brain and spinal cord and peripherally in the various nerves of the body. Neurons have a cell body, dendrites and an axon.

A "nerve" is a group of neurons that serves a particular part of the body. Nerves can contain several hundred neurons to several hundred thousand neurons. Nerves often contain both afferent neurons (which carry signals back to the central nervous system) and the efferent neurons (which carry signals to the periphery). Electrical signals are conducted via neurons and nerves. Neurons release neurotransmitters at synapses with other nerves to allow continuation and modulation of the electrical signal. A "ganglion" refers to a group of neuronal cell bodies in one location.

As used herein, the term "subject" or "patient" are used interchangeably and refer to an individual organism, a vertebrate, a mammal, or a human. In certain implementations, the patient or subject is a human.

References herein to the positions of elements (e.g., "top," "bottom," "above," "below") are merely used to describe the orientation of various elements in the Figures. It should be noted that the orientation of various elements may differ according to other exemplary embodiments, and that such variations are intended to be encompassed by the present disclosure.

XI. Examples

The following examples are provided to illustrate the present invention. It should be understood, however, that the invention is not to be limited to the specific conditions or details described in these examples. Throughout the specification, any and all references to a publicly available document, including a U.S. patent, are specifically incorporated by reference. Examples 1-7 relate to the conformable neural interface device manufactured with an integrated adhesive hydrogel layer in accordance with the process described in FIGS. 2 and 3A-3F. Example 8 relates to the conformable neural interface device that is manufactured in accordance with the process described in FIGS. 14A-14H and 15A-15D and subsequently placed on a suture-like anchor device after fabrication of the neural interface device and prior to surgically implanting the neural interface device within a subject.

Example 1

Example process steps for fabricating a neural interface device according to various embodiments are illustrated in FIGS. 3A-3F. In example implementations, a plasma etch, such as a 100 Watt (W) oxygen barrel etch (e.g., International Plasma Corporation, Hayward, CA) may be performed after every photoresist development and removal step.

A 10% PAA-sodium salt solution (or other suitable solution) was spin-coated on four-inch-diameter Si or glass wafers. The wafer was then be soaked in 2 molar (M) $CaCl_2$ for two minutes, rinsed with 0.5 M $CaCl_2$ solution followed by deionized water, and baked at 100° C. for one minute.

A 250 nm thick parylene-C layer was then deposited on top of the PAA using a Labcoter 2 (Specialty Coating Systems, Indianapolis, IN). A 2.4 micrometer (μm) thick positive photoresist (AZ4210, MicroChemicals GmbH, Ulm, Germany) was spun on the parylene-C and patterned using an MA6 contact aligner (Karl Süss, Garching, Germany).

Following development of the photoresist in AZ developer (MicroChemicals), parylene-C was patterned with a timed oxygen reactive-ion etch (Phantom RIE, Trion, Clearwater, FL).

With reference to FIG. 3A, these steps yielded a silicon substrate 302 coated with PAA as sacrificial material 304 which was about 400 nm thick and patterned parylene-C as a first polymer layer 306 which was about 250 nm in thickness.

A Pt layer of about 300 nm in thickness was then deposited using a 2400-6J sputtering system (PerkinElmer Inc., Waltham, MA) and patterned using photolithography with 2.4 μm-thick positive photoresist (AZ4210) followed by ion milling using a Millatron (Commonwealth Scientific, Alexandria, VA).

With reference to FIG. 3B, these steps yielded the structure of FIG. 3A with a patterned electrically-conductive layer 310. The wafer (substrate 302) was then be immersed in acetone and ultrasonic energy was applied to remove redeposited material on the sidewalls of the Pt traces.

Figure 5:
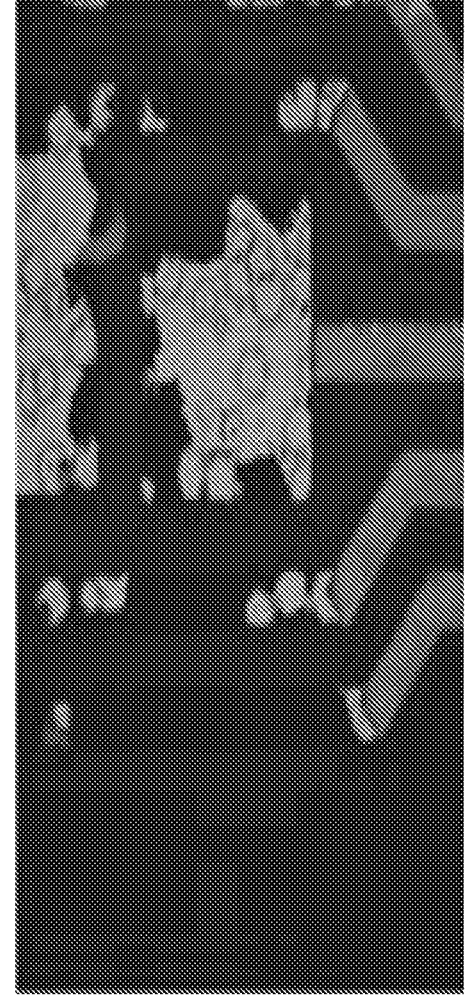
FIG. 5 illustrates observed damage to pads and electrode if platinum (Pt) is patterned using lift-off due to exposure of PAA to developer.
Figure 6:
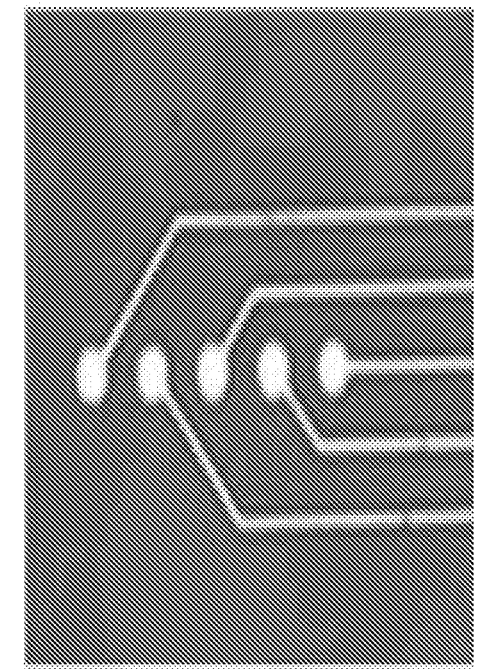
FIG. 6 illustrates successful patterning of example contact pads using ion milling in accordance with at least some embodiments of the present disclosure.

With reference to FIG. 5, damage to the contact pads and electrodes occurs when Pt is patterned using lift-off, because of the incompatibility of PAA with the alkaline developer solution. Depositing Pt and patterning the layer by ion milling helps the Pt be more effective as a barrier between PAA and the developer solution and facilitates successful patterning of the Pt layer, as illustrated in FIG. 6.

A second parylene-C layer 320 of about 250 nm in thickness was then deposited using the Labcoter 2 (see FIG. 3C) and patterned using a timed oxygen etch with Phantom RIE.

Stiffening of the pad contacts, which may help ensure robust electrical interface with an external connector, which may connect to other electronic/computing components, and via which electrical signals may be sent to and/or received from the neural interface device, may be achieved by depositing photo-patternable epoxy SU-8 2010 (MicroChem Corporation) using spin coating (see SU-8 layer 330 in FIG. 3D) in a layer of about 25 μm-thick.

Because abrupt changes in stiffness creates stress concentrators that can lead to damage when stress is applied during handling, the SU-8 may, in various embodiments, be patterned using the MA6 to impart a gradual transition in stiffness from the flexible electrode region to the stiff pad region by varying the volume ratio of SU-8 to hydrogel using patterned pores with varying density. As shown in FIGS. 4A and 4B, in certain implementations of bioelectronic interface device 400, the density of the pores may start from substantially 0% at the pad region 420 (which interfaces with an external connector) and may be gradually increased until there is no SU-8 (i.e., 100% pore density) in the electrode contact region 430 (which interfaces with the nerve) of the device.

With reference to FIG. 3E, in various embodiments, hydrogel in the sol state 340 is drop cast onto a detachable surgical support substrate, such as a Parafilm (Bemis Company, Inc.) substrate. In certain implementations, the hydrogel may be synthesized separately as a stimulus-responsive telechelic Dopa-modified polyethylene glycol-based hydrogel.

Example 2

In various embodiments, the hydrogel includes $H^+$ ions that dissolve the PAA, releasing the device after a certain time (e.g., about 2 hours or less). At the same time, gelation of the hydrogel occurs, represented as hydrogel in the gel state 350 in FIG. 3F. The hydrogel, with the attached device, may then be removed from the glass or silicon substrate 302.

Figure 7:
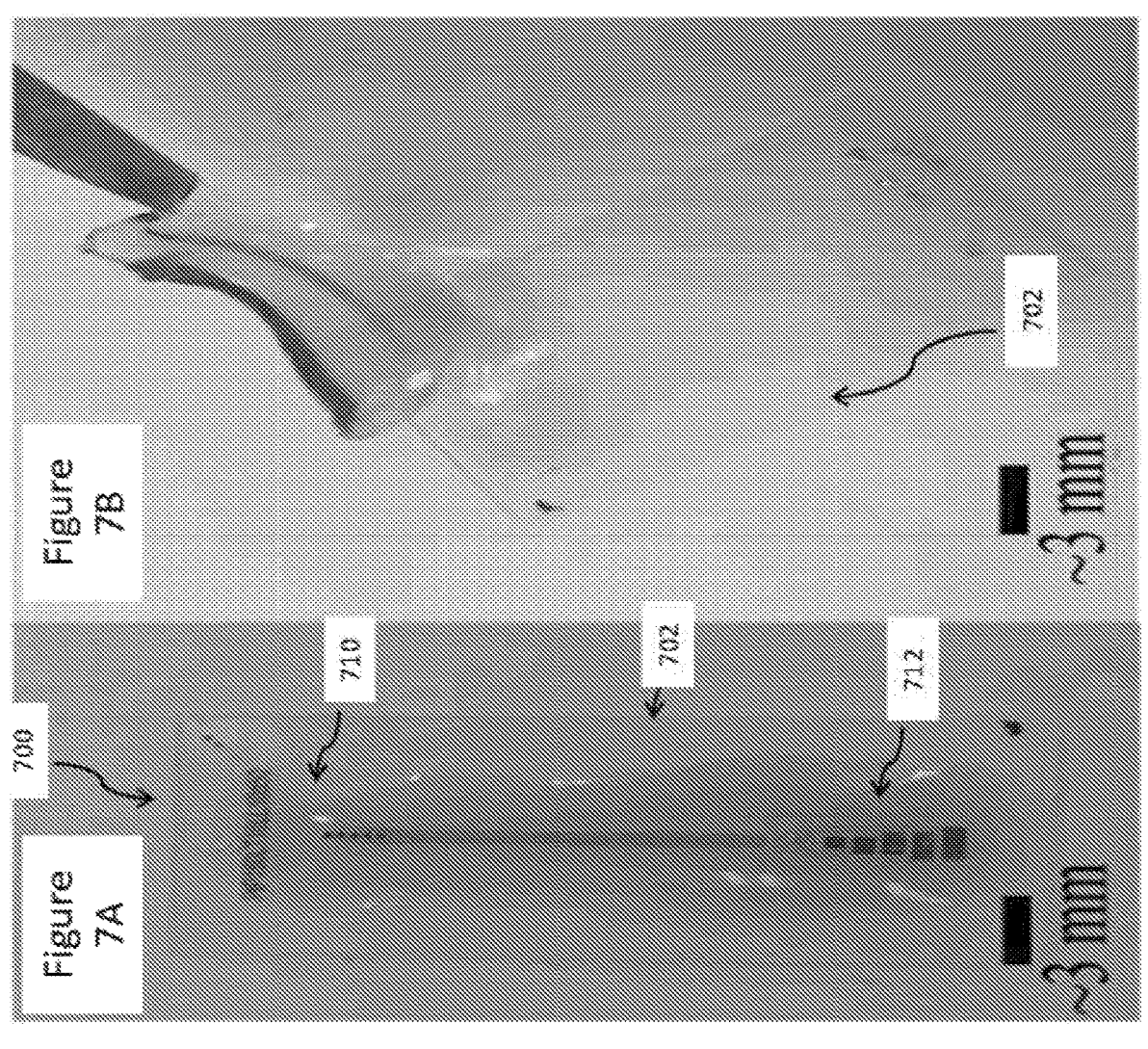
FIGS. 7A and 7B depict an example process of releasing an example probe from a glass substrate in accordance with at least some embodiments of the present disclosure.

Optical images in FIGS. 7A and 7B illustrate the successful removal/release of a device 700 (with electrode region 710 and pad region 712) from a glass substrate 702. [PEG-Dopa]₄ hydrogel in the sol state may be poured over devices fabricated on PAA (FIG. 7A) and after PAA is dissolved, the hydrogel with attached device may be peeled (FIG. 7B).

Example 3

Figure 8:
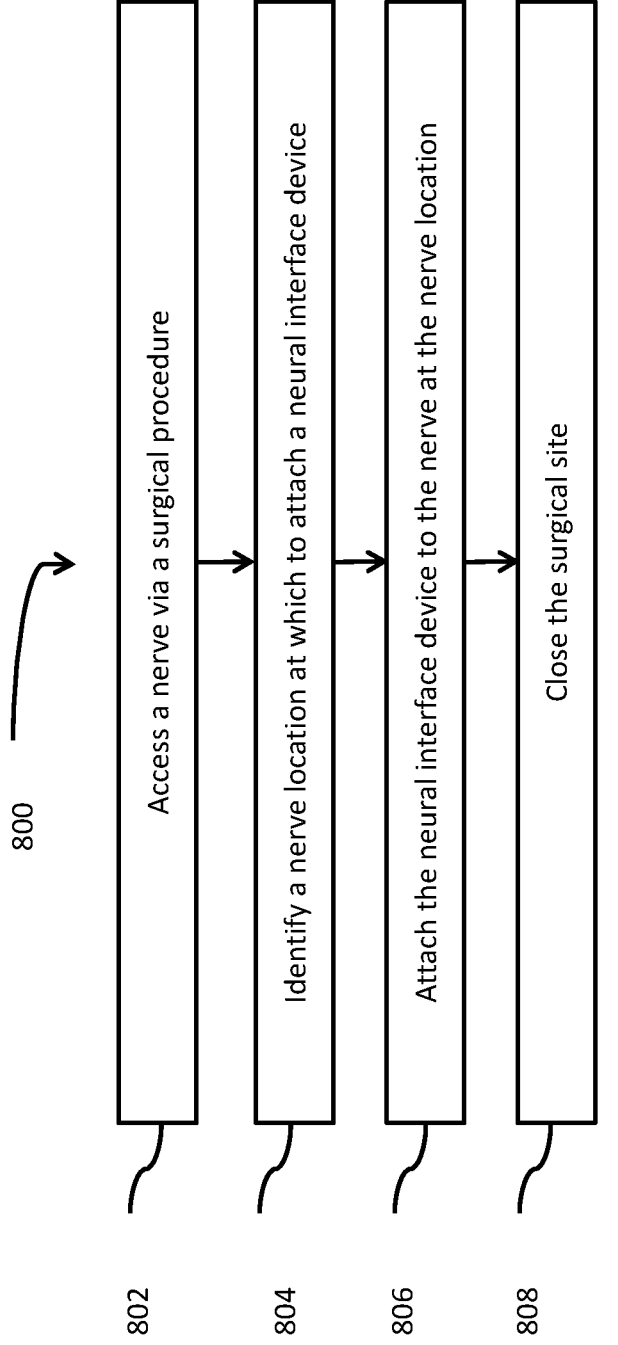
FIG. 8 is an illustrative flowchart 800 for an example method of securing a neural interface device to a nerve in accordance with at least some embodiments of the present disclosure. The flowchart depicts the following steps: (1) access a nerve, tissue, or ganglion via a surgical procedure (802); (2) identify a nerve, tissue or ganglion location at which to secure a nerve interface device (804); (3) secure the nerve interface device to the nerve, tissue, or ganglion at the nerve location (806); and (4) close the surgical site (808).

Referring to FIG. 8, an example process 800 for securing a neural interface device to a tissue, such as a nerve is illustrated. At process step 802, a surgeon or other healthcare provider may access a nerve via a surgical procedure. At process step 804, a target site may be identified as a destination on the nerve where a neural interface device is to be placed. At process step 806, the neural interface device may be secured to the nerve at the location on the nerve that was identified at process step 804. With the neural interface device secured, at process step 808, the surgical site may be closed.

The neural interface device facilitates an interface with computing devices or other electronic components for one-way (e.g., recording or stimulating) or two-way (e.g., recording and stimulating) communication with the nerve. Other computer devices or electronic components could be configured to record other physiological signals that determine the stimulation of the nerve by the device. This is known as closed-loop control.

Example 4

In in vitro experiments, measurements of the electrochemical impedance of 75 μm-radius electrode contacts on a hydrogel substrate fabricated using the described process were recorded.

Figures 9A, 9B:
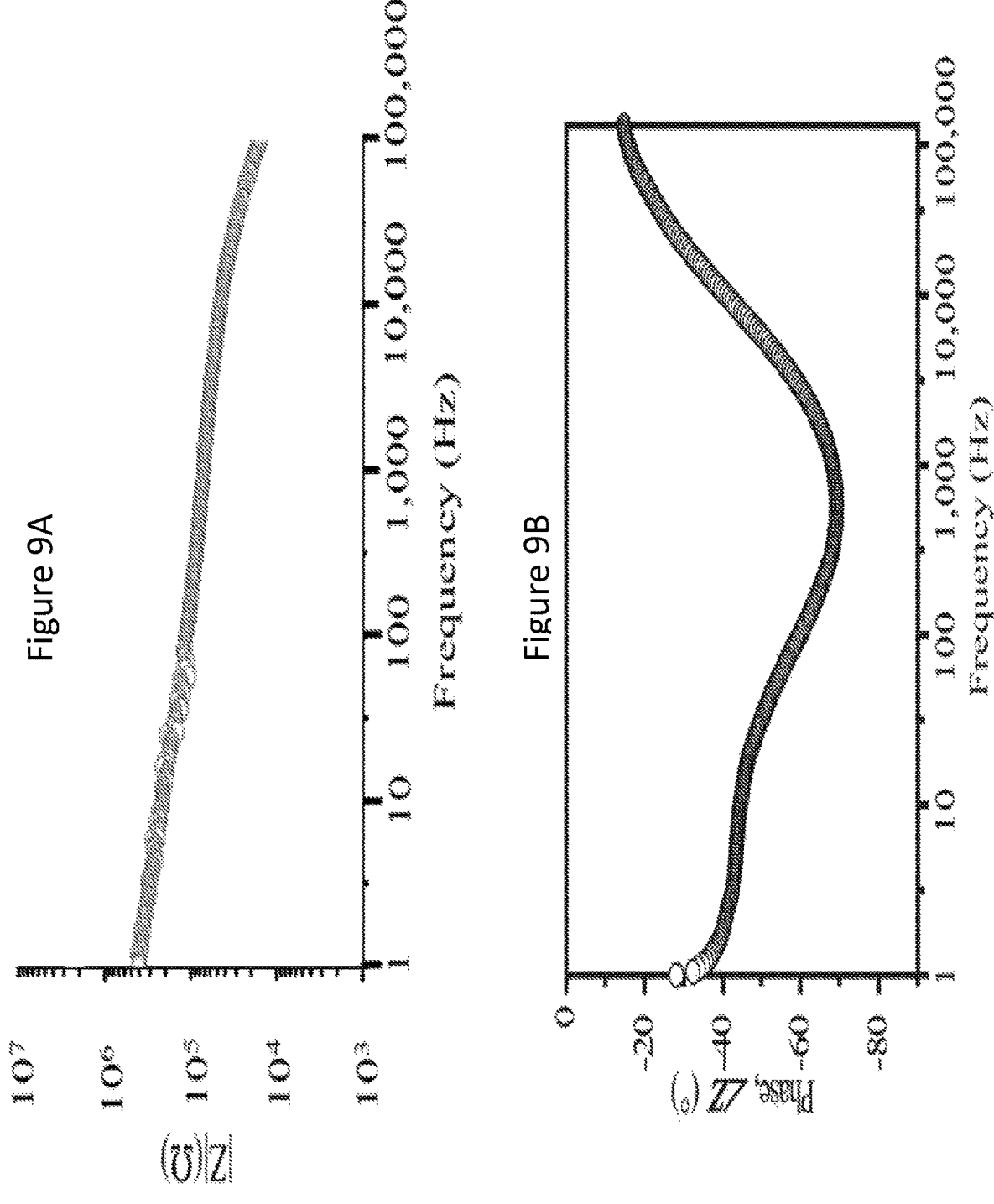
FIGS. 9A-9B provide impedance magnitude versus frequency (FIG. 9A) and impedance phase versus frequency (FIG. 9B) for example 75 μm-radius Pt electrode contacts fabricated using a disclosed process in accordance with at least some embodiments of the present disclosure.

A multi-channel potentiostat-galvanostat (VMP3, Biologic, Knoxville, TN) was employed. A three-electrode cell configuration in 1× phosphate buffered saline used Ag|AgCl as the reference electrode and Pt as the counter electrode. FIG. 9A provides frequency plots for the impedance of one of the electrodes. At a frequency of one kilohertz (kHz), the impedance magnitude was approximately 100 kilo-ohm (kΩ), which is sufficiently low to detect signals.

From FIG. 9B, the phase of the impedance of the electrode at 1 kHz was approximately negative 70° C., indicating that the behavior of the electrode was largely capacitive at this frequency in this experiment.

Example 5

An in vivo experiment was used to further illustrate device functionality.

Figure 10:
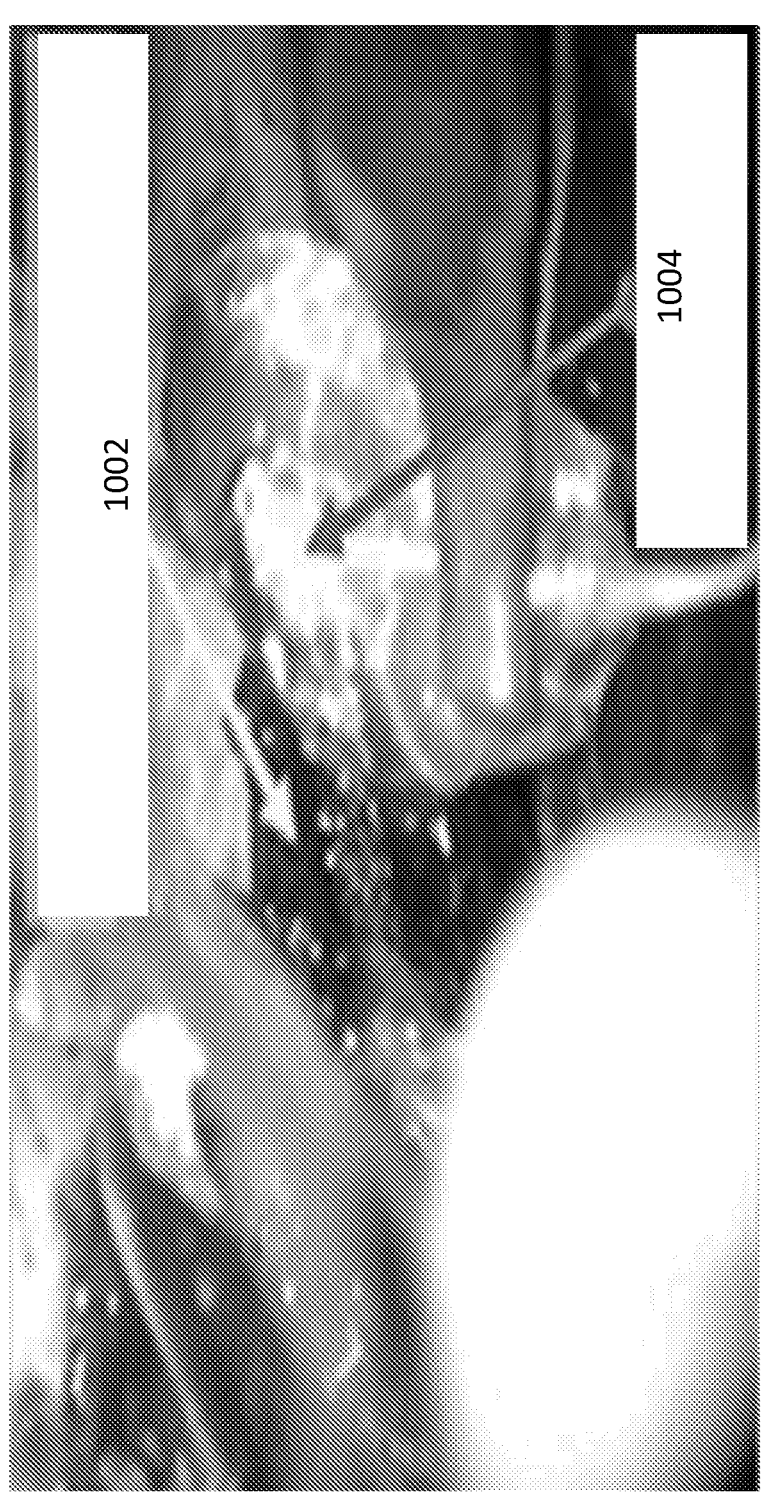
FIG. 10 provides an image of a hydrogel multi-electrode array on the L7 dorsal root ganglion of a cat in accordance with at least some embodiments of the present disclosure, with a hydrogel-based device 1002 and an Omnetics connector 1004 depicted.

The neural interface device 1002 (FIG. 10) was placed on the surface of the L7 dorsal root ganglia of a cat, as shown in FIG. 10, to record single-unit action potentials. The bond pads may connect to wire cables using silver paste and may be encased in silicone to insulate the pads. The wire cables may attach to an Omnetics connector 1004 that is compatible with the acquisition system.

The measured impedance magnitude of the electrode contact after placement in the experiment was 32 kΩ at 1 kHz. The suitably low value indicates that electrode contacts were not damaged during placement.

Figures 11A, 11B:
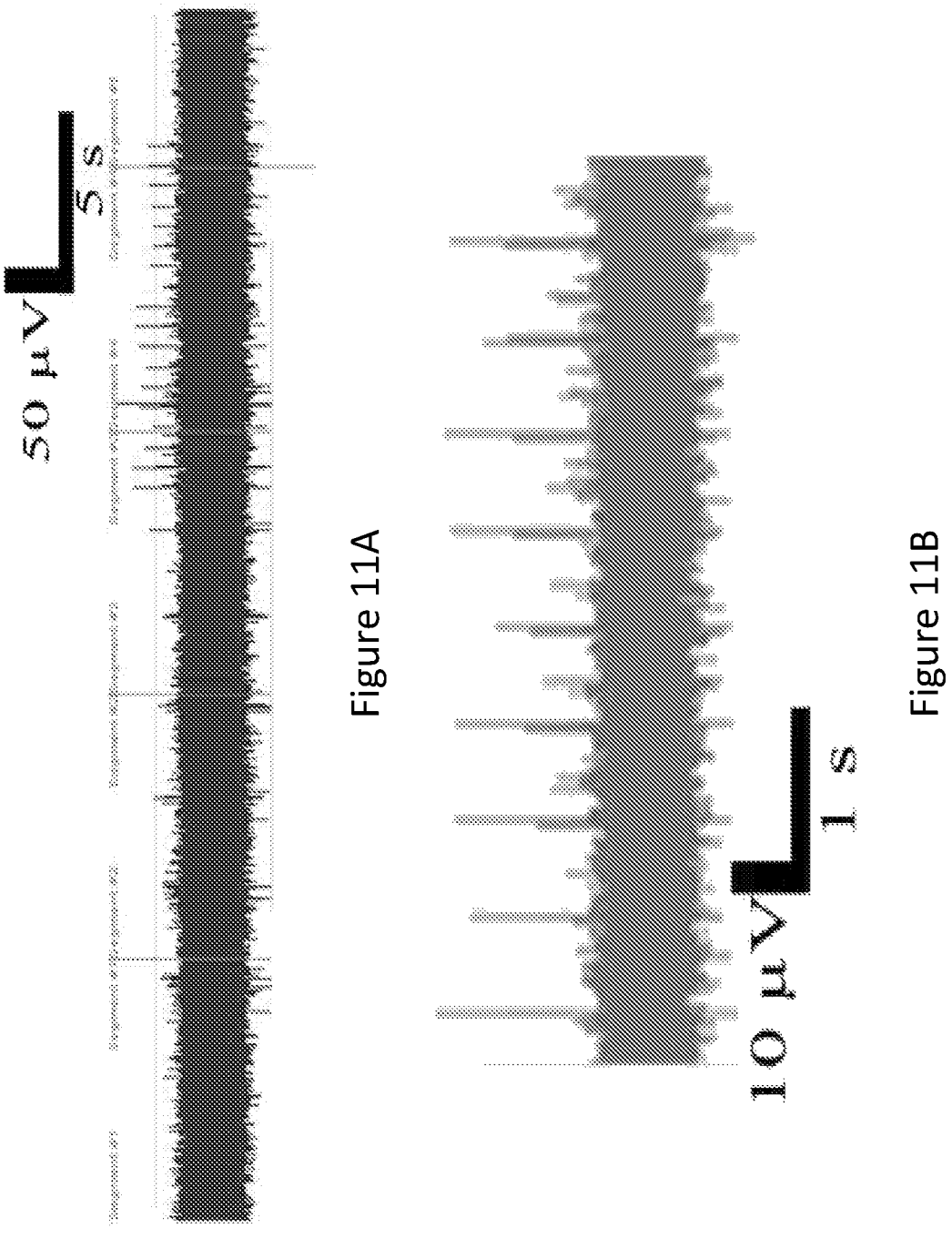
FIGS. 11A and 11B represent spikes recorded using a fabricated neural interface device in accordance with at least some embodiments of the present disclosure.

Moving a limb of the cat evoked action potentials in the somatosensory system that excited the proprioceptive and cutaneous sensory receptors whose cell bodies are in the dorsal root ganglion. These action potentials were conducted through the peripheral nerves to the dorsal root ganglia where the neural interface device was placed. The recorded signals from the neural interface device are shown in FIG. 11A, with zoomed-in images of the spikes of FIG. 11A shown in FIG. 11B.

The successful recording of single-unit action potentials indicates functionality of the neural interface device.

Example 6

FIGS. 12A-12C provide representative views of example bioelectronic neural interface devices and implantation thereof. FIG. 12A provides a ventral view of a neural interface device during surgical implantation. In particular, FIG. 12A illustrates a neural interface device 1202 secured to a cervical vagus nerve 1204, which passes near trachea 1206 and carotid artery 1208. The neural interface device 1202 can be fabricated using the fabrication process described herein. The midline is represented by a dotted line and indicated by numeral 1210. A connector 1212 interfaces with the probe 1212 at one end and leads to one or more machine interfaces (not pictured), which may include, e.g., sensors, generators, and other electronic and computing devices configured to perform such tasks as generating, delivering, sensing, measuring, analyzing, and reporting of electric signals.

In FIG. 12A, the upward direction corresponds with the rostral, the downward direction corresponds with the caudal, the leftward direction corresponds with the medial, and rightward direction corresponds with the lateral.

In the example neural interface device 1202 depicted in FIG. 12B, four monopolar electrode contacts are illustrated. The electrode contacts are labeled "1," "2," "3," and "4," and each of the electrode contacts includes an "a" connection and a "b" connection. In FIG. 12B, the upward direction corresponds with the rostral, and the downward direction corresponds with the caudal. As such, "2a" corresponds with the "a" connection of electrode contact "2," and "2b" corresponds with the "b" connection of electrode contact "2." The electrical return connection (i.e. the "ground") can be connected to a metal screw in the skull of the rat.

As can be seen in FIG. 12B, the electrode contacts can be placed in different longitudinally positions along nerve 1204. FIG. 12C provides a rostral view illustrating a cross-section of the nerve 1204. As shown, electrode contacts "1," "2," "3," and "4" are numbered arbitrarily in a crosswise manner. In FIG. 12C, the leftward direction corresponds with the medial, and the rightward direction corresponds with the lateral.

Example 7

The use of sticky [PEG-Dopa]₄ hydrogels with microfabricated processes to attach more compliant electrodes was successfully demonstrated. The neural interface device was released from its handle substrate. During surgical operation on a rat, the electrode region of the neural interface device was placed onto an adhesive hydrogel layer that was formed on a detachable surgical support substrate. The assembly of the electrode region and the adhesive hydrogel layer was aligned to the nerve. Subsequently, one side of the adhesive hydrogel layer was peeled from the detachable surgical support substrate, wrapped around the nerve with the device in between, and then adhered to the other side of the hydrogel disk.

In example embodiments, such a process eliminates or reduces the need to expose the hydrogel to harsh chemicals during processing. The microfabrication-based process flow may be modified by using ion milling instead of lift-off for the Pt contacts to overcome the incompatibility of PAA with alkaline developer solutions.

In vitro results indicated that the magnitude of the impedance (100 kΩ at 1 kHz) was sufficiently low to acquire action potential signals. In vivo results of the device, where successful single-unit action potentials were acquired in the dorsal root ganglia of a cat, also demonstrated that the device is functional.

Example 8

A conformable neural interface system was designed using the processes described in FIGS. 14A-14H, 15A-15D and 16.

Methods for recording the electrically-stimulated compound action potential were similar to those described in Horn C C, Friedman MI, *Brain Res.* 1060(1-2):153-61 (2005). A Sprague-Dawley rat was anesthetized with urethane (1 g/kg; ip). A longitudinal incision was made on the ventral surface of the neck to access the left cervical vagus trunk. At this cervical location, a triangular wedge of the detachable surgical support substrate was inserted under the nerve with a circle of hydrogel comprising a polymer precursor (4-arm poly(ethylene glycol) that is end-modified with catechol-bearing dopamine groups) placed on the substrate. The polymer precursor of the hydrogel was cross-linked using $HAuCl_4$ ($Au^{3+}$) as a redox active metal.

Next, a MEMS electrode probe was placed on the hydrogel layer followed by positioning the surgical substrate under the vagus nerve such that the nerve rested on the electrode probe and hydrogel. The hydrogel was folded in half leaving the electrode probe encased between the hydrogel and nerve, thus allowing the probe to have intimate contact with the nerve. See FIGS. 20A-E, 21 and 22A-D. FIG. 23 shows an exemplary image of the conformable neural interface system used to contact the vagus nerve in the rat.

An incision from the top of the xiphoid process to the lower abdomen was made to expose the abdominal viscera. The stomach was retracted caudally and the liver was displaced to the right of the animal to reveal the ventral trunk of the abdominal vagus nerve. The body cavity was filled with warm (37° C.) mineral oil. The subdiaphragmatic ventral trunk, rostral to the common hepatic branch, was placed on a platinum-iridium bipolar hook electrode (FHC, Bowdoinham, ME). Nerve signals were amplified by 20K using differential AC amplifier (WPI) with low (100 Hz) and high (3 kHz) frequency cutoffs. An isolated stimulator (Model 4100; A-M Systems) was used to produce constant current stimulus pulses applied to the cervical vagus, 0.5 ms in duration (biphasic). Experiments were conducted using a computer controlled sequence of 10 stimulus pulses (Spike 2; Cambridge Electronic Design), each separated by 500 ms. Nerve responses after each stimulus pulse were averaged for these 10 trials using Python programming.

As shown in FIG. 24, the conformable neural interface system was effective in stimulating the vagus nerve when attached to the cervical vagus nerve. The compound action potential (CAP), produced by using 0.1 mA, shows the aggregated response of many vagal fiber types according to their conduction velocity. Trials with different current levels were used and 0.1 mA was the lowest current, which stimulated largest range of fiber type conduction velocities. Without wishing to be bound by theory, it is believed that the superior performance of this conformable neural interface system can be attributed in part to the presence of free catechols in the $Au^{3+}-[PEG-Dopa]_4$ hydrogels.

The embodiments described herein have been described with reference to drawings. The drawings illustrate certain details of specific embodiments that implement the systems, methods and programs described herein. However, describing the embodiments with drawings should not be construed as imposing on the disclosure any limitations that may be present in the drawings.

It is important to note that the construction and arrangement of the devices, assemblies, and steps as shown in the various exemplary embodiments is illustrative only. Additionally, any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described to explain the principals of the disclosure and its practical application to enable one skilled in the art to utilize the various embodiments and with various modifications as are suited to the particular use contemplated. Other substitutions, modifications, changes and omissions may be made in the design, operating conditions and arrangement of the embodiments without departing from the scope of the present disclosure as expressed in the appended claims.

What is claimed is:

1. A conformable neural interface system comprising:
(a) a neural interface device for interfacing with a nerve, the neural interface device comprising a probe region having at least one electrode on a nerve-facing surface, at least one conductive trace electrically coupled to the electrode, and at least one insulating polymer layer overlying the conductive trace; and
(b) a suture-like anchor device comprising an elongated adhesive hydrogel layer that: (i) is external to the insulating polymer layer of the probe region, (ii) comprises a gel polymer network that comprises a cross-linkable polymer precursor crosslinked with a redox active metal, and (iii) is configured, in use, to be wrapped around the nerve with opposing portions of the elongated adhesive hydrogel layer contacting and adhering to each other to secure the probe region such that the electrode is maintained in non-penetrating contact with the nerve.

2. The conformable neural interface system of claim 1,
(a) for use in stimulating or inhibiting a nerve in a subject in need thereof;
(b) for use wherein the subject suffers from a disease or medical condition that affects a system or an organ selected from the group consisting of heart, brain, lungs, an organ of a respiratory system, liver, kidney, stomach, small intestine, large intestine, a muscle of a limb, central nervous system, peripheral nervous system, pancreas, bladder, skin, urinary tract, thyroid gland, pituitary gland, and adrenal cortex; and/or
(c) for use in modulating the levels of one or more hormones, neurotransmitters, immune cells, interleukins, cytokines, lymphokines, chemokines, growth factors, and/or enzymes in a subject.

3. The conformable neural interface system of claim 1, wherein the redox active metal is $Fe^{3+}$, $Au^{3+}$, $V^{5+}$, or $Ag^+$.

4. The conformable neural interface system of claim 1, wherein the gel polymer network has an effective interfacial adhesion of between 0.1 and 10 J/m^2.

5. The conformable neural interface system of claim 1, wherein the gel polymer network has a fracture energy between about 100 and about 1,000 J/m^2.

6. The conformable neural interface system of claim 1, wherein the gel polymer network comprises a dopamine moiety and/or a stimulus-responsive telechelic Dopa-modified polyethylene glycol-based hydrogel.

7. The conformable neural interface system of claim 1, wherein the gel polymer network has a thickness from about 200 microns to about 3.5 mm.

8. The conformable neural interface system of claim 1, wherein the gel polymer network comprises a drug, a ligand, or a peptide that binds to a site expressed on a target tissue.

9. The conformable neural interface system of claim 1, wherein the gel polymer network is deposited on a detachable surgical support substrate, wherein the detachable surgical support substrate comprises an inert polymer film.

10. The conformable neural interface system of claim 1, wherein the Young's modulus of the suture-like anchor device is between 10 kPa and 100 kPa.

11. The conformable neural interface system of claim 1, wherein the shear modulus (G) of the suture-like anchor device is between 1 kPa and 100 kPa.

12. The conformable neural interface system of claim 1, wherein the yield strength of the suture-like anchor device is between 1 Pa and 1000 Pa.

13. The conformable neural interface system of claim 1, wherein the redox active metal is a metal ion.

14. The conformable neural interface system of claim 1, wherein the redox active metal is gold.

15. A conformable neural interface system, comprising:
(a) a neural interface device for interfacing with a nerve, the neural interface device comprising a probe region having a nerve-facing surface with at least one electrode; and
(b) a suture-like anchor device comprising an elongated adhesive hydrogel layer comprising a gel polymer network that is configured to couple with the probe region and that comprises a crosslinkable polymer crosslinked with a redox active metal ion, the adhesive hydrogel layer bonded directly to the nerve-facing surface of the probe region so as to at least partially surround the electrode, the hydrogel layer securing the probe region to the nerve without penetrating the nerve.

16. The conformable neural interface system of claim 15, wherein the crosslinkable polymer is cross linked with the redox active metal ion via redox-mediated crosslinking.

17. The conformable neural interface system of claim 15, wherein the elongated adhesive hydrogel layer comprises a first portion and a second portion that are not in contact with each other before the elongated adhesive hydrogel layer is wrapped around the nerve, and wherein the elongated adhesive hydrogel layer is configured such that the first portion and the second portion bond together when they make contact with the elongated adhesive hydrogel layer wrapped around the nerve to secure the at least one electrode to the nerve.

18. The conformable neural interface system of claim 15, wherein the redox active metal ion is a gold ion.

19. The conformable neural interface system of claim 1, wherein the adhesive hydrogel layer is an elongated sheet-like hydrogel layer on a detachable surgical support substrate.

20. The conformable neural interface system of claim 1, wherein the neural interface device further comprises a contact pad region and a cable connecting the probe region to the contact pad region, and wherein the neural interface device comprises a gradient of increasing stiffness from the probe region to the contact pad region.

21. The conformable neural interface system of claim 1, wherein the at least one electrode has a separation of no more than 25 nm from the nerve-facing surface of the probe region.

22. The conformable neural interface system of claim 1, wherein the at least one electrode is configured to protrude or extend out no more than 25 nm from the nerve-facing surface of the probe region.

23. The conformable neural interface system of claim 1, wherein the neural interface device further comprises an epoxy-based layer having a patterned array of pores with a pore-density gradient that increases from a contact pad region toward an electrode region, thereby providing variation in stiffness from the probe region to the contact pad region, the variation being achieved at least in part by varying a volume ratio of the epoxy-based layer to the hydrogel via said patterned pores.

24. The conformable neural interface system of claim 1, wherein each electrode is electrically connected to a contact pad region by at least two separate wires forming an electrical loop, such that continuity of each electrode can be verified prior to implantation.

25. The conformable neural interface system of claim 1, wherein the neural interface device comprises at least two tabs, each tab comprising at least one electrode, and wherein the electrodes are staggered in distance from a spine of the probe to provide circumferentially distributed contact points along the nerve.

26. The conformable neural interface system of claim 15, wherein the at least one electrode has a separation of no more than 25 nm from the nerve-facing surface of the probe region.

27. A conformable neural interface system comprising:
a neural interface device for interfacing with a nerve, the neural interface device comprising a probe region having at least one electrode on a nerve-facing surface, and a connector region configured to electrically couple the probe region to external instrumentation; and
an anchor device comprising an adhesive hydrogel layer comprising a gel polymer network that comprises a crosslinked polymer or a crosslinkable polymer precursor crosslinked with a metal ion, the hydrogel layer arranged to secure the probe region to the nerve so that the electrode is maintained in non-penetrating contact with the nerve;
wherein the probe region is more compliant than the connector region, a difference in compliance being provided at least in part by a difference in material composition or structure between the two regions.

* * * * *